(12) United States Patent
Brindley et al.

(10) Patent No.: US 10,525,258 B2
(45) Date of Patent: *Jan. 7, 2020

(54) IMPLANTABLE ELECTRODE ARRAY ASSEMBLY INCLUDING A CARRIER WITH PACKAGED CONTROL MODULES

(71) Applicant: Stryker Corporation, Kalamazoo, MI (US)

(72) Inventors: Robert A. Brindley, Delton, MI (US); John J. Janik, Hudsonville, MI (US); Edward Chia-Ning Tang, Ann Arbor, MI (US); James Bernard Dunlop, Colorado Springs, CO (US); Leland Joseph Spangler, Manitou Springs, CO (US)

(73) Assignee: Stryker Corporation, Kalamazoo, MI (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/944,075

(22) Filed: Apr. 3, 2018

(65) Prior Publication Data

US 2018/0296823 A1 Oct. 18, 2018

Related U.S. Application Data

(60) Continuation of application No. 15/713,291, filed on Sep. 22, 2017, now Pat. No. 9,950,154, which is a
(Continued)

(51) Int. Cl.
*A61N 1/05* (2006.01)
*A61N 1/08* (2006.01)
(Continued)

(52) U.S. Cl.
CPC ............. *A61N 1/05* (2013.01); *A61N 1/0553* (2013.01); *A61N 1/08* (2013.01); *H01L 24/19* (2013.01);
(Continued)

(58) Field of Classification Search
CPC .......... A61N 1/05; A61N 1/08; A61N 1/0553; H01L 24/19; H01L 24/20;
(Continued)

(56) References Cited

U.S. PATENT DOCUMENTS 4,441,498 A * 4/1984 Nordling ............ A61N 1/37229
128/903
6,304,784 B1 10/2001 Allee et al.
(Continued)

FOREIGN PATENT DOCUMENTS

EP 1883107 A2 1/2008
WO 20080080073 A3 8/2008
(Continued)

OTHER PUBLICATIONS

Bulcke, et al., "Active Electrode Arrays By chip Embedding in a Flexible Silicone Carrier, 28th IEEE EMBS Annual International Conference", Aug. 30, 2006.
(Continued)

*Primary Examiner* — Mark Bockelman
(74) *Attorney, Agent, or Firm* — Howard & Howard Attorneys PLLC

(57) ABSTRACT

An implantable electrode array is provided that includes a carrier that is flexible. At least one control module is coupled to the carrier. A shell encases the control module. At least one electrode is coupled to the carrier and is electrically connected to the control module.

22 Claims, 67 Drawing Sheets

Related U.S. Application Data division of application No. 14/045,914, filed on Oct. 4, 2013, now Pat. No. 9,770,582, which is a division of application No. 13/364,973, filed on Feb. 2, 2012, now Pat. No. 8,554,340, which is a continuation of application No. PCT/US2010/044401, filed on Aug. 4, 2010, which is a continuation-in-part of application No. 12/535,717, filed on Aug. 5, 2009, now Pat. No. 8,781,600.

(51) Int. Cl.
  *H01L 23/00* (2006.01)
  *H05K 1/18* (2006.01)
  *H05K 1/11* (2006.01)

(52) U.S. Cl.
  CPC .... *H01L 24/20* (2013.01); *H01L 2224/04105* (2013.01); *H01L 2224/2101* (2013.01); *H01L 2224/211* (2013.01); *H01L 2224/215* (2013.01); *H01L 2224/221* (2013.01); *H01L 2224/24227* (2013.01); *H01L 2924/014* (2013.01); *H01L 2924/01005* (2013.01); *H01L 2924/01006* (2013.01); *H01L 2924/01023* (2013.01); *H01L 2924/01033* (2013.01); *H01L 2924/01075* (2013.01); *H01L 2924/01077* (2013.01); *H01L 2924/01078* (2013.01); *H01L 2924/01079* (2013.01); *H01L 2924/01082* (2013.01); *H01L 2924/09701* (2013.01); *H01L 2924/12042* (2013.01); *H01L 2924/15153* (2013.01); *H01L 2924/15165* (2013.01); *H01L 2924/15787* (2013.01); *H05K 1/118* (2013.01); *H05K 1/185* (2013.01)

(58) Field of Classification Search
  CPC . H01L 2224/24227; H01L 2924/12042; H01L 2924/15787; H01L 2224/215; H01L 2224/221; H01L 2224/211; H01L 2224/2101; H01L 2924/01077; H01L 2924/01075; H01L 2924/014; H01L 2924/01078; H01L 2924/01033; H01L 2924/01023; H01L 2924/01006; H01L 2924/01005; H01L 2224/04105; H01L 2924/01082; H01L 2924/01079; H01L 2924/15165; H01L 2924/09701; H01L 2924/15153; H05K 1/118; H05K 1/185
  See application file for complete search history.

(56) References Cited

U.S. PATENT DOCUMENTS

| | | | |
|---|---|---|---|
| 7,218,971 | B2 | 5/2007 | Heil et al. |
| 7,706,887 | B2 * | 4/2010 | Tai .................. B81C 1/0023 257/678 |
| 7,742,817 | B2 * | 6/2010 | Malinowski ........ A61N 1/025 607/36 |
| 8,554,340 | B2 | 10/2013 | Janik et al. |
| 8,781,600 | B2 | 7/2014 | Janik et al. |
| 9,770,582 | B2 | 9/2017 | Brindley et al. |
| 9,950,154 | B2 | 4/2018 | Brindley et al. |
| 2002/0128700 | A1 | 9/2002 | Cross, Jr. |
| 2006/0287660 | A1 | 12/2006 | Syed et al. |
| 2007/0207569 | A1 | 9/2007 | Greenberg et al. |
| 2008/0288037 | A1 | 11/2008 | Neysmith et al. |
| 2009/0124965 | A1 | 5/2009 | Greenberg et al. |
| 2009/0293270 | A1 | 12/2009 | Brindley et al. |
| 2011/0077660 | A1 | 3/2011 | Janik et al. |
| 2012/0022551 | A1 | 1/2012 | Staunton et al. |
| 2012/0330393 | A1 | 12/2012 | Janik et al. |

FOREIGN PATENT DOCUMENTS

| | | |
|---|---|---|
| WO | 2009018172 A2 | 2/2009 |
| WO | 20090111142 A2 | 9/2009 |
| WO | 2009155084 A1 | 12/2009 |
| WO | 2010114998 A1 | 10/2010 |
| WO | 2011017426 A2 | 2/2011 |

OTHER PUBLICATIONS

European Patent Office, "ISA Search Report and Written Opinion for PCT App. No. PCT/US2010/044401", dated Aug. 29, 2011.
European Patent Office, "Partial Search Report for PCT/US2010/044401, Feb. 2011", dated Feb. 9, 2011.

* cited by examiner

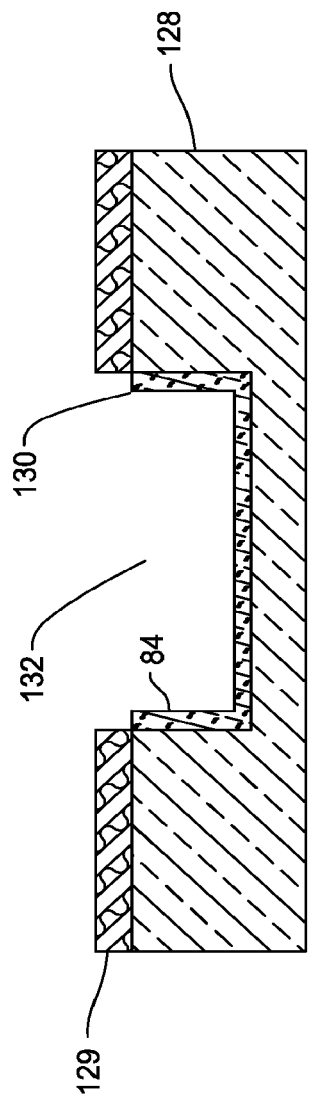
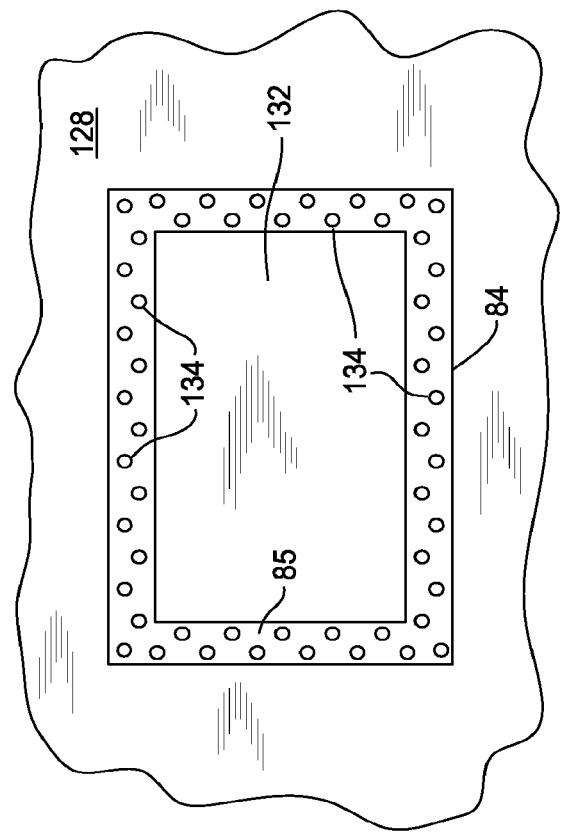

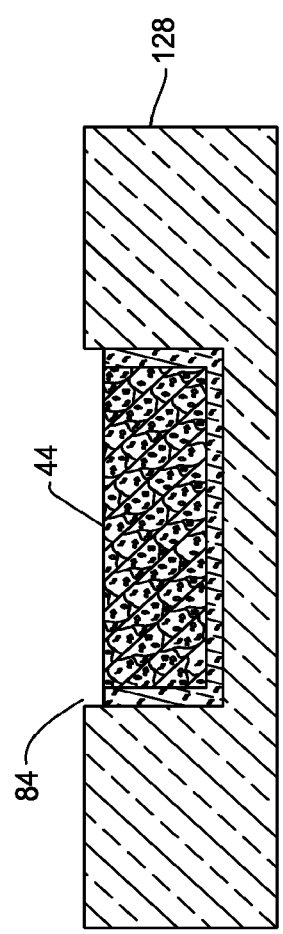
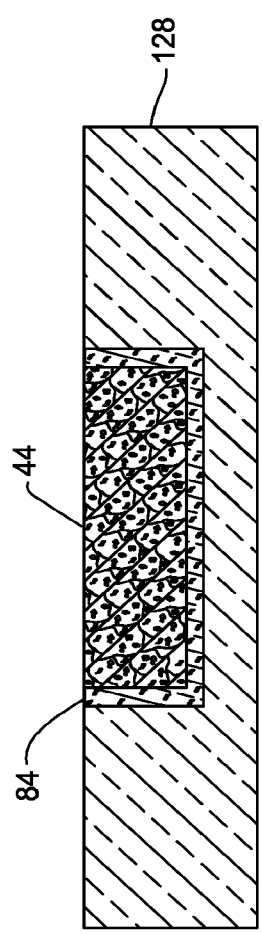

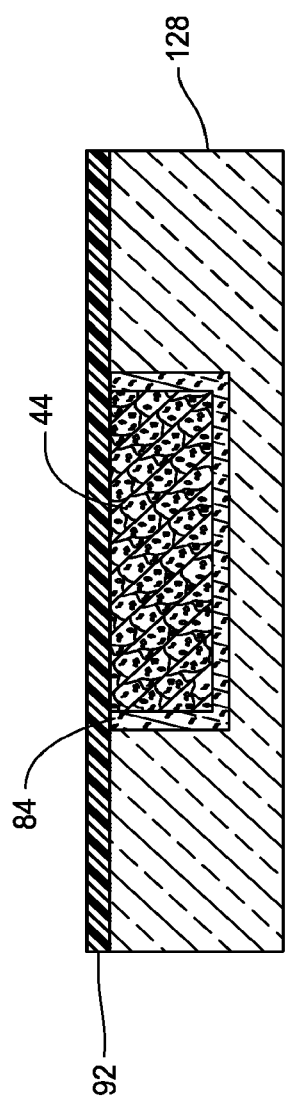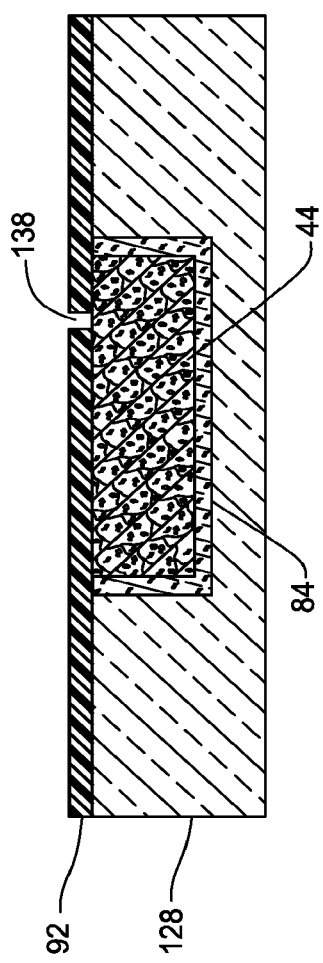

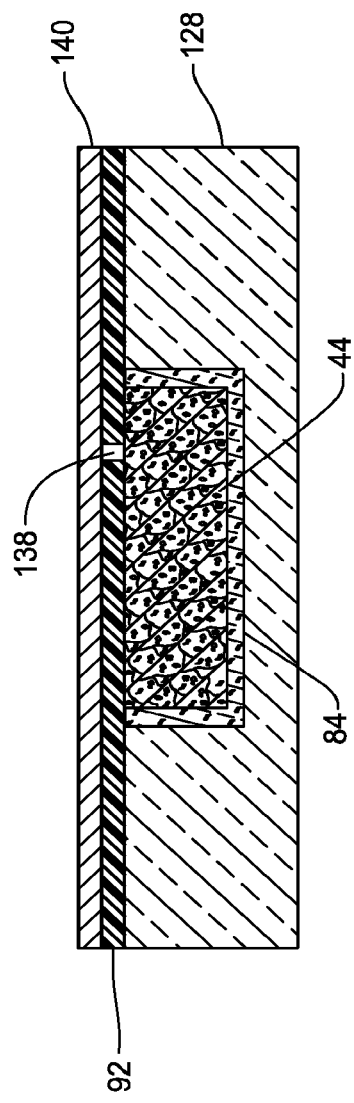
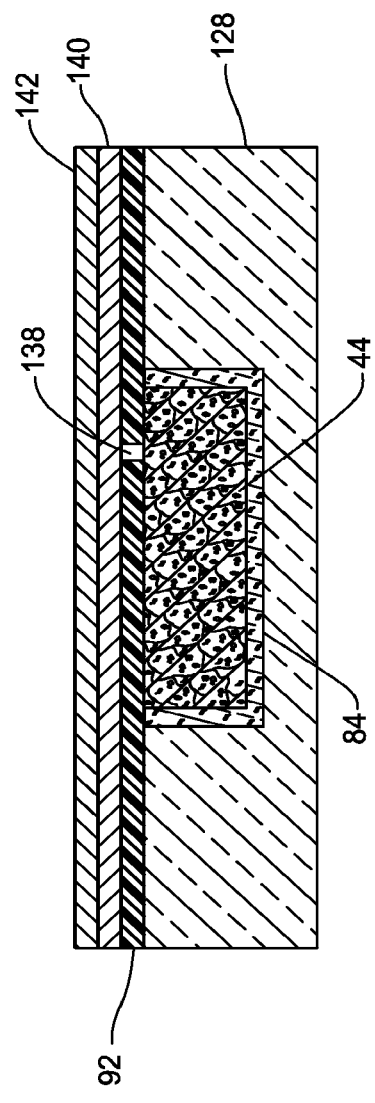

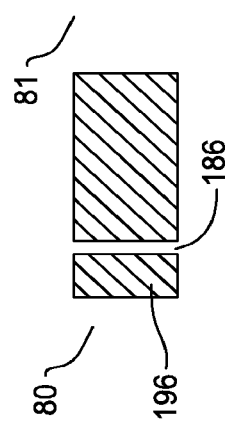
FIG. 27
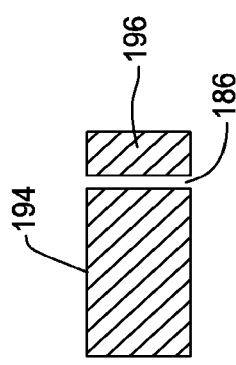
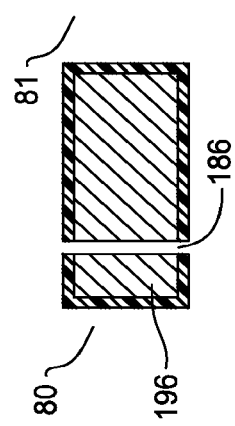
FIG. 28
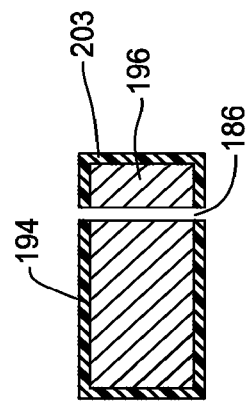

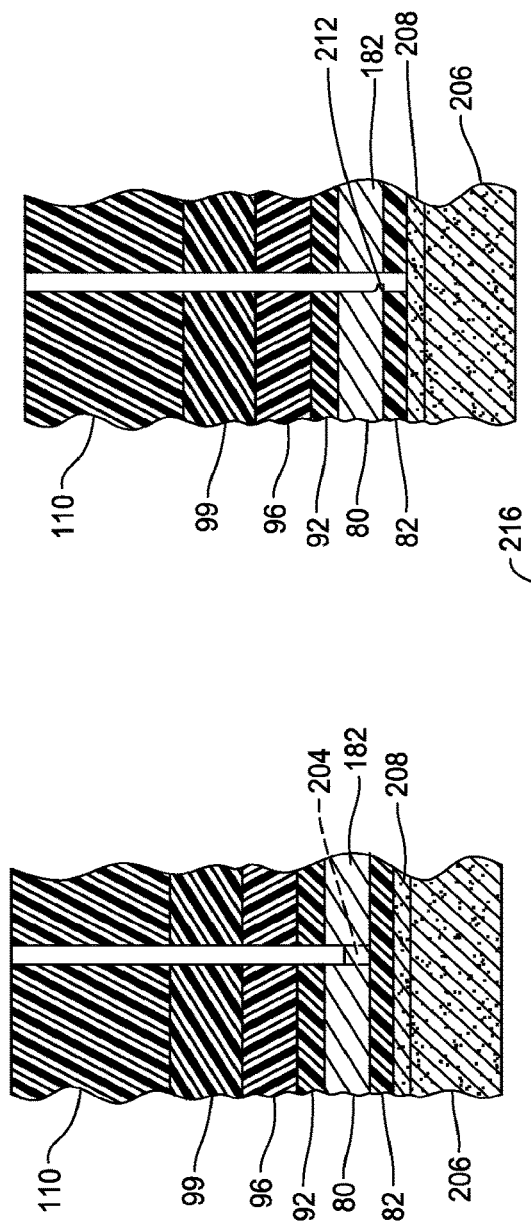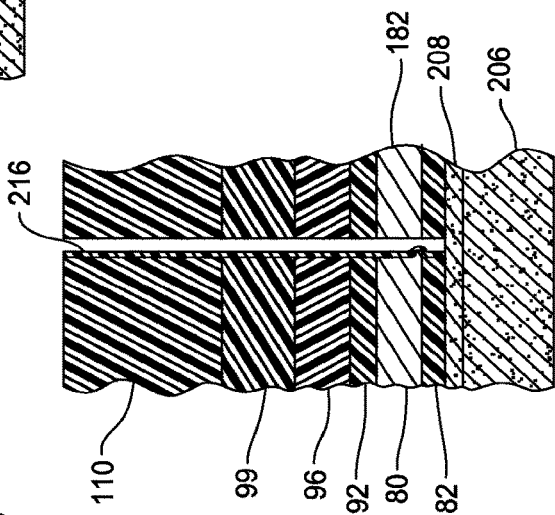

IMPLANTABLE ELECTRODE ARRAY ASSEMBLY INCLUDING A CARRIER WITH PACKAGED CONTROL MODULES

CROSS-REFERENCE TO RELATED APPLICATIONS

This application is a Continuation of application Ser. No. 15/713,291 filed on Sep. 22, 2017. Application Ser. No. 15/713,291 is a Division of application Ser. No. 14/045,914 filed on Oct. 4, 2013, now U.S. Pat. No. 9,770,582. Application Ser. No. 14/045,914 is a Division of application Ser. No. 13/364,973 filed Feb. 2, 2012, now U.S. Pat. No. 8,554,340. Application Ser. No. 13/364,973 is a Continuation of PCT/US2010/044401 filed on Aug. 4, 2010. Application PCT/US2010/044401 is a continuation-in-part of U.S. patent application Ser. No. 12/535,717 filed Aug. 5, 2009 now U.S. Pat. No. 8,781,600. The contents of the above applications are explicitly incorporated herein by reference.

FIELD OF THE INVENTION

This invention relates generally to an implantable electrode array assembly and, more particularly, to an implantable electrode array assembly with one or more control modules for regulating the operation of the assembly embedded in the carrier that supports the electrodes.

BACKGROUND OF THE INVENTION

There are a number of medical conditions for which it has been found that an effective therapy involves driving current through a section of the tissue of a patient. Often, the current is driven between the electrodes of an electrode array implanted in the patient. Generally, the electrode array includes a non-conductive carrier on which typically two or more electrodes are disposed. Once the electrode array is implanted, current is driven from at least one of the electrodes, through the adjacent tissue, to at least one of the other electrodes. The current flow through the tissue influences the tissue to accomplish a desired therapeutic result. For example, an electrode array positioned adjacent the heart may flow currents to stimulate the appropriate contraction and expansion of the heart muscles.

There is an increasing interest in implanting electrode arrays adjacent neural tissue so that the resultant current flow induces a desired neurological or physical effect. In one known application, the current driven between the electrodes of an array placed on top of the dura in the vertebral column reduces the extent to which chronic pain signals are perceived by the brain. Alternatively, the array may be placed in a location where the current flow stimulates a feeling of satiation as part of an appetite suppression/weight management therapy. In another application, the current is flowed to tissue or nerves associated with the bladder or the anal sphincter to assist in control of incontinence. Electrodes may be implanted in a paralysis victim to provide muscle control and/or a sense of feeling.

The Applicants' PCT Patent Application No. PCT/US2009/33769, FOLDABLE, IMPLANTABLE ELECTRODE ARRAY ASSEMBLY AND TOOL FOR IMPLANTING SAME, filed 11 Feb. 2009, published as WO 2009/11142, the contents of which are explicitly incorporated herein by reference, describes an electrode array that includes a carrier on which plural electrodes are arranged in a row by column matrix. An advantage of this electrode array is that it allows current to be flowed between numerous different combinations of electrodes. Depending on which electrodes are connected to associated current sources and sinks, this array can be operated so that there are two or more current flows occurring simultaneously between different sets of electrodes. Once this assembly is deployed, the practitioner can initially drive current between different combinations of electrodes. Current therefore flows through different sections of tissue. This allows the practitioner to determine between which electrodes, through which tissue, the current flow offers the greatest benefit and/or tolerable side effects. Once the optimal current flow path between the electrodes is determined, the array and its associated power supply are set to operate in this state.

The Applicants' PCT Patent Application METHOD OF ASSEMBLING AN ELECTRODE ARRAY THAT INCLUDES A PLASTICALLY DEFORMABLE CARRIER, filed 29 May 2009, published as PCT Pub. No. WO 2009/155084, the contents of which are explicitly incorporated herein by reference, describes a means of batch assembling the above-described electrode array.

In comparison to other electrode arrays with lesser numbers of electrodes, the above-described array makes it possible to flow current through more sections of tissue and to selectively focus/diffuse the current flow. In contrast to an electrode array with a smaller number of electrodes, use of the above-described array increases the likelihood that the current flow can be set to provide desired therapeutic effects, with tolerable side effects.

Still another advantage of the above-described array is that the carrier is formed from superelastic material. A superelastic material is one that, after being subjected to appreciable bending or folding, returns to its initial state. Thus, once this electrode array is formed, the assembly is then folded or rolled into a form that has a side-to-side width appreciably less than its width in the unfolded/unrolled state. A benefit of an electrode array assembly of this design is that it can be folded into a sheath. The sheath-encased electrode array assembly can then be inserted through an access cannula using a minimally invasive procedure into the patient. Once in the patient, the sheath and assembly are steered to over the tissue against which the electrodes integral with the assembly are deployed. Once the assembly is properly positioned, the sheath is opened up or removed. The opening/removal of the sheath causes the carrier to unfold. As a consequence of the carrier unfolding, the electrodes deploy over the target tissue. A more complete understanding of how the electrode array assembly can be so positioned and deployed is contained in the Applicants' Assignee's PCT App. No. PCT/US2010/029628, DELIVERY ASSEMBLY FOR PERCUTANEOUSLY DELIVERING AND DEPLOYING AN ELECTRODE ARRAY AT A TARGET LOCATION, THE ASSEMBLY CAPABLE OF STEERING THE ELECTRODE ARRAY TO THE TARGET LOCATION, which is explicitly incorporated herein by reference the contents of which are published in US Pat. Pub. No. US 2012/0022551 A1.

Thus, not only does an electrode array built on a superelastic carrier provide a means for selectively flowing current through different sections of tissue, the assembly can be placed over the target tissue without having to cut a large incision in the patient.

One feature of the above-described array is that also mounted to the carrier are one or more drive modules. The drive modules contain the components that source/sink the current to/from the electrodes. It is necessary to provide some on array control circuitry because the array typically includes 10 or more and often 20 or more electrodes each of which serve as a current source and/or sink. Without providing these modules, it would be necessary to implant a large number of conductors that extend from the pulse generator, through the patient, over which the current is sourced/sunk to the individual electrodes. Physical constraints make it difficult to implant large numbers of conductors in the patient. The above referenced applications described how an electrode array may be constructed so that the drive module is disposed on the surface of the array on which the electrodes are disposed; the surface of the assembly disposed against the tissue. Alternatively, the drive module may be positioned on the surface of the carrier opposite the surface that faces the tissue.

Regardless of the location on the surface of the carrier on which the drive module is located, it is necessary to encase the module in some sort of package. The package protects the semi-conductor die forming the drive module. Often the package includes a shell and a cap. The shell surrounds one end and the sides of the die. The cap covers the exposed end of the array and the perimeter of the shell. Consequently, the known assemblies have some sort of conductors that extend from the electrodes, through the package to the semiconductor die. As mentioned above, a significant feature of the known assembly is that the carrier has some degree of flexibility. Accordingly, the conductors disposed on the carrier of this assembly are subjected to some flexing. Inside the package, the conductors are held rigid. Accordingly around the perimeter of the package, where the conductors are stopped from flexing, the conductors may be subjected to considerable stress. There is a concern that this stress could induce failure in the conductors.

Moreover, inside the package, wire bonds may have to be used to establish the final connections between the conductors and the complementary bond pads on the control module-forming semiconductor die. These wire bonds, given the fragility of the wires from which they are formed, may also be prone to breakage. In regard to this matter is should be appreciated that once electrode array assembly is implanted, the assembly, like the patient in which it is implanted, is almost always moving. Over time, the vibration induced by this movement can potentially cause these wire bonds to fracture. Clearly, the failure of these wire bonds, or complementary conductors can result in malfunction of electrode array.

SUMMARY OF THE INVENTION

This invention is related to a new and useful electrode array designed for implantation into a living being. The electrode array of this invention includes one or more control modules that are built into the array so as to minimize the extent to which the conductors that extend to the module/modules are subjected to breakage-inducing stress.

The electrode array of this invention includes a carrier. Typically the carrier is formed out of material that is at least flexible so that the carrier at least conforms to the tissue against which the array is deployed. Often the carrier is formed from material that, in addition to being flexible, has some degree of elasticity. This allows the electrode array assembly to be deployed using minimally invasive surgical techniques.

The electrode array of this invention also includes one or more control modules. A control module is a semiconductor die. The components fabricated on the control module source/sink current to one or more of the electrodes. Each control module is seated in a window or a recess formed in carrier. In many versions of the invention, a layer of biocompatible material surrounds one or more of the exposed faces of the control module to serve as a partial package around the module. Insulating material that has some degree of flexibility is disposed over the exposed surfaces of the carrier and adjacent exposed surfaces of the module/modules. Vias extend through the insulating material to complementary bond pads on the control module/modules. Some of the vias extend to the individual electrodes. Other ones of the vias extend to conductors also part of the array. These conductors, and the vias to which they are connected, function as the conductive members through which power and/or operating instructions that originate off the array are applied to the control module/modules.

In some versions of the invention, a control module is associated with each electrode. The control module may be seated in a window or other opening in the carrier so as to be below the electrode.

The vias and conductors of the electrode array of this invention are primarily disposed on or extend through layers of material that has some degree of flexibility. The vias themselves are relatively short in length. The conductors to which the vias extend are thin both in their height and width. These dimensional features of the vias and on-array conductors improve their flexibility. Collectively, the flexibility of these components, the insulating material, the vias and the conductors, reduces the extent to which the mechanical stress to which the vias and conductors are exposed can cause their breakage.

BRIEF DESCRIPTION OF THE DRAWINGS

The invention is pointed out with particularity in the claims. The above and further features and advantages of this invention are better understood from the below Detailed Description taken in conjunction with the accompanying drawings in which:

FIGS. 5 and 6 are cross sectional view depicting initial steps of the fabrication of an electrode array assembly on a support substrate;

FIG. 7 is a top plan view of a partially fabricated control module shell of the electrode array assembly;

FIGS. 8-25 are a sequence of cross sectional views depicting the fabrication how an electrode and associated control module of an electrode array are, according to this invention, fabricated on a wafer;

FIGS. 27 and 28 are cross sectional views depicting how the carrier is prepared for bonding to a substrate;

FIGS. 34-36 are cross sectional views depicting the steps executed to separate the electrode array carrier from the adjacent section of the coupon to which the carrier was connected;

DETAILED DESCRIPTION

I. Electrode Array Assembly

Figure 1:
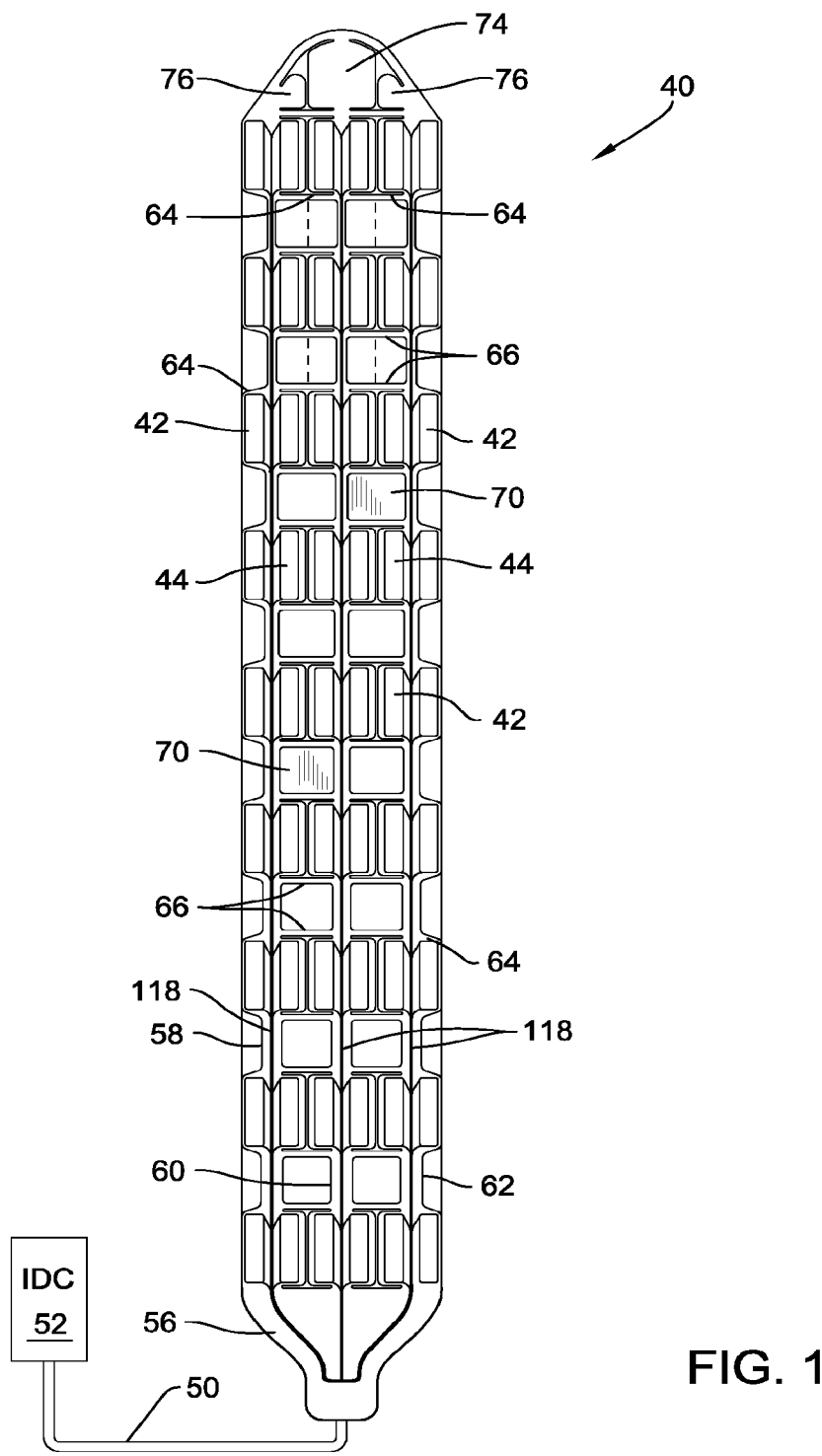
FIG. 1 is plan view of an electrode array assembly of this invention.
Figure 1A:
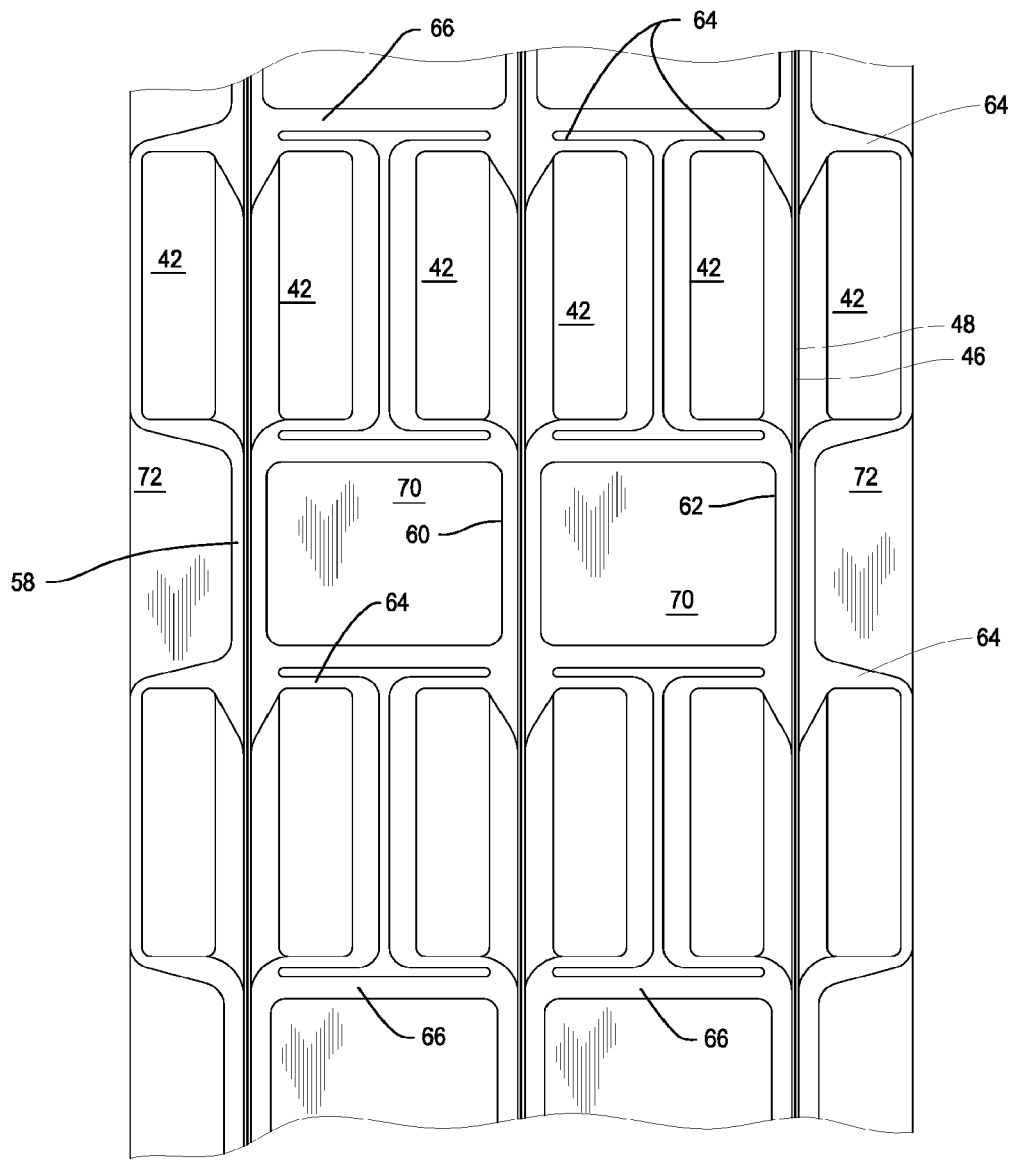
FIG. 1A is an enlarged view of a section of the electrode array of FIG. 1.
Figure 2:
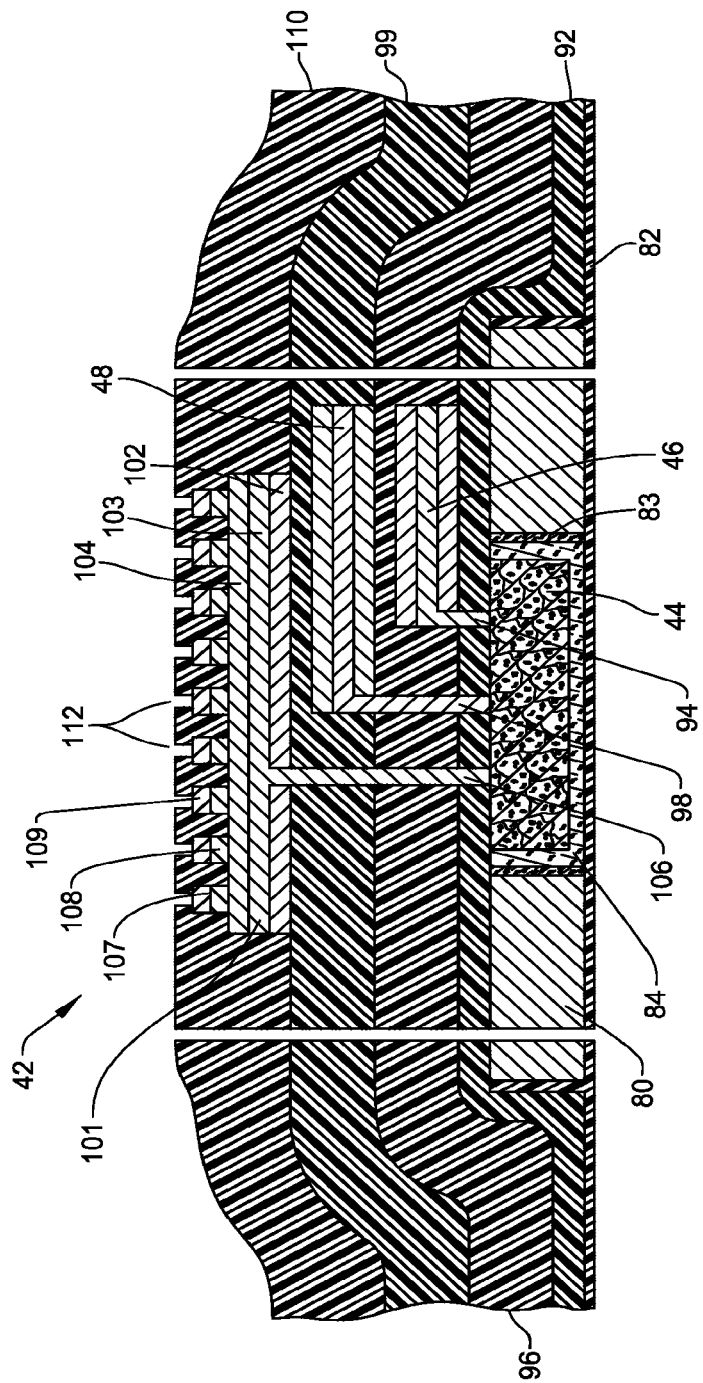
FIG. 2 is a cross sectional view of a portion of the electrode array assembly showing a single electrode and the control module associated with that electrode.

FIGS. 1, 1A and 2 illustrate an electrode array 40 of this invention. Electrode array 40 includes a number of individual electrodes 42 depicted in outline as a number of rectangles in FIGS. 1 and 1A. Associated with each electrode 42 is a control module 44. Each control module 44 is an application specific integrated circuit (ASIC) that includes components able to source current from/sink current to the associated electrode 42. Conductors 46 and 48 extend from the control modules 44. Conductors 46 and 48 are connected to a cable 50 that extends from the proximal end of the electrode array assembly 40. Not illustrated are the individual conductors internal to cable 50. Cable 50 is connected to an implantable device controller (IDC) 52. The IDC 52 contains the power source for the currents that are flowed between the electrodes 42. IDC 52 also contains a controller that generates the instructions that indicate between which electrodes 42 the currents are to be flowed. The specific structure of the IDC 52 is not part of the present invention.

Electrode array assembly 40 is shaped to have a base 56 that is the most proximal portion of the assembly. (Here, "proximal" means towards the end of the assembly at the bottom of FIG. 1; "distal" means towards the end of the assembly at the top of FIG. 1). Three parallel, spaced apart bridges 58, 60 and 62 extend distally forward from base 56. The outer two bridges, bridges 58 and 62, extend forward from the opposed sides of base 56.

Plural tabs 64 extend outwardly from each bridge 58, 60 and 62. More particularly, at a number of spaced apart locations along the length of each bridge 58, 60 and 62, two tabs 64 extend outwardly from the opposed sides of the bridge. At least in the version of the invention depicted in FIGS. 1 and 1A, the tabs 64 are arranged in diametrically opposed pairs relative to the bridge 58, 60 or 62, from which the individual tabs extend. Electrode array assembly 40 is further constructed so that at each longitudinal section on bridge 58 from which tabs extend, tabs 64 also extend from the laterally adjacent longitudinal sections of bridges 60 and 62. Thus, in the illustrated version of the invention, tabs 64 are arranged in rows. In each row of tabs 64, two tabs extend outwardly from each bridge 58, 60 and 62. The rows of tabs 64 are longitudinally spaced apart from each other. In some versions of the invention, the separation between the distal end of one row of tabs and the proximal end of the distally adjacent row of tabs is between 1 to 10 mm. In many versions of the invention, this separation is between 2 and 6 mm.

Each tab 64 is generally in the form of a rectangle with rounded corners. Each tab 64 has a length (measurement along an axis parallel to the longitudinal axis of assembly 40) of between 0.5 to 5 mm. Often this length is between 2 and 4 mm. Each tab 64 has a width, (measurement along the axis perpendicular to the longitudinal axis of assembly 40 in the plane of FIG. 2) of 0.25 to 2 mm. In many versions of the invention, this width is between 0.5 to 1 mm. It should further be understood that each tab 64 attached to one bridge 58 or 60 is separate from the adjacent tab 64 attached to the adjacent bridge 60 or 62. The spacing between the adjacent tabs 64 extending from adjacent bridges is typically no more than 500 microns and preferably 100 microns or less. This small separation between adjacent tabs 64 reduces the amount of tissue that can grow between the tabs. If appreciable tissue were allowed to grow between the tabs 64, this tissue could inhibit later removal of the assembly 40.

Beams 66 extend between the bridges 58, 60, and 62. More particularly, each beam 66 extends between adjacent bridges 58 and 60 or between adjacent bridges 60 and 62. In the illustrated version of the invention, assembly 40 is further constructed so that each beam 66 connecting bridges 58 and 60 is collinear with an adjacent beam connecting bridges 60 and 62. Each beam 66 has a width, (measurement along an axis parallel to the longitudinal axis of the assembly 40) of approximately 0.25 mm.

The electrode array assembly 40 of FIG. 1 is further constructed so that there is a pair of collinear beams 66 adjacent the proximal and distal ends of each of the tabs 64 in each row of tabs. Thus, in the illustrated version of the invention 16 pairs of beams connected the spaced apart bridges 58, 60, and 62 together.

Given the spacing between the tabs 64, it should be appreciated that the longitudinally adjacent pairs of beams 66 are spaced apart from each other along the longitudinal axis of electrode array assembly 40. As discussed below, a flexible membrane 70 is disposed between these adjacent spaced apart beams 66. In FIG. 1A some membranes 70 are shown by surface shading. Similarly, membranes 72, located on the outer sides of bridges 58 and 62. Each membrane 72 extends between a pair of longitudinally adjacent tabs 64 that extend from the outer sides of bridges 58 and 62. Membranes 70 and 72 are present to inhibit tissue growth between the features of the electrode array 40.

Electrode array 40 is also formed to have a head 74 and two shoulders 76. Head 74 is located forward center-located bridge 60. Each shoulder 76 extends forward from one of the two outer located bridges 58 or 62. Shoulders 76, while connected to head 70 by narrow beams, (beams not identified) are generally spaced apart from head 74. A more complete discussion of the geometry of the assembly head 74 and shoulders 76 is contained in the incorporated by reference U.S. Pat. App. No. 61/166,366.

An electrode 42 is disposed on each one of the tabs 64. The associated control module 44 is likewise seated, embedded in, the tab 64. Conductors 46 and 48 extend from each tab to the adjacent bridge 58, 60 or 62. If an electrode 42 does not function as a current source or sink, the electrode may function as a voltage probe. When an electrode 42 performs this function, the associated conductors 46 and 48 serve as the conductors over which the sensed voltage is connected to a monitoring circuit (not illustrated and not part of this invention).

By reference to FIG. 2 it can be seen that electrode array assembly 40 has a carrier 80 formed from a superelastic material; that is, a material that, after being subjected to the strain induced by appreciable rolling, folding or bending, returns to its initial shape. In one version of the invention, the carrier 80 is formed from a nickel titanium alloy such as Nitinol. Carrier 80 is shaped to form the basic geometric features of the assembly including base 56, bridges 58, 60 and 62, tabs 64, beams 66, head 74 and shoulders 76. Membranes 70 and 72 are formed from material different from which the carrier 80 is formed. In FIG. 2, electrode array assembly is shown active side up. The "active" side is the side of the array 40 on which electrodes 42 are exposed. Opposite the active side, electrode array 40 has a "passive" side, shown as the bottom side in FIG. 2.

Figure 26:
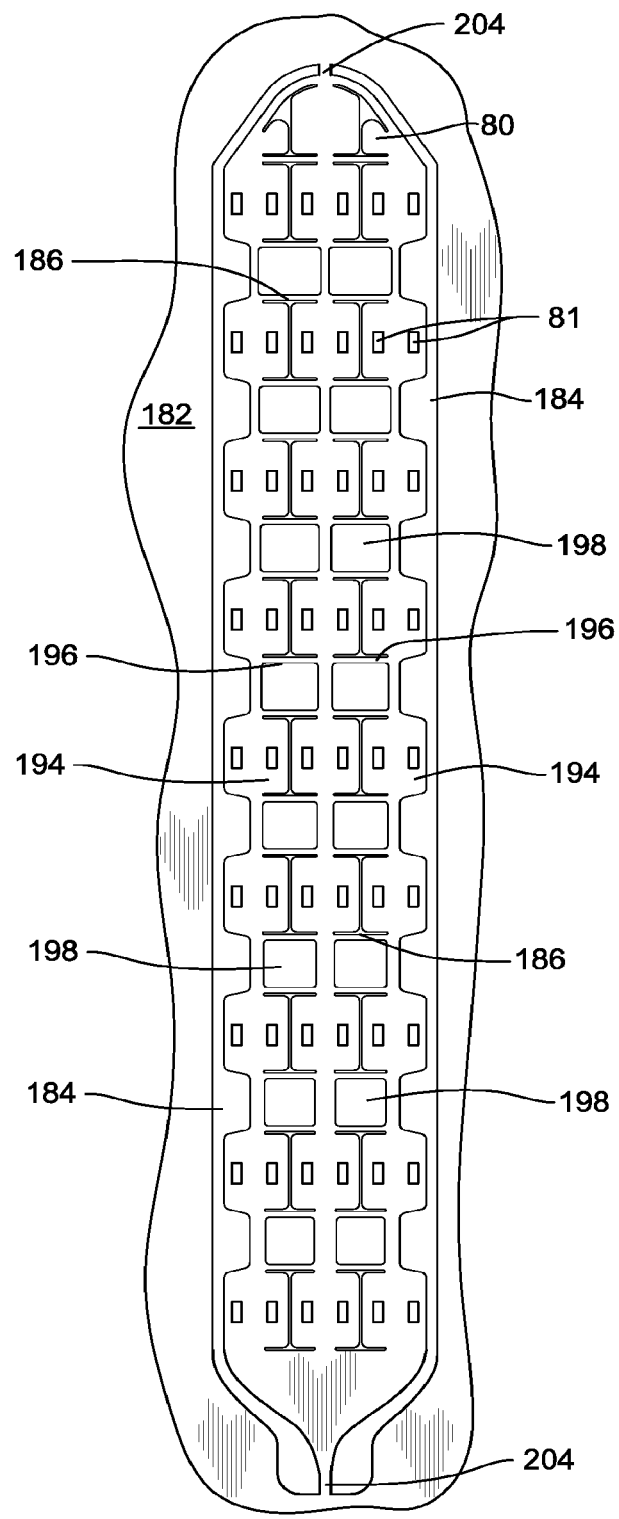
FIG. 26 is a plane view of a section of a coupon on which a carrier of this invention is formed.
Figure 26A:
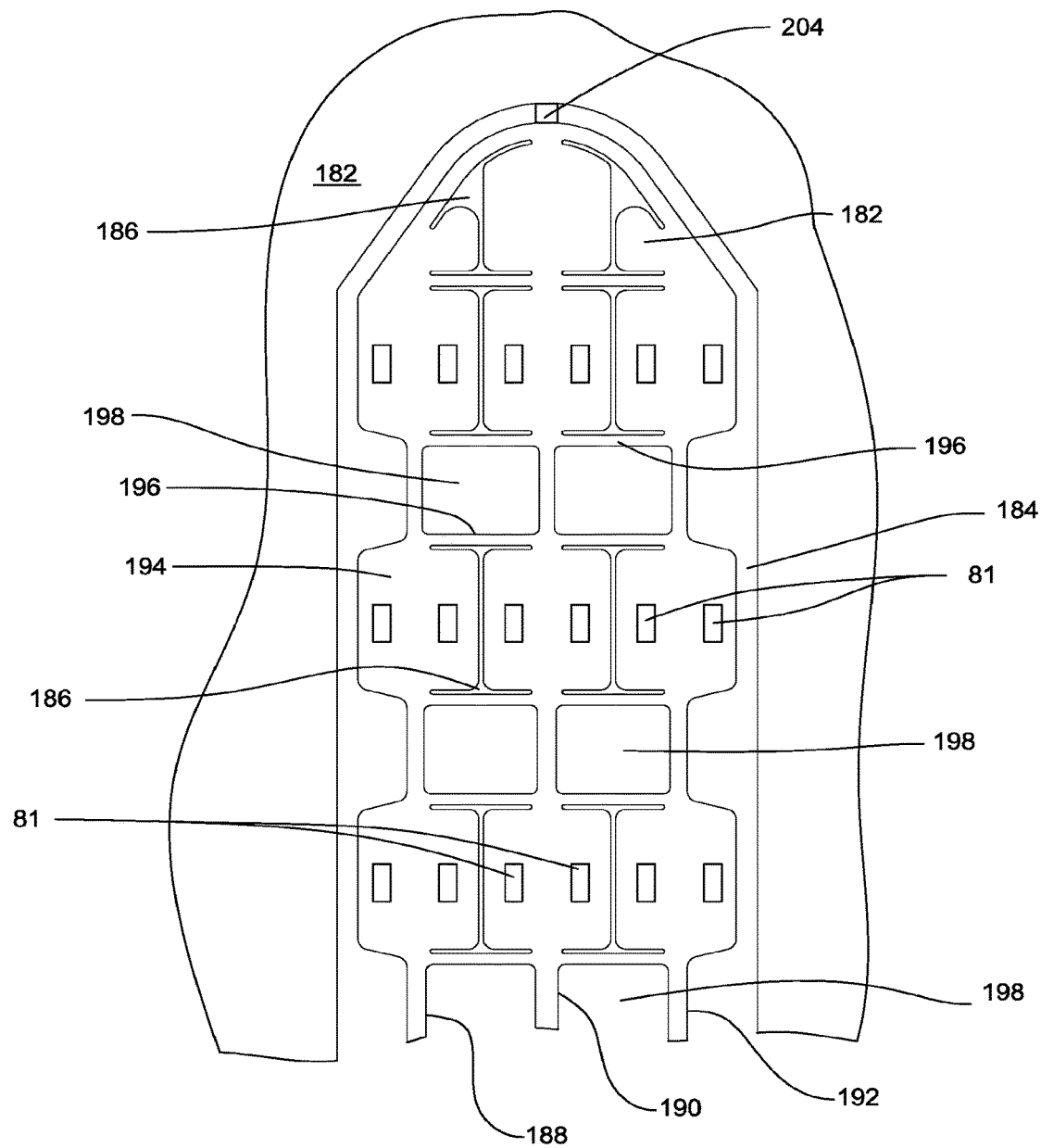
FIG. 26A is an enlarged plan view of the distal end of the carrier of FIG. 26.

Carrier 80 is formed with a number of windows 81, seen best in FIG. 26A. Each window 81 is formed in a separate one of the tab-defining sections of carrier 80. Returning to FIG. 2 it can be seen that frames 83 (one shown) formed from electrically insulating material, are located around the inner surfaces of carrier 80 that define the windows 81. A separate control module 44 is seated in each one of the windows 81 so as to be within the frames 83. The side surfaces of each control module 44 are encased in a shell 84 also formed from electrically insulating material. Shell 84 also has a panel that extends over the face of the control module 44 directed to the passive side of assembly 40. Thus, around the sides of the control module 44 both a section of the frame 83 and a section of the shell 84 separate the side surfaces of the control module from the adjacent surfaces of the carrier 80.

Figure 37:
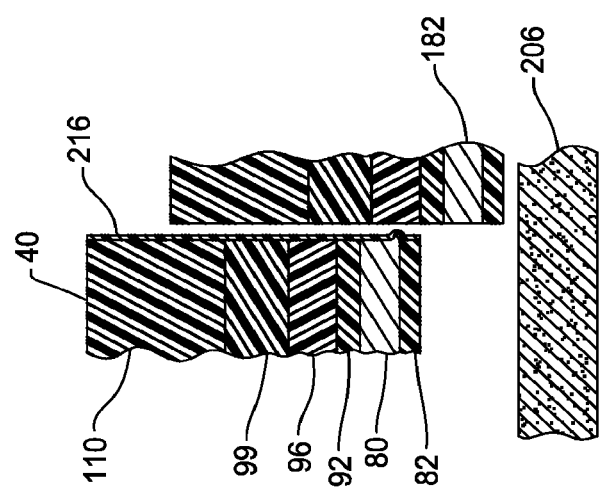
FIG. 37 depicts the lift off, the separation, of the electrode array from the substrate to which the array carrier was bonded.

Insulating material is disposed on the top, bottom and side surfaces of the carrier 80 (side-located insulating material only seen in FIGS. 36 and 37). One such insulating material is a conformal coating such as the polyxylene polymer parylene-C. This insulating material is disposed over the surfaces of the carrier 80. The insulating material disposed over the surface of the passive side of carrier 80, the bottom side in FIG. 2, is identified as passive side insulating layer 82. In addition to covering the passive side face of frame 80, passive side insulating layer 82 extends over the side edges of the carrier 80.

Three different intermediate layers of insulating material, layers 92, 96 and 99 are disposed over the active side of carrier 80. Layers 92, 96 and 99 are formed from parylene. Intermediate insulating layer 92 is applied directly over the active side of carrier 80. Portions of layer 92 thus also cover the active side exposed face of control module 44 and the exposed rectangular carrier faces of the frames 83 and shells 84 that surround the modules 44. Conductors 46 are disposed over the intermediate insulating layer 92. A via 94 extends from conductor 46 through insulating layer 92 to a bond pad 91 (FIG. 7A) formed on the associated control module 44. Intermediate insulating layer 96 is disposed over insulating layer 92 and conductor 46. Conductors 48 are disposed over intermediate insulating layer 96. A via 98 extends from each a bond pad 91 integral with each control module 44 to the conductor 48 associated with that control module 44. In FIG. 2, the individual layers of metal forming conductors 46 and 48 are shown. These layers are described and called out in the illustrated in the sequence of drawings that describe the assembly of electrode array 40 of this invention.

Intermediate insulating layer 99 is the outermost of the three intermediate insulating layers 99. Intermediate insulating layer 99 extends over intermediate insulating layer 96 and conductors 48.

Electrodes 42 are disposed over the intermediate insulating layer 99. Each electrode 42 includes a base pad 101 that is disposed on the outer surface of the intermediate insulating layer 99. Each electrode base pad 101 includes a layer of titanium 102 that is contact with the intermediate insulating layer 99. A layer of gold 103 is disposed over titanium layer 102. A layer of titanium 104 is disposed over the exposed surface of gold layer 103. A via 106, formed of gold, extends from gold layer 103 to a bond pad 91 integral with the associated control module 44. Each via 106 thus extends through the intermediate insulating layers 92, 96 and 99. Spaced apart conductive buttons 107 are disposed over the outer surface of titanium layer 104. Each conductive button 107 includes a titanium layer 108 that is disposed on the base pad titanium layer 104. A thin layer of iridium or iridium oxide 109 is disposed over each titanium layer to complete the conductive button. The exposed faces of the iridium layers 109 of the conductive buttons are the conductive surfaces of each electrode that contact the tissue to which the electrode is applied.

An outer insulating layer, layer 110, is disposed over intermediate insulating layer 99. Outer insulating layer 110 is formed from the same material from which insulating layers 82, 92, 96 and 99 are formed. Outer insulating layer 110 is also disposed over portions of the electrodes 42. More particularly, portions of insulating layer 110 are disposed over the sections of the electrode titanium layer 104 located between the conductive buttons 107. Small sections of insulating layer 110 also surround the outer perimeters of the exposed iridium faces of the buttons 107. Openings 112 in outer insulating layer 110 function as access holes through which the tissue can pass across insulating layer 110 and contact the conductive buttons 107 integral with the electrodes 42.

Often electrode array 40 of this invention will have a thickness, the distance from the exposed face of passive side insulating layer 82 to the exposed face of outer insulating layer 110 of no more than 200 microns. In many cases this thickness is 150 microns or less and in still more preferred versions of the invention, this thickness is 100 microns or less. The side-to-side width across the array 40 is a function of the number of columns of electrodes 42. In the illustrated version of the invention, where there are 6 columns of electrodes 42, the width is typically 15 mm or less and often 10 mm or less. Similarly, the length of the array 40 is a function of the number of rows of electrodes 42. In the version of the invention illustrated in FIG. 1 wherein there are 9 rows of electrodes 42, the top-to-bottom length of the array is 100 mm or less and can be 70 mm or less. In FIG. 2 and the subsequent Figures, the layers of material forming the components of electrode array 40 are not shown to scale unless otherwise stated. This is to facilitate illustration of the components of this invention.

Figure 3:
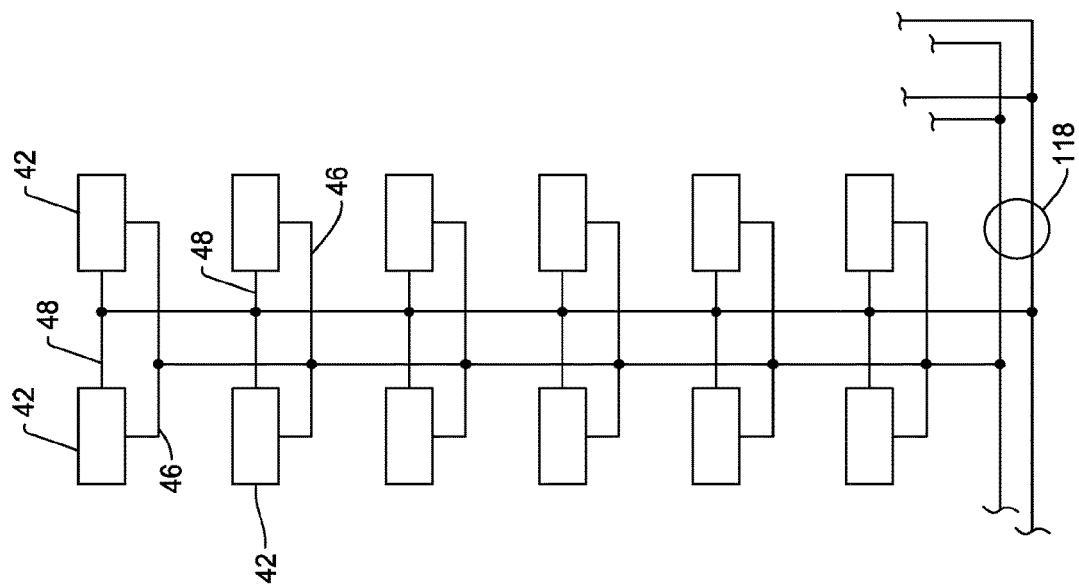
FIG. 3 is a block diagram of how signals are distributed to the individual control modules of the array over a bus.

As seen in FIG. 3, in at least some versions of the invention, each pair of conductors 46 and 48 forms a set of the lowest order branches from a two-wire bus 118. In FIG. 3, the two conductors forming bus 118 are shown as each having three first order branches, only one of which is completely illustrated. This reflects that each one of the first order branches extends over a separate one of the array bridges 58, 60 and 62. The control modules 42 associated with each bridge 58, 60 or 62 are tied to the branch of the bus that extends over the bridge. In FIG. 3 only six pairs of control modules are shown tied to the illustrated branch of bus 118. This is for ease of illustration only.

The exact structure of the control module 42 is not part of this invention and is not illustrated. For purposes of understanding the electrode array 40 of this invention, it should be understood that each control module 42 includes a node controller. One function of the node controller is to provide the physical connection between conductors 46 and 48, and therefore bus 118, and the other components internal to the module. A second function of the node controller is to, based on instructions received over the bus 118 and conductors 46 and 48, selectively actuate the other circuits internal to the control module 42. A power supply circuit harvests and stores the energy contained in the signals transmitted over the bus. The power supply circuit also stores the energy and uses the stored energy to power the other sub-circuits internal to the module 44. Control module 44 also contains a current source and a current sink, both of which are selectively tied to the electrode 42. Control module 44 also includes an analog to digital converter that is also tied to the electrode 42.

Figure 4:
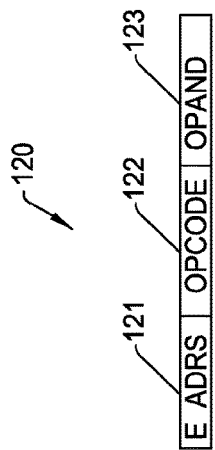
FIG. 4 depicts the components of a control packet distributed over the bus.

FIG. 4 represents the command packet 120 that may be transmitted over the bus 118 to the electrodes 42. One component of the packet 120 is an address field 121 (E ADRS). Address field 121 identifies the individual control module 44 for which the command contained in the packet 120 is intended. An opcode (OPCODE) field 122, also a component of the command packet 120. The opcode field 122 is the specific instruction that is to be taken by the control module 44. Examples of such instructions include: activate current source; activate current sink; and active analog to digital converter so a reading of the voltage present at the electrode may be obtained. Some command packets 120 also include an operand (OPAND) field 123. The operand field 123 contains data indicating the value associated with the operand. An example of a value contained with an operand is the level of the current draw to which the current sink should be set when activated.

The protocol by which signals are transmitted over bus 118 to and from the control modules 44 is not part of the present invention.

In FIGS. 1 and 1A the conductors forming bus 118 appear as lines extending over the array base 56 and bridges 58, 60 and 62. This is for purposes of illustration only. In actually, the bus conductors, like conductors 46 and 48, are covered by insulating layers and are not visible. Also, not illustrated in the Figures are the connections between the on-carrier conductors forming bus 118 and the individual conductors internal to cable 50. This bonding may be achieved by micro-ball bonding.

An electrode array 40 of this invention can be constructed to have 10 or more and even 20 or more electrodes 42 each of which can be individually controlled. An advantage of the array 40 having this number of electrodes is that it allows the practitioner to precisely target through which tissue the current is flowed. This allows the practitioner, often through experimentation, target the current flow through the patient so that the current flow offers an appropriate balance between beneficial effects and tolerable side effects. Even when having this relatively large number of electrodes, the power and commands supplied to the electrodes be supplied over an implanted cable 50 with just two conductors. This minimization of the number of conductors in cable 50 makes it possible to implant the conductors using minimally invasive surgical techniques.

Furthermore, it is anticipated that in many versions of the invention, each control module 44 will function as the current source and sink to no more than eight individual electrodes 42 and more preferably no more than four individual electrodes 42. In the above described version of the invention, each electrode 42 has its own dedicated control module 44. Accordingly, the power source/sink signals generated by each control module typically has to travel a distance of no more than 10 cm usually, often 3 cm or less and more preferably 0.5 cm or less. An advantage of this construction of the invention is that the power required to precisely source/sink currents over these relatively small distances is less the power required to source/sink currents from a device external to the array. Consequently, a portable power source built into the IDC 52 can provide power for a longer time than if the source was required to provide power to individual electrodes spaced 15 cm or more from the IDC 52.

The thin passive side-to-active side profile of array 40 and that the carrier 80 is formed from material that if, not superelastic is at least flexible both facilitate the implantation of the array using minimally invasive medical techniques. For example, prior to implantation the array could be rolled or folded into a cannula having a lumen with a diameter less than the unrolled/unfolded width of the array. The cannula is directed to the target location in the body at which the array is to be deployed. The array is inserted into the body through the cannula. Once the array is discharged from the cannula, the array is unrolled/unfolded over the tissue through which the current is to be flowed.

The parylene forming the layers 92, 96 and 99 through which the vias 94, 98 and 106 extend are flexible. This reduces the mechanical stress to which the vias themselves are exposed. Each via 94, 98 and 106 has a maximum diameter of 80 microns and typically 50 microns in diameter or less. This means that the vias themselves are not so large in cross sectional size that they are not able to themselves flex. The vias themselves are connected directly to the bond pads 91 integral with the control module 44. The need to provide very thin, and therefore very fragile, wire bonds to the control module is eliminated. Further the maximum height of the vias, is typically 100 microns or less and often 50 microns or less. In the version of the array illustrated in FIG. 2, vias 106 are the tallest vias. As a consequence of the vias 95, 98 and 106 being of relatively short height, they are not exposed to large mechanical stresses. Likewise, conductors 46 and 48 and the conductors forming bus 118 have heights that are typically less than 5 microns and often 3 microns or less. The widths across these conductors are usually 75 microns or less and may be 40 microns or less. These design features facilitate the flexibility of these conductors. Collectively, these design features of the electrode array 40 of this invention reduce the likelihood that the mechanical vibrations and shocks to which the array is invariably subjected will so stress these electrical connections that the connections break.

While the parylene layers 92, 96 and 99 the underlying assembly substrate, carrier 80, are flexible, the carrier is less flexible than the parylene layers. The reduced flexibility, increased rigidity, of the carrier is what causes the electrode array assembly 40 to conform to the surface of the tissue against which the assembly is deployed. This feature of the assembly 40 is what holds the assembly electrodes 42 against the tissue to which the therapeutic current is to be applied.

Likewise, even though the array 40 may have 20 or more electrodes 42 it can be possible to provide cable 50 with often four or less and often just two individual conductors over which current is sourced to and instructions are provided to all of the electrodes. This means these conductors, which are not attached to a substrate, may themselves be relatively thick, for example 50 micron or more in diameter and sometimes 100 microns or more in diameter. This facilitates the formation of conductor-to-array bonds with these conductors that are less fragile than the bonds used to hold thinner conductors to the array. This reduction in bond fragility means that it is less likely that, over time, owing to the inevitable mechanical shock to which the array is exposed, one of the bonds will break.

II. First Method of Assembly

Figure 5:
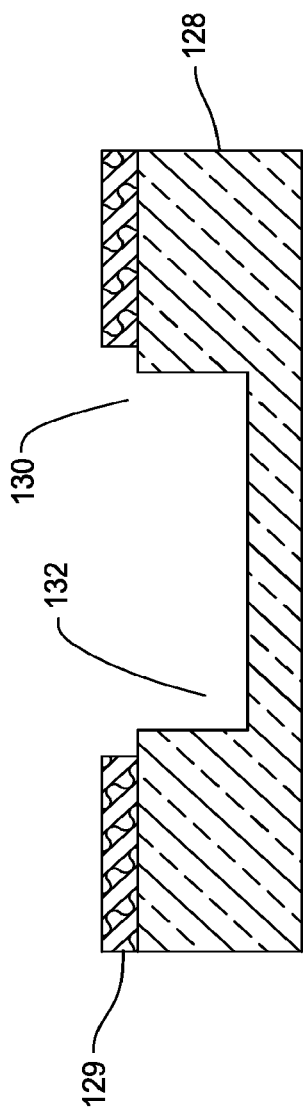

One method of assembling electrode array 40 of this invention is now explained by initial reference to FIG. 5. Initially, a layer of photo resist 129 is disposed over a substrate, here a silicon wafer 128. (Step not illustrated.) Openings 130 (one shown) are formed in the photo resist 129 at the locations where the control modules 44 are to be seated in the silicon wafer 128. Once openings 130 are formed in the photo resist layer 129, using a reactive ion etching process, openings 132 (one shown) are formed in the silicon wafer 128. The openings 132 is formed so that the portions of the wafer 128 that define the openings are located inwardly of the portions of the photo resist 129 that define the perimeter of photo resist openings 132.

As represented by FIG. 6, with photo resist layer 129 still in place, boron is diffused into exposed sections of the silicon wafer 128 that are located inwardly of photo resist openings 130. The boron is diffused approximately 25 microns into the silicon wafer 128. This boron thus diffuses into the portions of the silicon wafer that define the side walls around the bases of wafer openings 132. The boron diffused sections of silicon become the shells 84 (one shown) of assembly 40 and are therefore identified out as such in the Figures. Photo resist layer 129 is then removed from the silicon wafer 128, (step not shown).

Figure 7A:
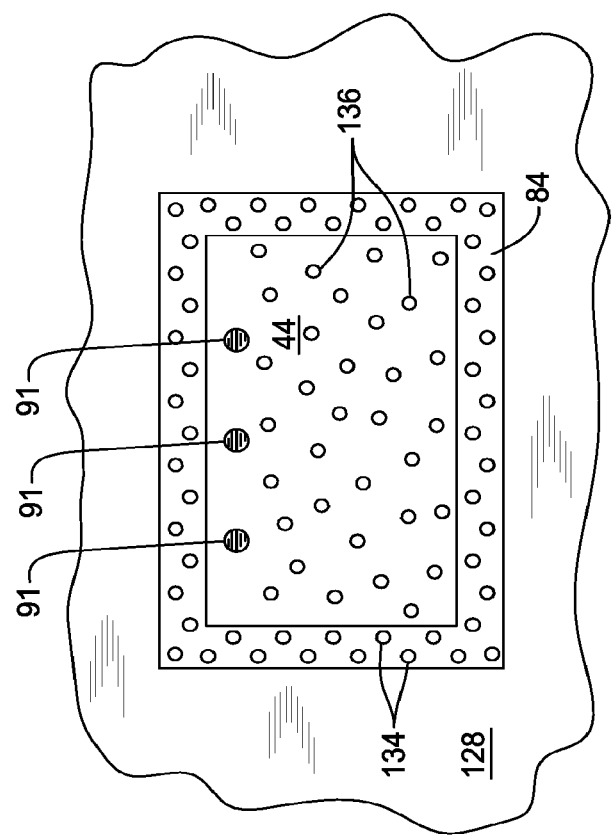
FIG. 7A is a top plan view of control module seated in the shell.

As a consequence of the formation of shells 84, each shell 84 has an exposed face 85, seen in FIG. 7, that is generally in the shape of a rectangular frame. Using a reactive ion etching process, small bores 134 are formed in the exposed faces of the shells 84. Bores 134 have a diameter of approximately 0.2 to 1 micron and extend no greater than 10 microns deep into the shell 84. To minimize the complexity of the later Figures, bores 134 are only illustrated in FIGS. 7 and 7A. It should be appreciated that, in this etching process, as well as in a number of processes in the assembly of electrode array 40, include the sub-steps of applying a photo resist layer, selectively removing portions of the photo resist layer and removing the photo resist layer. Many of these individual sub-steps, as they apply to the formation of bores 134 and other below described processes are neither described nor illustrated.

A control module 44 is then seated in each silicon wafer opening 130 as represented by FIG. 8. The control module 44 is disposed in the shell 44 so that the face of the module on which the bond pads 91 are formed faces outwardly. Control module 44 has a top-to-bottom height that is typically 2 microns or less then the depth of the wafer opening. Accordingly, as represented by FIG. 9, the next step in the assembly of the electrode-control module-conductor subassembly is the removal of the upper sections of the silicon wafer 128 and shells 84 that extend above control modules 44. This removal process is performed by mechanical lapping, removing the outer layers of both the wafer and the shells. As part of the lapping process, the exposed the die, shell and wafer are cleaned. This cleaning step is the only inter-step cleaning step described. Neither this cleaning step nor any of the other cleaning steps are illustrated. This cleaning is performed in part to remove debris from shell bores 134. Uniformity of the levels of the die, the wafer and shell are then checked, step not illustrated.

Small closed end bore holes 136, seen in FIG. 7A, are then formed in the exposed face of the die forming control module 44. Bores 136 have a diameter of between 1 and 2 microns and a depth of no more than 10 microns. Holes 136 are formed by a reactive ion etching process. To minimize the complexity of the drawings, bores 136 are only illustrated in FIG. 7A.

A first insulating layer, intermediate insulating layer 92, is then applied over the coplanar surfaces of the control modules 44, shells 84 and silicon wafer 128, as represented by FIG. 10. Intermediate insulating layer 92 has a thickness of no greater than 20 microns. Parylene is a conformal coating. During the vapor deposition process in which the parylene of intermediate insulating layer 92 is applied, a fraction of the parylene flows into the shell bore 134 and die bores 136. The parylene in bores 134 and 136 holds the parylene forming insulating layer 92 to the surfaces of the dies 44, shells 84 and wafer 128.

During the process of forming intermediate insulating layer 92, the parylene is applied to cover a surface area larger than that subtended by the individual electrodes. The parylene is applied to cover a surface area that typically is greater than the surface area of the electrode array 40. In the subsequent described steps in which insulating layers 82, 96, 99 and 110 are formed, the parylene is similarly applied to cover the same surface area as the parylene forming insulating layer 92. The reason for this relatively wide surface application of the parylene is discussed below.

FIG. 11 illustrates that holes 138 (one shown) are formed in intermediate insulating layer 92. Each hole 138 is in registration over the control module bond pad 91 to which the associated conductor 46 is connected. Holes 138 are formed by, first, applying a photo resist layer over insulating layer 92. Openings are formed in the photo resist layer where the holes 138 are located. An oxygen plasma etching process is used to form the holes 138. Holes 138 have a diameter equal to that of the vias 94 (FIG. 2) that will subsequently be formed in the holes. The photo resist layer is then removed.

Once holes 138 are formed, a layer of titanium 140 is vapor deposited over intermediate insulating layer 92 as represented by FIG. 12. Titanium layer 140 has a thickness of no greater than 5000 Angstroms. The titanium of layer 140 functions as an adhesion layer for the next applied layer 142. Gold is then vapor deposited over titanium layer 140 as seen by FIG. 12 so as to form layer 142. The gold of layer 142 has a thickness of no greater than 5000 Angstroms. The gold of layer 142 functions as a seed layer for the next layer of gold that is of substantially greater thickness.

Figure 20:
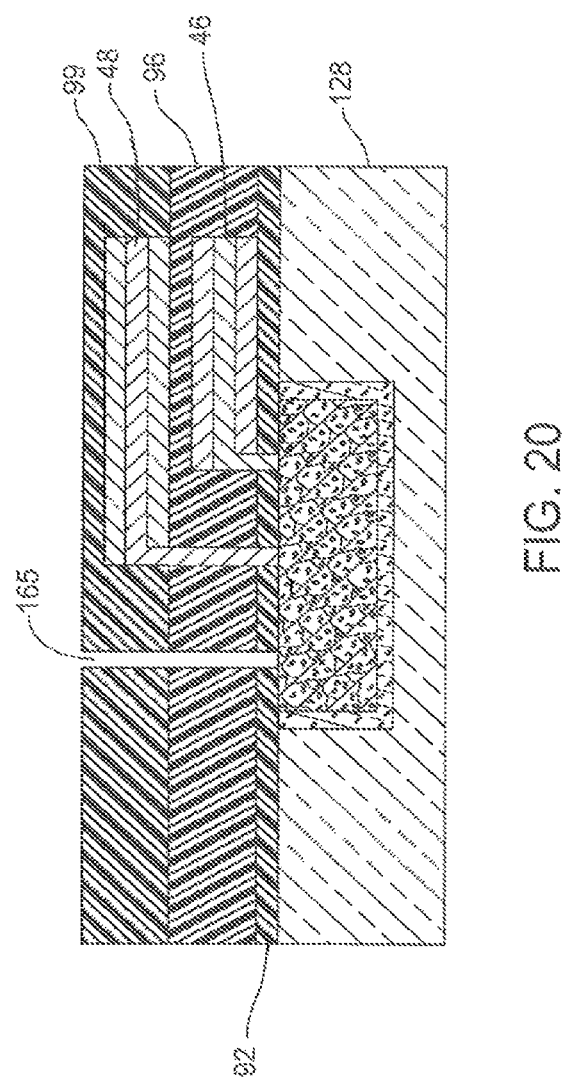

In FIGS. 12 and 13, the titanium of layer 140 and the gold of layer 142 are shown as extending over the hole 138. This is for ease of illustration. In actuality very small amounts of the titanium and gold that, respectively, form layers 140 and 142 flow into the hole 138. The same is true for the titanium adhesion layers and gold seed layers disposed over holes 154 (FIG. 17) and holes 165 (FIG. 20).

Figure 14:
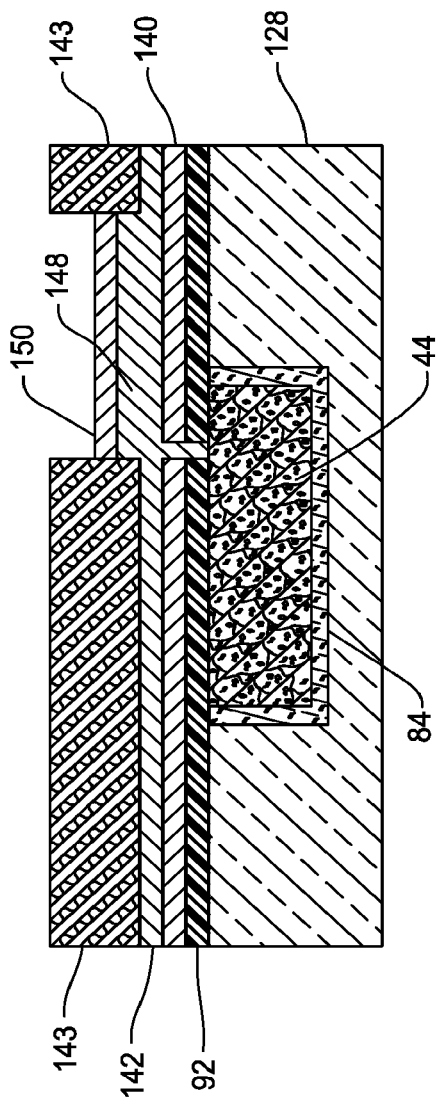

It should be understood that titanium layer 140 and gold layer 142 are deposited over substantially the whole of intermediate insulating layer 92. Fabrication of conductors 46 and the associated conductor of bus 118 continues with the application of a photo resist layer 143 over gold layer 142. Openings are formed in the photo resist layer 143 to expose the sections of the gold layer 142 over which the conductors 46 are to be formed. Gold is applied by an electroplating process over the exposed surfaces of gold layer 142. In FIG. 14 and the subsequent Figures the gold applied over the assembly from these two process form a single layer, called out to the right of the control module 44 in FIG. 14 as layer 148. Layer 148 has a thickness of approximately 2 microns.

As a consequence of the application of the gold forming layer 148 a portion of the gold flows into the openings 138 formed in insulating layer 92. This gold bonds with the underlying control module contact pads 91 so as to form the vias 94 that extend to conductors 46.

Titanium adhesion layer, layer 150 in the Figures, is then applied by a vapor deposition process over the exposed surface of gold layer 148. Titanium adhesion layer 150 typically has a thickness no greater than 5000 Angstroms. While not illustrated, some of the titanium deposited in this process covers the exposed surface of photo resist layer 143.

Photo resist layer 143 is then removed, step not shown. As shown in FIG. 14, photo resist layer 143 extends above titanium adhesion layer 150. Consequently, the photo resist layer 143 can be removed by a chemical lift off process. As a consequence of this process, the titanium deposited on top of the photo resist layer 143 is also transported away from the electrode-control module-conductor assembly. The removal of photo resist layer 143 exposes the portions of the titanium layer 140 and gold seed layer 142 that do not form part of the conductors 46.

Figure 15:
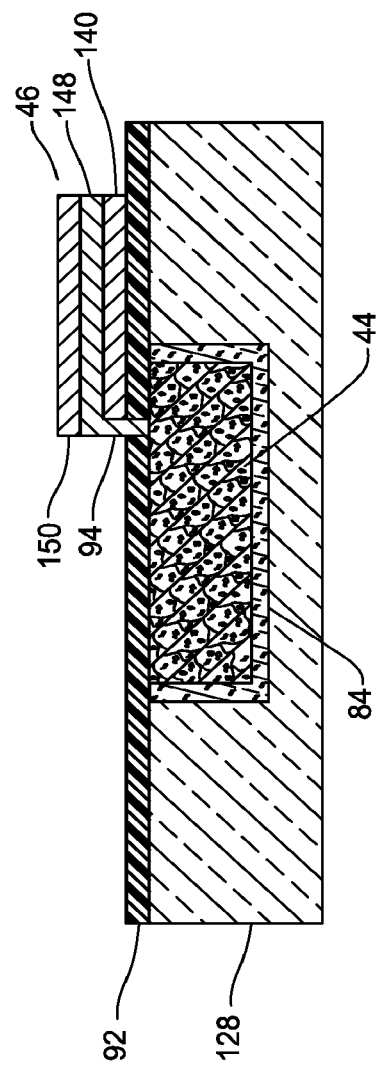

Masks are then deposited over the conductor 46 and the conductor of bus 118, step not shown. A gold-specific chemical etch process is employed to remove the exposed gold seed layer 142. A titanium-specific chemical etch process is then employed to remove the sections of the titanium layer 140 previously covered by the gold seed layer 142. The masks are then removed. As a consequence of the removal of layer 140 and 142, as seen in FIG. 15, what is left on the intermediate insulating layer 92 are sections of laminate that comprise a titanium layer 140 a gold layer 148 and a titanium layer 150. These laminate structures are the conductors 46. Other ones of the laminate structures form the conductors of bus 118.

In FIG. 15 and the subsequent Figures the gold layer 148 of conductor 46 as well as the gold layer 162 of conductor 48 (FIG. 18) and the gold layer 103 of the electrode 42 (FIG. 23) are shown as being of the same thickness as the adjacent titanium layers. This is for ease of illustration only. As indicated by the above stated dimensions, these gold layers are typically at least 4 times larger in thickness than the adjacent titanium layers.

Figure 16:
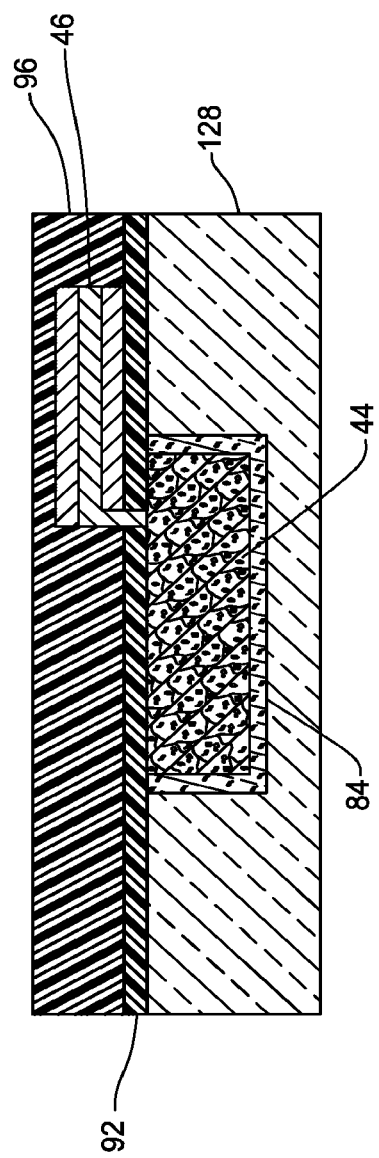
Figure 17:
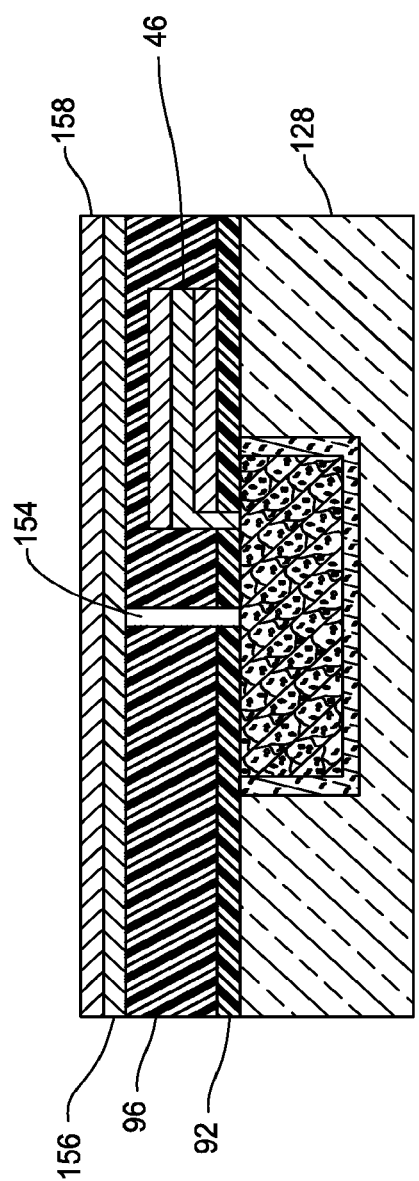

Once conductors 46 and the associated bus conductor are formed, parylene is applied over the conductor 46 as well as intermediate insulating layer 92 to, as illustrated by FIG. 16, forming intermediate insulating layer 96. In regions where the parylene forming insulating layer 96 is applied directly over insulating layer 92, layer 96 has a thickness is typically 10 microns or less. In FIGS. 2 and 16 and in the following Figures, the portion of insulating layer 96 disposed over conductor 46 appears to have a lesser thickness than the portion of layer 96 disposed directly onto layer 92. This is for ease of illustration only. In actuality, the thickness of insulating layer 96 is generally uniform over the different components of the assembly on which the parylene forming the layer is applied. In some versions of the invention layer 96 has a thickness of approximately 10 microns. As seen in FIG. 17, holes 154 (one shown) are formed in intermediate insulating layer 96. Each hole 154 is centered over the die bond pad 91 to which a via 98 extends. Each hole 154 thus extends through both the intermediate insulating layer 96 and the underlying intermediate insulating layer 92. Each hole 154 has the diameter of the via 98 (FIG. 2) that will be subsequently formed in the hole 154.

Figure 18:
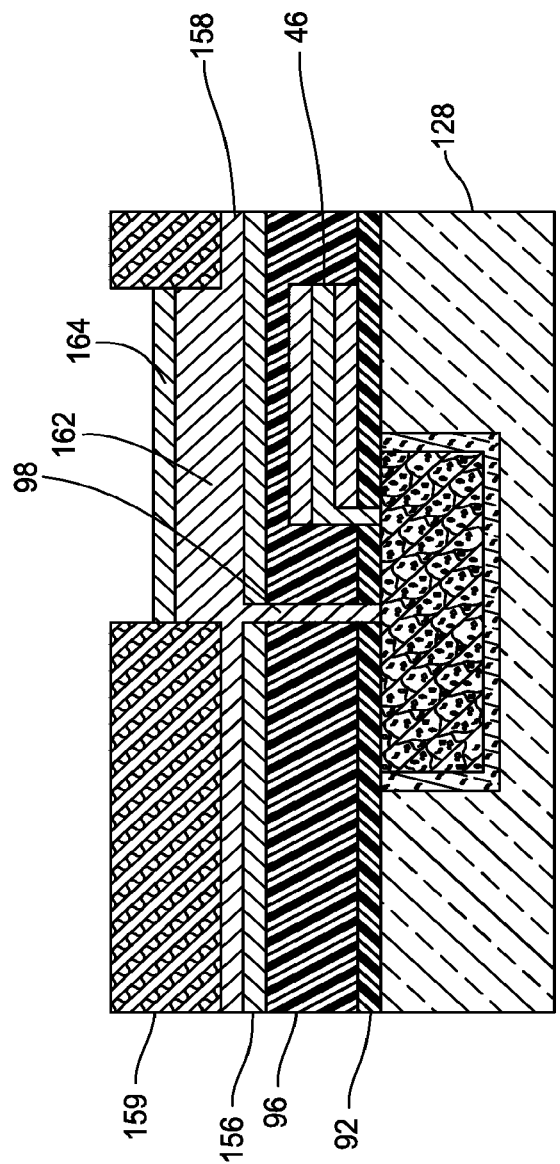
Figure 19:
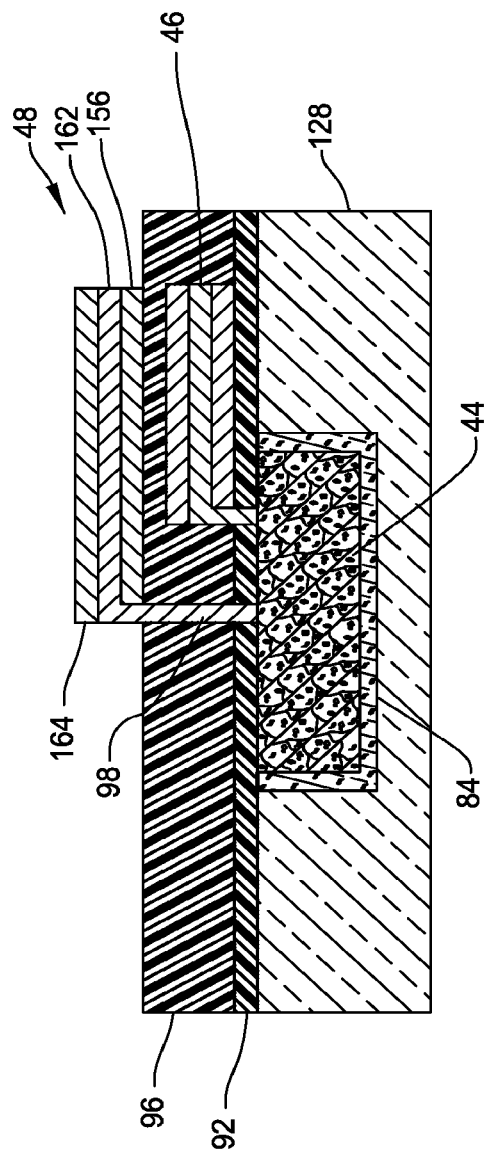

FIGS. 17, 18 and 19 represent that conductors 48 are formed in the same general manner in which conductors 46 are formed. Layers of titanium and gold, respectively layers 156 and 158, are disposed over intermediate insulating layer 96. Not illustrated are small amounts of titanium and gold that form layers 156 and 158 that flow into holes 154. A mask 159 is applied over the surfaces of gold layer 158 that are not to be part of the conductors 48 and associated bus 118 conductor. Gold is electroplated over the sections of gold layer 158 that are open through the mask 159. In FIG. 18 the relatively thick layer of gold formed by this layer and the underlying gold layer 158 is called out as layer 162. A titanium layer 164 is applied on top of gold layer 162. Titanium and gold layers 156, 162 and 164 have the same thicknesses as, respectively, layers 140, 148 and 150.

As a consequence of this electroplating process, gold flows into holes 154 that extend through insulating layers 92 and 96. This gold bonds to the underlying control module contact pad 91 and forms via 96.

Mask 159 is then removed. The sections of first gold layer 158 and then titanium layer 156 previously covered by mask 159 are then removed. These removal processes are the same employed with respect to the removal of layer 140 and 142. As a result of the removal of these sections of layers 156 and 158. The electrode-control module-conductor assembly is left with the conductors 48 and associated bus 118 conductor. In FIG. 19 a single conductor 48, consisting of a laminate of layers 156, 162 and 164 is shown. Again, in FIG. 19 and the other Figures, the relative thickness of these layers is not shown.

The sub-assembly is then prepared for the fabrication of the electrodes 42. As depicted in FIG. 20, this process begins with the application of parylene to establish the outermost intermediate insulating layer, layer 99. Intermediate insulating layer 99 is thus disposed over the conductors 48, the associated bus conductor and the exposed surfaces of intermediate insulating layer 96. Where insulating layer 99 is disposed over insulating layer 96, layer 99 typically has thickness of 10 microns or less. While not apparent in the Figures, insulating layer, the thickness of insulating layer 99 is generally constant regardless of the assembly component over which the parylene forming the layer is applied. Once intermediate insulating layer 99 is formed, holes 165 (one shown) are formed in this layer, as well as underlying insulating layers 96 and 92. Each hole 165 is centered over the die bond pad 91 to which the associated electrode 42 is connected. Each hole 165 has the diameter of the via 106 that is to be subsequently formed in the hole.

Figure 21:
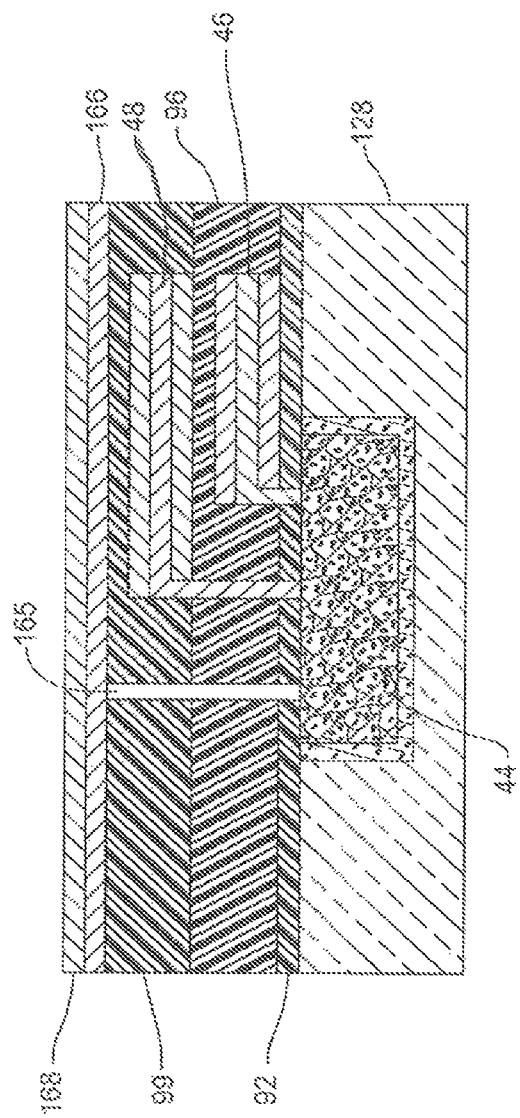

Once intermediate insulating layer 99 is applied to the sub-assembly, titanium and gold seed layers are applied to the assembly by separate vapor deposition processes to facilitate the fabrication of the electrode base pad. FIG. 21 illustrates that these layers, a titanium layer 166 and a gold layer 168 are applied over the whole of insulating layer 99. While not illustrated, a small fraction of the titanium and gold vapor released in this process flows into the holes 165.

Figure 22:
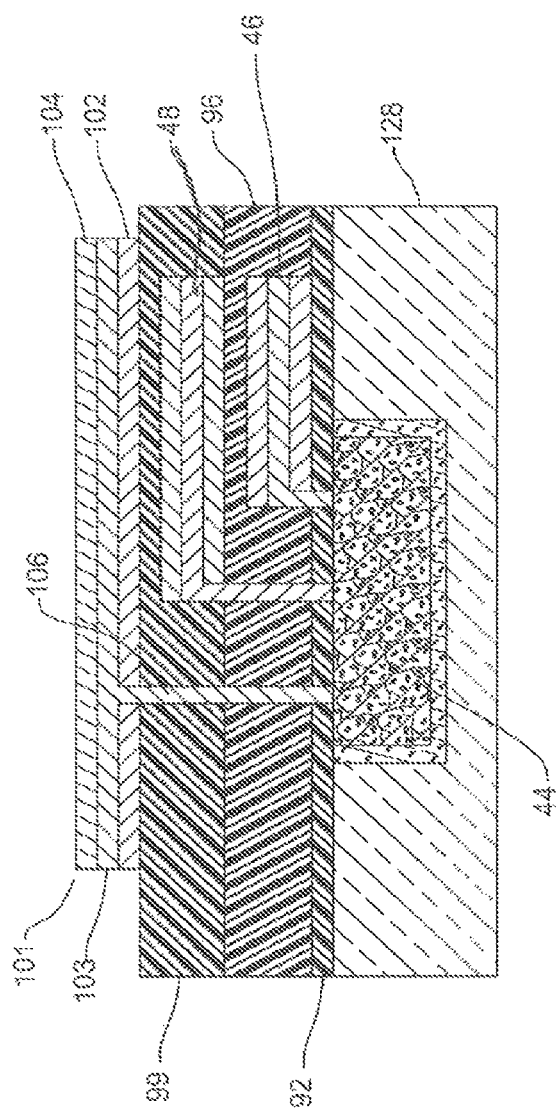

Once titanium layer 166 and gold layer 168 are applied, process steps are performed to increase the thickness of the gold layer and form a titanium adhesion layer adhesion layer on top of the gold layer. These process steps are the same as the process steps used to complete the formation of the conductors 46 and 48 and the conductors integral with bus 118. Accordingly, these steps are neither described nor illustrated. At the conclusion of this process, as seen in FIG. 22, the base pads 101 (one shown) of the electrodes 42 are formed as illustrated in FIG. 22. Titanium layer 102 has a thickness of typically less than 5000 Angstroms. Gold layer 103 has a thickness of approximately 20 microns. Titanium layer 104 has a thickness of typically less than 5000 Angstroms. Gold layer 103 is thicker than gold layers 148 and 164 is to increase the radio-opacity of the electrode array assembly 40 in the vicinity of the electrodes 42.

As part of the electroplating process in which the gold that forms the largest portion of layer 103 is applied, some of the gold flows into holes 165. This gold bonds to the underlying control module contact pad 91 so as to form the control module-to-electrode via 106.

Figure 23:
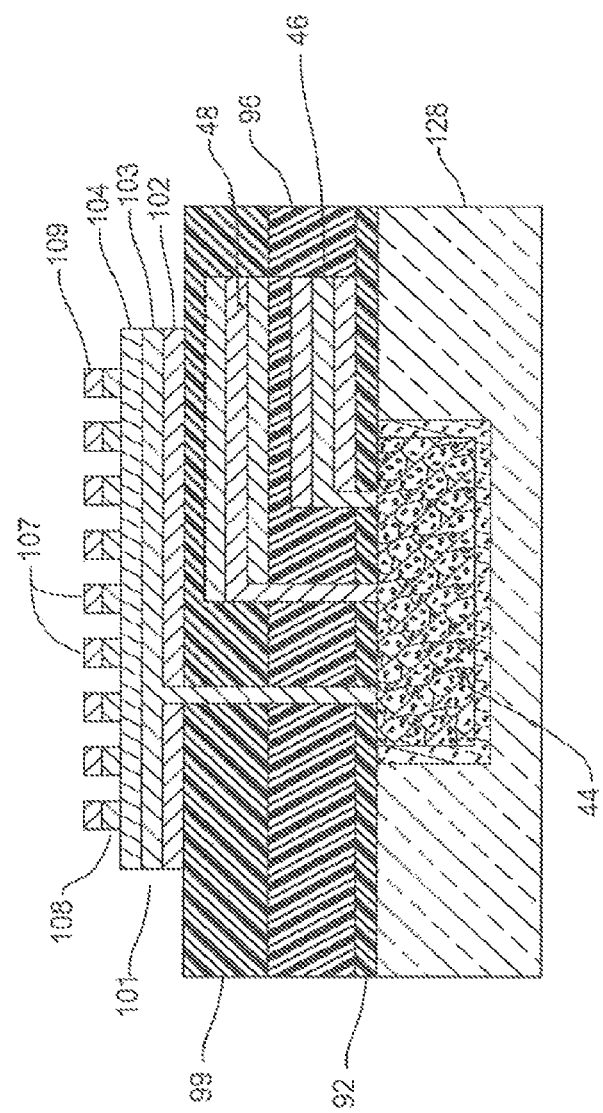

Conductive buttons 107 are then formed over the electrode base pads as seen by reference to FIG. 23. This process begins by the formation of a mask over the exposed titanium layer 104 (step not shown). This mask is formed so as to define openings in the sections of the electrode base pad titanium layers 104 over which the buttons 107 are to be formed. Once the mask is formed, titanium is sputtered over the assembly to form the individual titanium layers 108. Each titanium layer 108 typically has a thickness of less than 5000 Angstroms. Iridium or iridium oxide is then sputtered over the assembly to form button layers 109. Iridium layers 109 often have a thickness of less 30,000 Angstroms and more often less than 10,000 Angstroms. The buttons 107 formed in this process are typically rectangular cross sectional profile. Often the longest length along one of the side edges of a button is 125 microns or less. In some versions of the invention, the longest length along one of these edges is 60 microns or less. The photo resist mask is then removed.

Figure 24:
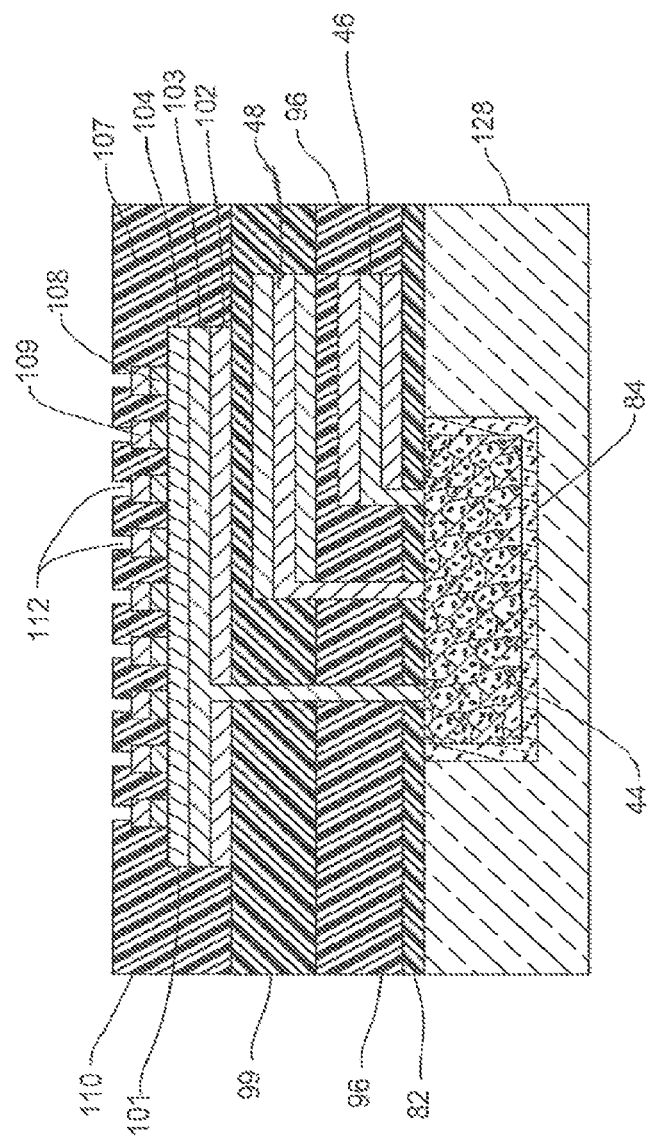

Once the buttons are formed over the electrodes, outer insulating layer 110, is formed over the electrodes. Insulating layer 110, like insulating layers 82, 92, 96 and 99, is a parylene coating. Initially, the parylene forming layer 110 is applied to the whole of the assembly to cover the exposed surfaces of insulating layer 99 as well as the electrodes 42, including the buttons. The parylene forming the portions of insulting layer 110 that extend over insulating layer 99 generally has a thickness of 10 microns or less. While not apparent in the drawings, this thickness is relatively constant, even for the sections of layer 110 disposed over the electrodes 42. Portions of this parylene are selectively removed to forming openings 112 as seen in FIG. 24. In this process, the openings 112 are formed so as to have cross sectional areas that are slightly less than that of the underlying buttons. In other words, the parylene forming outer insulating layer 110 extends around the outer perimeters of the electrode buttons 107. Generally, each opening 112 is formed so as to expose at least 50% of the face of the underlying button 107.

Fabrication of the sub-assembly consisting of the electrodes 42, the control modules 44, conductors 46 and 48 and multiple insulating layers concludes with the separation of the sub-assembly from silicon wafer 128. In one method of this invention, this process is performed by TMAH so as to etch away the silicon forming wafer 128. As seen by reference to FIG. 25, this leaves encased control modules 44 suspended below the laminate structure consisting of the conductors, the insulating layers and the electrodes. This laminate structure can be considered a laminate sheet of insulating material. The control modules 44 are suspended from one side of the sheet, the electrodes 42 are disposed an opposed side of the sheet and the conductors and vias extend through the sheet.

Figure 25:
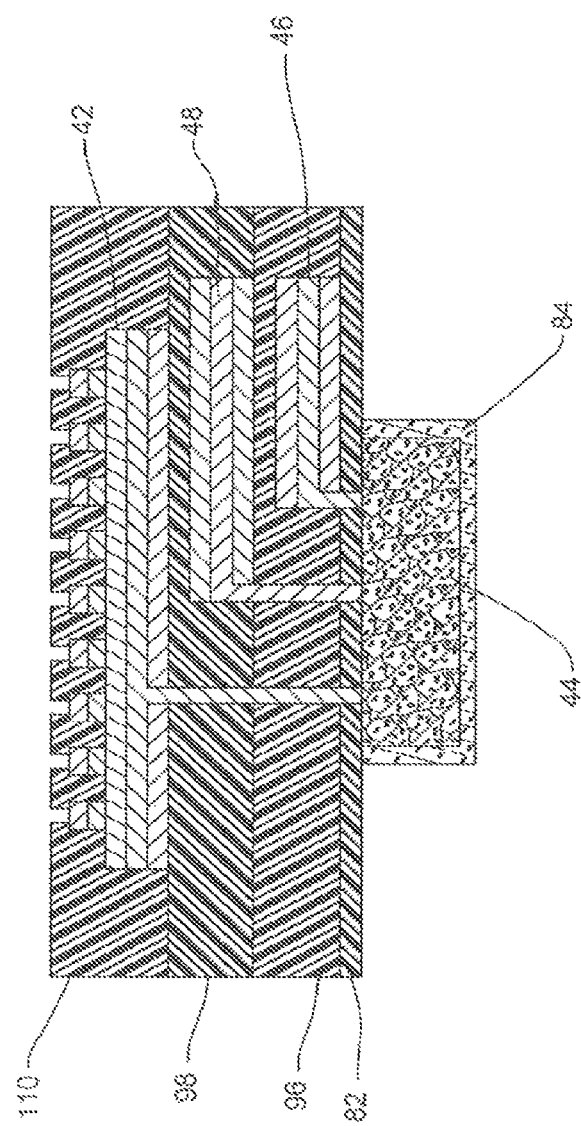

In FIG. 25, only a single electrode 42, a single control module 44 a single pair of conductors 46 and 48 is shown connected to the layers of insulating material. It should be understood that this assembly includes the plural electrodes 42, control modules, conductors 46 and 48 and bus 118 of the electrode array 40.

As part of the presently described method of assembly of this invention, the carrier 80 is prepared to receive the electrode-control module-conductor assembly. This process begins with the basic formation of the carrier which is now described by initial reference to FIGS. 26 and 26A. In the initial steps of the carrier-formation process, a section of a coupon 182 is shaped to define the carrier 80. The coupon 182 is a sheet of the carrier-forming material. In one version of the invention coupon 182 is a sheet of Nitinol that has a thickness of 50 microns. In this process, portions of the coupon 182 are selectively removed to define a set of slots 184 in the coupon that essentially define the whole of the outer perimeter of the carrier 80. Slots 186 and openings 198 are also formed in the coupon so as to define the features of the carrier 80. These features include bridges 188, 190 and 192, that correspond to assembly bridges 58, 60 and 62, respectively. Other features formed in this step are tabs 194 and beams 196 that correspond to assembly tabs 64 and beams 66, respectively. In the Figures, openings 198 are the openings between the adjacent carrier beams 196 that separate the adjacent rows of carrier tabs 194.

Another internal carrier feature formed in this processes are the windows 81 that extend through the carrier-forming section of the coupon 182. Each window 81 is formed so as to be in a location in the carrier 80 in which one of the control modules 44 is mounted. In the illustrated version of the invention, a window 81 is formed in each one of the carrier tabs 194. For reasons apparent below, each window 81 subtends an area that is slightly greater than the area of the occupied by the control module 44 that is to be seated in the window. In one version of the invention, each window 81 is formed so as to allow a separation of approximately 25 microns between the outer surface of the control module shell 84 and the adjacent inner surface of the coupon/carrier section that defines the window. This separation extends around the whole of the perimeter of the shell 84.

In versions of the invention wherein the carrier 80 is formed from Nitinol, these carrier defined features are formed by selectively etching away section of a Nitinol coupon 182. This process is performed by chemical etching.

As mentioned above in the above process, the slots 184 that are formed in the coupon 182 to define the carrier 80 are not formed to completely define the carrier, and therefore completely separate the carrier from the surrounding portion of the coupon. Instead, the coupon 182 is shaped so that small tabs 204 separate the slots 184 so as to connect the carrier-forming section of the coupon with the rest of the coupon 182. In the illustrated version of the invention, two tabs 204 connect the carrier forming section of the coupon with the surrounding section of the coupon. The tabs 204 are located at the opposed longitudinally ends of the carrier forming section of the coupon 182.

In some versions of the invention, the coupon is prepared for the subsequent manufacturing steps by forming the tabs 204 so that the tabs 204 have a thickness that is less than the thickness of the rest of the coupon 182. This process may be performed by an etching process on the sections of the coupon in which the tabs 204 are to be formed so as to only partially remove the material form the forming the coupon 182. In some versions of this invention, this process of partially etching sections of the coupon 182 to form the tabs 204 is performed prior to the step of etching other sections of the coupon to form the carrier defining slots 184 and 186 and openings 198.

While not illustrated, after the carrier 80 is formed on the coupon 182 the carrier may be shaped to develop a shape that is non-planar with respect to the surrounding sections of the coupon 182. For example the carrier of FIGS. 26 and 26A may be bent so as to have arcuate curvature that is perpendicular to the longitudinal axis of the carrier 80. If the carrier 80 is so bent, the lateral side edges of the carrier would thus be above or below the plane of the page on which the carrier of FIG. 26 is presented.

The method of shaping the carrier 80 is a function of the material from which the carrier/coupon is formed. For example, if the carrier/coupon is formed from Nitinol, this shaping may be performed by placing the coupon in a mold in which the carrier is bent appropriately while simultaneously heating the coupon. Under heat, the carrier-defining section of the coupon would develop the desired shape.

FIG. 27 illustrates a longitudinal section through a portion the carrier-defining section of the coupon. Shown in FIG. 27 and subsequent FIGS. 28 and 31-33 is a longitudinal slice through one of the carrier tabs 194, the beams 196 on either side of the tab and a window 81 in the tab.

Once the coupon 182 is formed to define the carrier 80, parylene is coated to the surfaces of the coupon, including the surfaces of the carrier. In FIG. 28 the parylene is shown on the top and bottom faces of the tab 194 and the surfaces of the tab 194 that define window 81. Parylene is also shown on the opposed top and bottom surfaces of the beams 196 and the side surface of the beams 196 directed away from the adjacent tab 194. This parylene is called out as layer 203. Parylene is not shown on the opposed adjacent surfaces of the tab 194 and beams 196 that define the slots 186 between the tab and beams. This omission is for only for ease of illustration. Parylene covers these opposed surfaces. These parylene coatings do not close the gaps between the carrier tabs 194 and bridges 196. As part of this coating process, the parylene is also coated on the sections of the coupon on that do not define the carrier 80.

Figure 29:
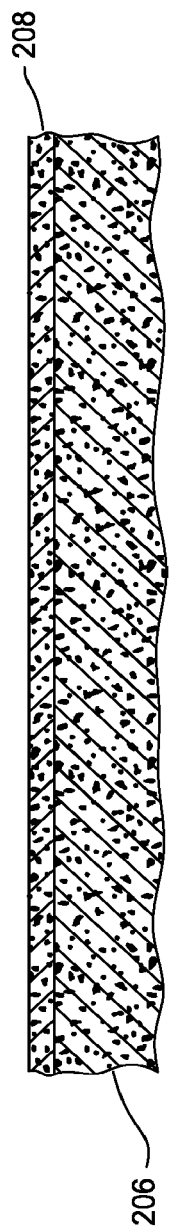
FIGS. 29 and 30 are cross sectional views depicting how the substrate is prepared to receive the carrier.
Figure 30:
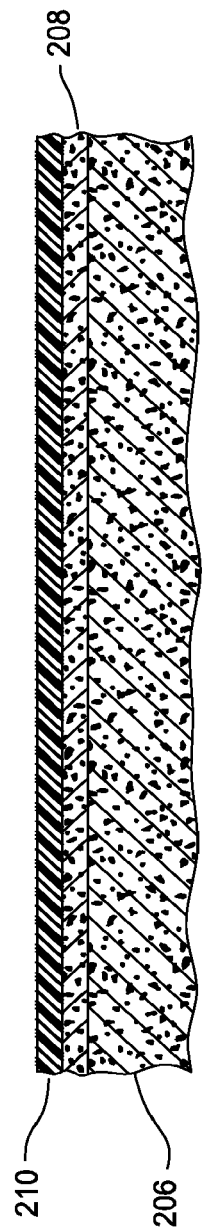

The parylene-coated coupon 182 is then bonded to a rigid substrate 206 now described with respect to FIG. 29. In one version of the invention, substrate 206 is a silicon wafer. Prior to the carrier bonding process, a layer of silicon dioxide 208 is formed on the outer surface of substrate 206. Silicon dioxide layer 208 serves as a sacrificial release layer. A coating of parylene 210, seen in FIG. 30, is applied to the outer surface of the silicon dioxide layer 208.

Figure 31:
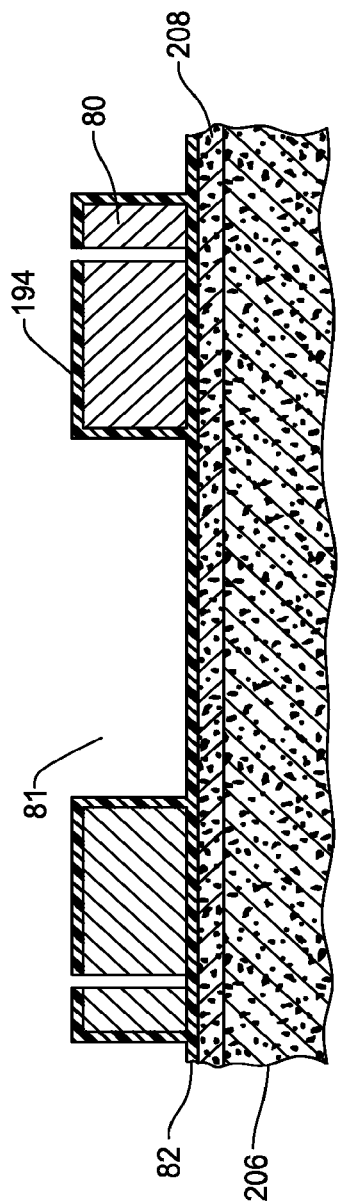
FIGS. 31 and 32 depict how the carrier, once bonded to the substrate, is prepared to receive the electrode-control module-conductor sub-assembly.

FIG. 31 illustrates the bonding of the coupon 182 to the substrate 206. More particularly, in this step, the parylene layer 203 on one the faces of the coupon 182 is bonded to the parylene 210 disposed over the silicon dioxide layer 208. These two parylene layers merge into a single layer that becomes the passive side insulating layer 82 of the electrode array assembly 40. Accordingly, in FIGS. 31-36 this layer is identified as the passive side insulating layer 82.

As described above, some assemblies of this invention may have a carrier 80 that has a non-planar shape. In these versions of the invention, as consequence of the bonding of the carrier-defining coupon 182 to the substrate 206, the carrier 80 is temporarily flexed back into the shape it which the carrier is coplanar with the rest of the coupon 182.

Figure 32:
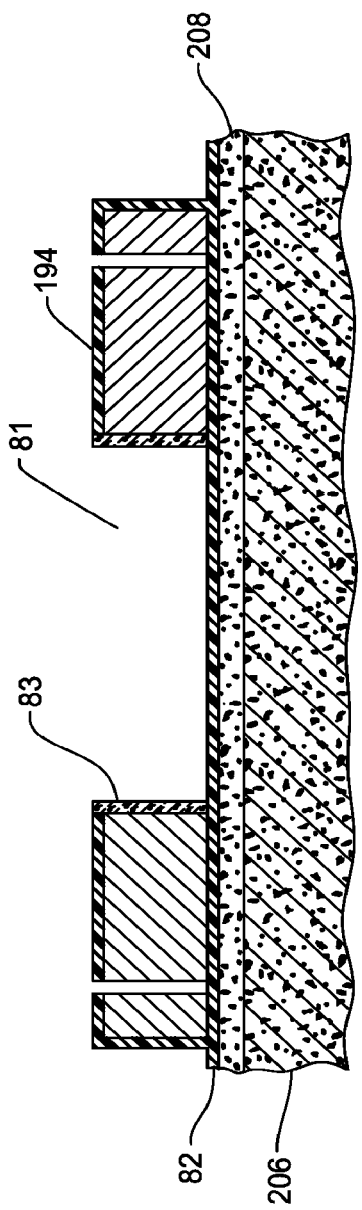

Once the carrier-containing coupon 182 is bonded to the substrate 206, the parylene around the perimeters of the carrier windows 81 is removed, step not shown. The removal of this parylene is performed by reactive ion etching. Once the parylene is removed from around the carrier windows 81, the frame 83 is formed around the surfaces of the carrier that define the windows 81 as seen in FIG. 32. In one version of the invention, the frame 83 is formed by applying a layer of silicon dioxide to the window-defining surfaces using an oxidative deposition process. Alternatively, frame 83 is formed from a polydimethyal silioxane silicon. This type of frame 83 may be applied using an adhesive bonding process.

Figure 33:
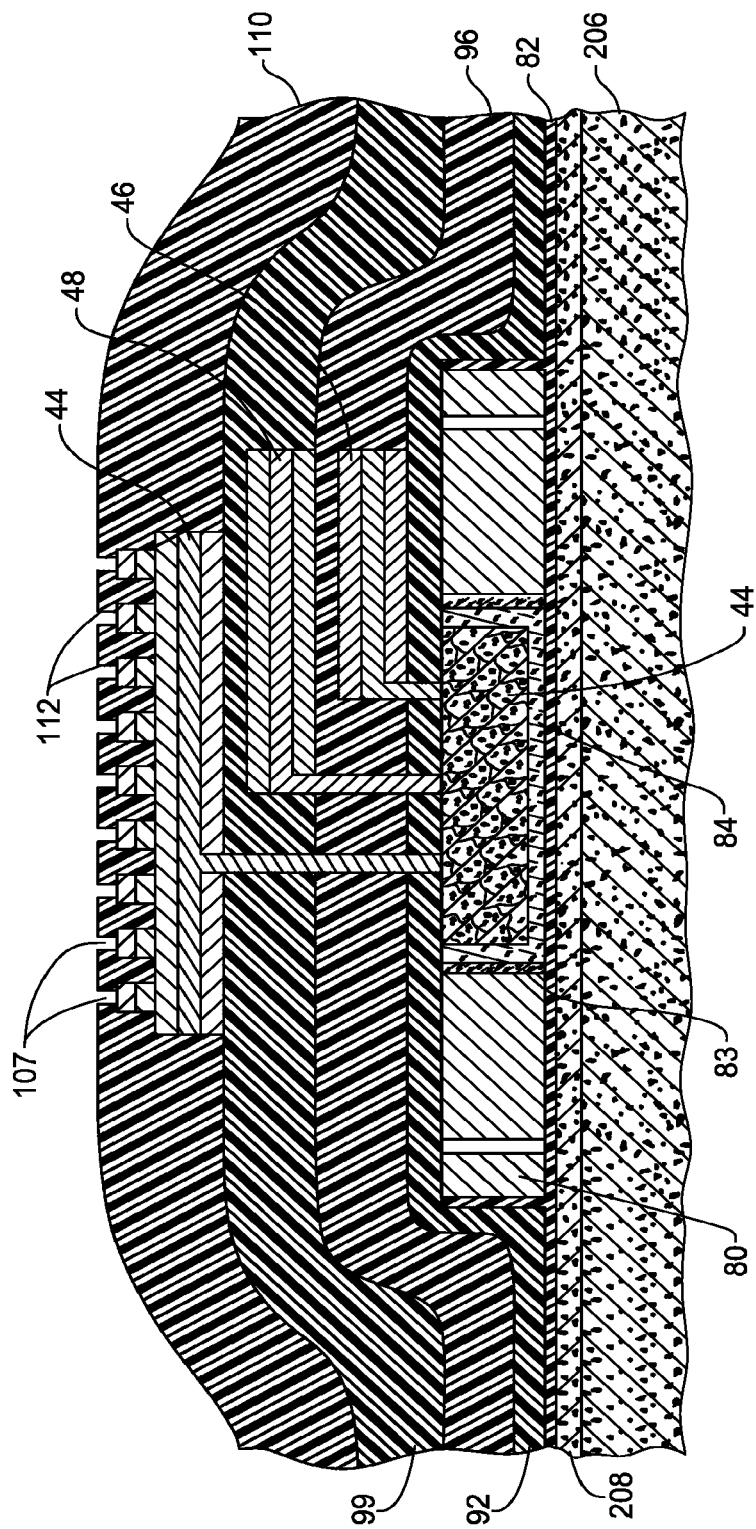
FIG. 33 depicts how the seating of the electrode-control module-conductor assembly on the carrier.

Assembly of electrode array assembly 40 continues with the seating and mating of the electrode-control module-conductor assembly to the coupon 182 as represented by FIG. 33. In this process step, the sub-assembly including the electrodes, the control modules and the conductors is disposed over the carrier-containing coupon 182 so that the shell-encased control modules 44 seat in the carrier windows 81. In this mating process, the parylene of intermediate insulating layer 92 (FIG. 8) of the electrode-control module-conductor assembly is bonded to the exposed parylene layer 203 of the carrier-containing coupon. This parylene-to-parylene bond is what holds the electrode-control module-conductor sub-assembly to the carrier 80. The two parylene layers 92 and 203 become a single parylene layer. Accordingly, in FIGS. 33-37, these layers are identified as the bottom most intermediate insulating layer, layer 92.

In FIG. 33, insulating layers 82, 92, 96, 99 and 110 are shown as extending across the openings 198 that separates the carrier tab 194 from the adjacent beams 196. As discussed above the parylene forming these layer 82, 92, 96, 99 and 110 is applied so as to extend over a surface area that is larger than that of the electrode array 40 under fabrication. Consequently, as seen in FIG. 33, the insulating layers formed by the parylene extend beyond the perimeter of the carrier tabs 104. These insulating layers extend across the gaps between the carrier tabs 194 and the adjacent carrier beams 196. These insulating layers also extend over the carrier windows 198 between the beams 194. Owing to the flexible nature of the parylene, within the carrier openings 198 the parylene forming the passive side insulating layer 82 bonds with the parylene forming the bottommost intermediate insulating layer 92. This parylene-to-parylene bonding is performed under at least a partial vacuum. Consequently, as a result of this process the parylene of layers 92, 96, 99 and 110 collapse over the side edges of the carrier 80. The parylene of layer 92 bonds to the parylene of layer 82. Thus, each membrane 70 is formed by the laminate structure of the insulating layers 82, 92, 96, 99 and 110. Similarly, adjacent the outer edges of the carrier bridges 188 and 192, the parylene layers extends between the longitudinally adjacent carrier tabs 194. In this area between the carrier tabs 194 the parylene forming insulating layers 82 and 92 again bond. Each membrane 72 thus similarly consists of a laminate comprising insulating layers 82, 92, 96, 99 and 110.

Electrode array assembly 40 is now removed from substrate 206. This process begins with the removal of the parylene layers 82, 92, 96, 99 and 110 that extend over carrier slots 184 and 186. The removal of the parylene above and below the carrier slots 186 allows array tabs 64 and beams 66 to flex relative to each other. A reactive ion etch process, an oxygen plasma etch process, can be used to remove these sections of parylene. As a consequence of this etching process, as seen in FIG. 34, tabs 204 are exposed.

The electrode array assembly removal process continues with the severing of the carrier from the surrounding section of the coupon 182. Typically this process involves the removal of tabs 204. In versions of the invention wherein the carrier-defining coupon 182 is formed from Nitinol, tabs 204 are removed by using a mixture of $HF_3$ and $HNO_3$ to etch away the Nitinol forming the tabs. As a consequence of this process, a small remainder section of each tab, identified as crest 212 in FIG. 35 projects outwardly from perimeter of the carrier 80 (one crest shown). A crest also extends outwardly from the surrounding coupon 182. Since that crest is not relevant to this invention, it is not illustrated. Another reactive ion etching process may then be performed to remove the parylene of insulating layer 82 that was previously covered by the tabs.

Once the tabs 204 are removed, a layer of parylene is deposited over the assembly. This layer is approximately 1 micron thick. In FIG. 36, this layer is only illustrated as layer 216 disposed over the sides of the carrier 80. Thus, this parylene layer 216 covers the exposed side edges of the frame 80 including the crests 212. While not illustrated, it should be understood that parylene layer 216 also extend over the exposed face parylene layer 110. Once layer 216 is applied, a reactive ion etching process may be used to remove portions of the parylene forming layer 216 so as ensure openings 112 remain open.

The silicon dioxide layer 208 between substrate 206 and the passive side insulating layer is removed. This process may be performed by etching away the silicon dioxide layer 208 using a chemical etch process. As seen by reference to FIG. 37 as a consequence of this etching process the section of the silicon dioxide material disposed under the sections of the coupon 182 that do not function as the carrier are also removed.

Once the silicon dioxide layer is removed from underneath the electrode array assembly 40, the electrode array 40 is no longer connected to either the coupon 182 or the substrate 206. The array 40 is lifted away from the coupon and substrate 206 for any further processing and testing that is not part of this invention.

III. Alternative Method of Assembly

An alternative method of assembling the electrode array assembly 40a (FIG. 49) of this invention can start with the formation of the coupon-defining carrier 182 previously described with reference to FIGS. 26, 26A and 27. In this version of the invention, the coupon 182 may have a thickness that is typically no more than 5 microns greater than the thickness of the control module 44. Once the coupon 182 is properly shaped, the carrier-forming section of the coupon may be itself shaped so this section of the carrier acquires the desired non-planar shape of the end assembly 40. The surface of the carrier 182 opposite the surface on which the electrodes 42 are to be disposed is then coated with parylene, step not illustrated. During the application of this parylene layer, the parylene is applied so as to coat the side surfaces of the carrier 80.

The coupon-defining carrier 182 is then bonded to the rigid substrate 206. As previously described with respect to FIGS. 29 and 30, substrate 206 is prepared for this bonding process by first applying silicon dioxide layer 208 over the substrate 206. Then, parylene layer 210 is coated over silicon dioxide layer 208.

Figure 38:
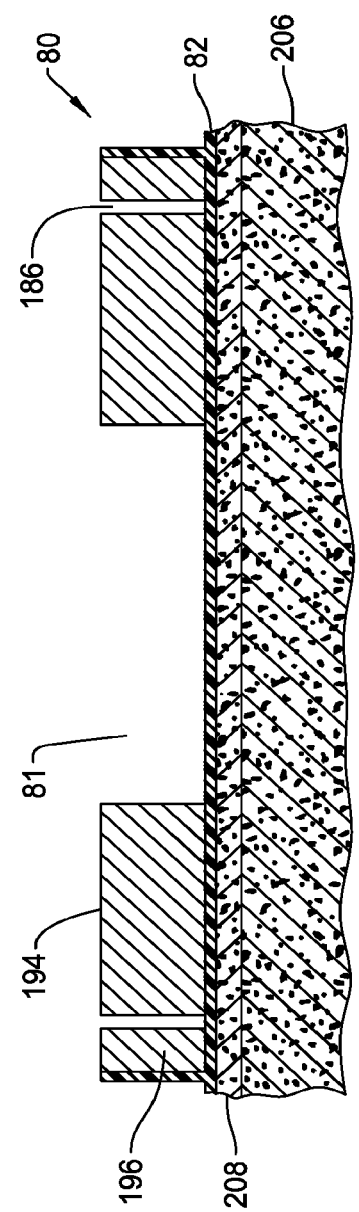
FIGS. 38-48 are a sequence of cross sectional views that depict an alternative process for assembling an electrode array of this invention.

FIG. 38 represents the bonding of the carrier-defining coupon 182 to the rigid substrate 206. If the carrier 80 was, in the early step, shaped, as a consequence of this process, the carrier-forming section of the coupon 182 is flexed back into the plane of the coupon 182. In FIG. 38 and subsequent FIGS. 39-48, the two parylene layers 203 and 210 bonded together are identified as their final form in the assembled array, passive side insulating layer 82. The layer of parylene disposed over the side surfaces of the carrier 80 is considered part of the passive side insulating layer 82.

Figure 39:
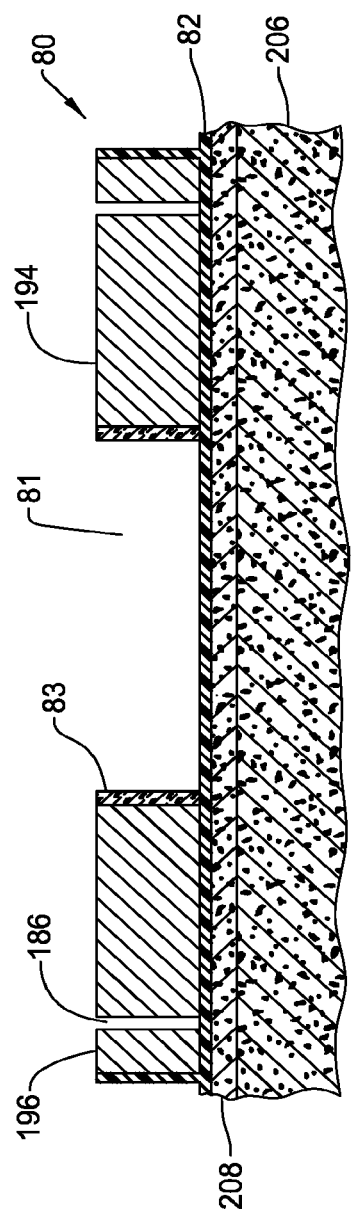

The next step in this method of assembly 40 fabrication of this invention, is, as represented by FIG. 39, the formation of the electrically insulating frame 83. Frame 83 may be formed from the material used to form the frame and using the processes described with respect to FIG. 32.

Figure 40:
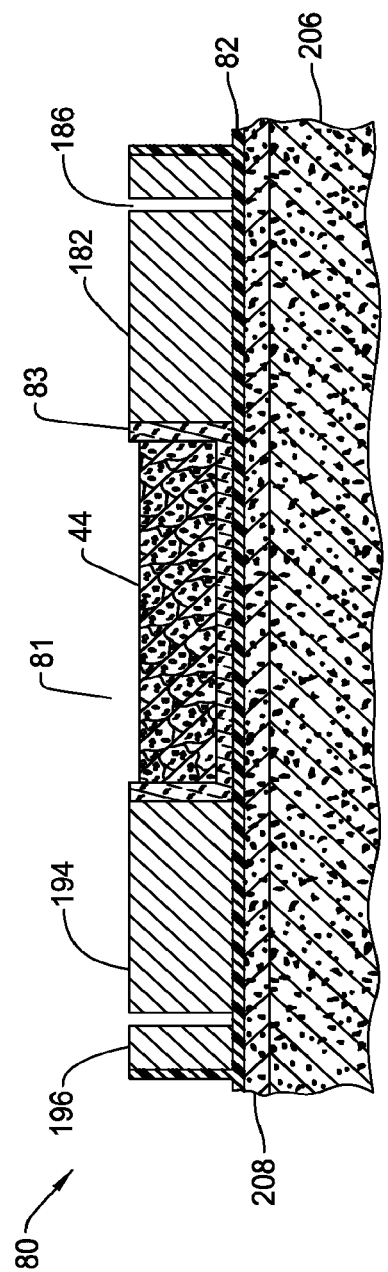

Once frame 83 is formed, in this method of assembling array 40a, control module 44 is seated in the opening defined by the frame 83 as depicted illustrated with respect to FIG. 40. In FIG. 40, control module 44 is shown not encased in a shell. In a variation of this method of assembly of the invention, prior to the seating of the control module 44 in the frame 83, the control module is at least partially encased in a biocompatible shell. For example, the shell may be formed from silicon. In versions of the invention in which the control module is so encased in shell, the coupon 182 from which the carrier 80 is formed has a thickness that is typically no more than 5 microns greater than the combined top-to-bottom thickness of the control module and the shell. Thus, at this stage of the assembly process the top of the control module 44 may be below the surrounding top surface of the carrier-defining coupon 182.

Figure 41:
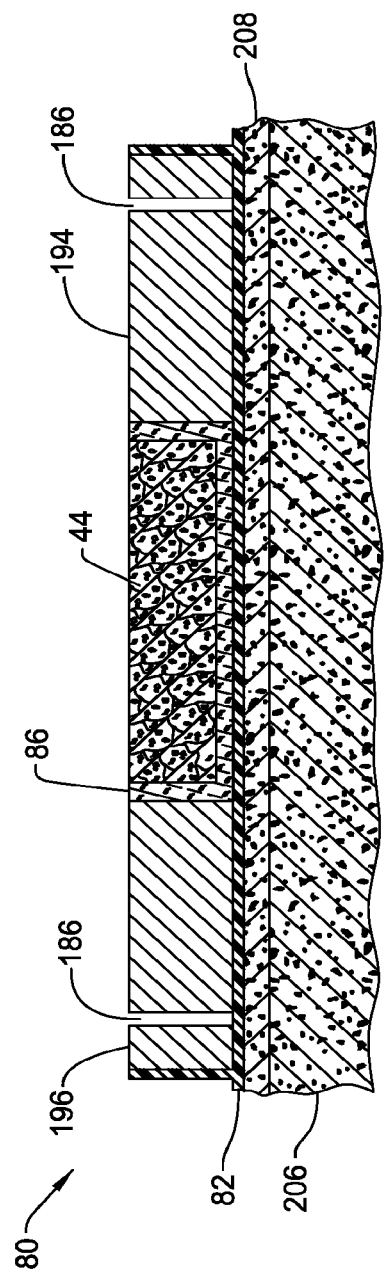

Using a mechanical lapping process, the top section of the carrier-defining coupon 182 and frame 83 are then removed so that, as depicted by FIG. 41, the top surface of the coupon 182 is coplanar with the exposed top surface of the control module 41.

Figure 42:
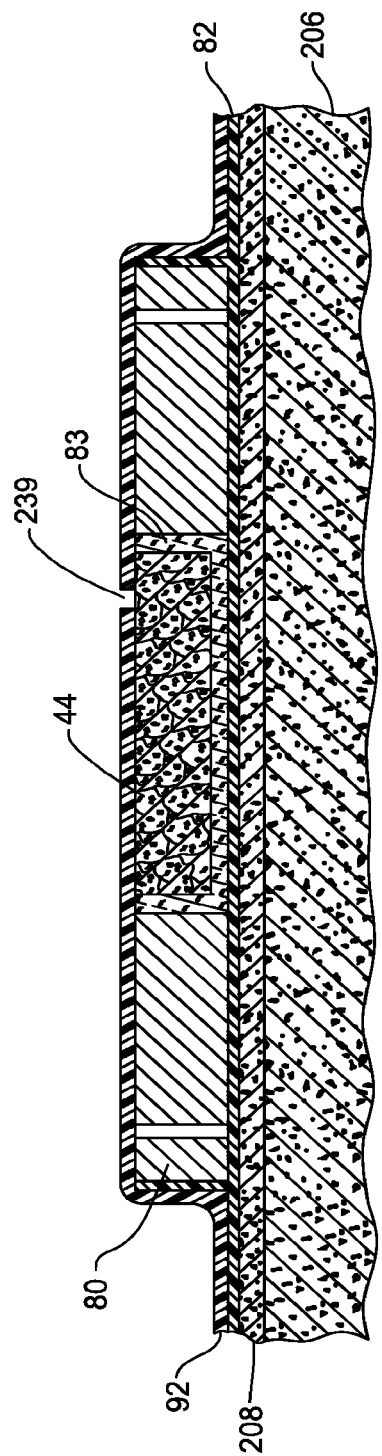

A parylene coating is then applied to the exposed coplanar faces of the control module 44 and the coupon 182, as represented by FIG. 42. This parylene becomes the parylene of intermediate insulating layer 92 and therefore identified as such in FIGS. 42-48. As depicted in FIGS. 42-49 the parylene forming layer 92, as well as the parylene forming insulating layers 96, 99 and 110, extends beyond the top surfaces of the carrier-forming features of the coupon. This parylene extends over slots 184 (not illustrated) and slots 186. This parylene also extends over and into windows 198 formed in the carrier 80. This parylene is bonds to the parylene of the previously applied passive side insulating layer 82. As occurs during the previously described method of manufacture, these multi-layer parylene laminates form the array membranes 70. The While not illustrated, it should be understood from this Detailed Description that parylene forming layer 92 as well as the layers above layer 92 extend between the outermost carrier tabs 194. These multi-layer parylene laminates form the array membranes 72.

Holes 239 (one shown), essentially identical to holes 138 of FIG. 11 are formed in insulating layer 92 to provide access to the underlying control module bond pads 91. The process used to form holes 239 is the same as the process used to form holes 138.

Figure 43:
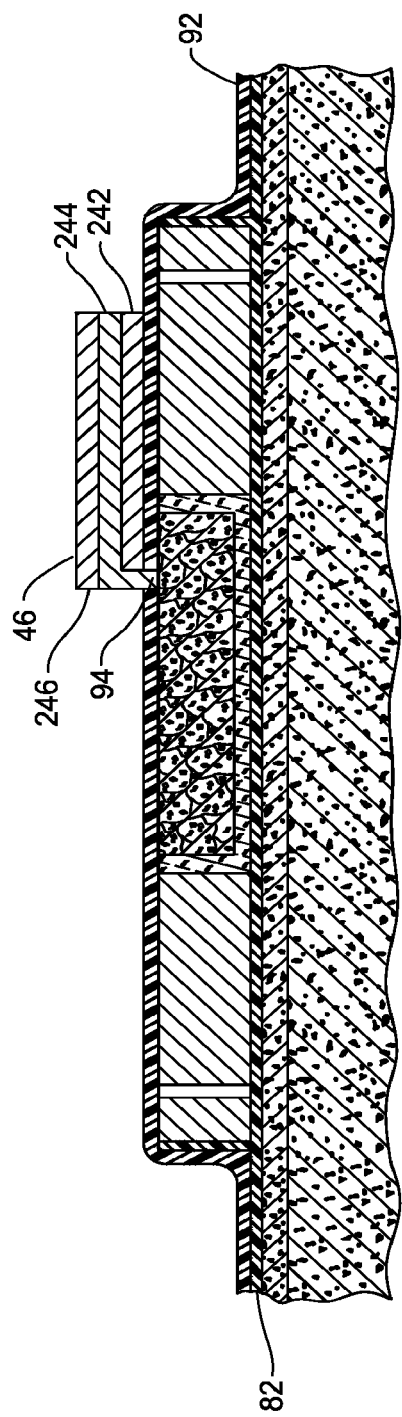

The next series of steps in the assembly of the electrode array 40 according to this method, represented by FIG. 43, is the formation of conductors 46 and associated bus conductor. Conductors 46 are formed using the same processes described with respect to FIGS. 12-15. In FIG. 43 the initial titanium adhesion layer of the conductor is called out as layer 242. The gold layer of conductor 46 is called out as layer 244. The topmost titanium layer is called out as layer 246. The gold applied in the electroplating process used to form the largest section of layer 244 flows into the holes 239 so as to form the vias 94. Formed simultaneously with the conductors 46 is the conductor integral with bus 118 to which the conductors 46 are connected. The same titanium, gold and titanium layers, 242, 244 and 246, respectively that form conductors 46 form the conductor of bus 118.

Figure 44:
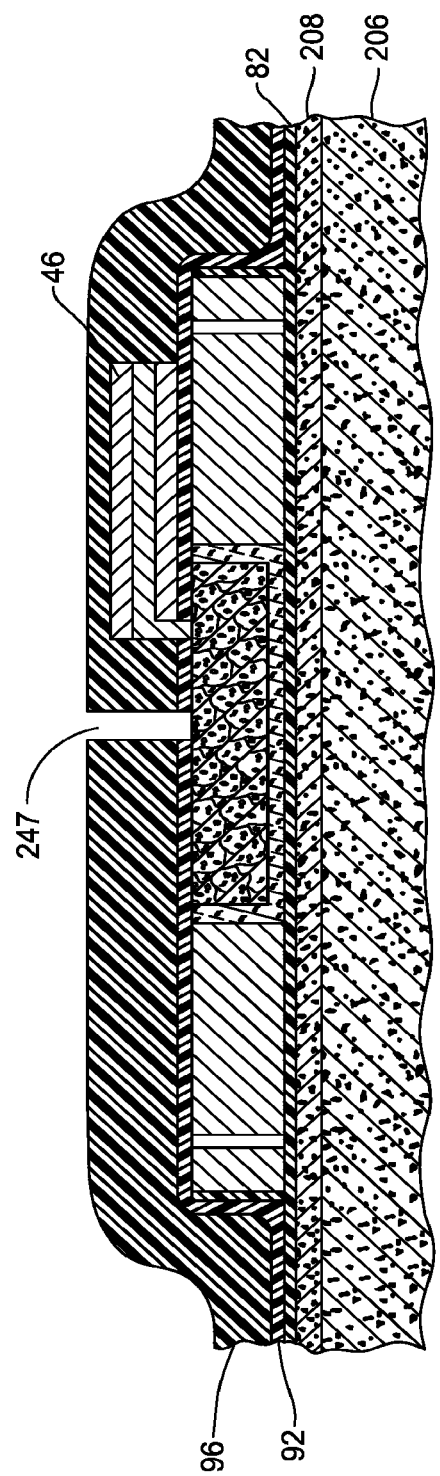

As represented by FIG. 44, a layer of parylene is applied over conductors 46 and the exposed surfaces of the intermediate insulating layer 92 to form intermediate insulating layer 96. Holes 247 (one shown), essential identical to holes 154 (FIG. 17) are formed to extend through insulating layers 92 and 96 to the control module contact pads 91. This step is essentially identical to the step described by reference to FIG. 17 in which the 154 154 are formed.

Figure 45:
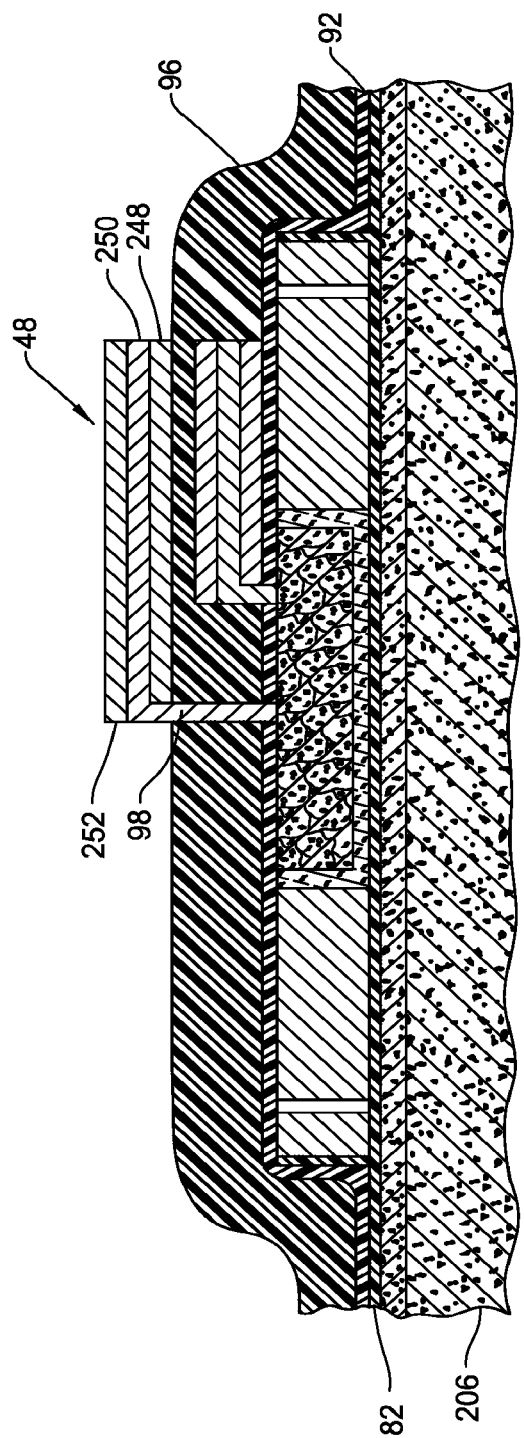

Once the openings are formed in the intermediate insulating layers 92 and 96, conductors 48 are formed. The process steps used to form conductors 48 are the same described with respect to FIGS. 17-19. In FIG. 45 the bottommost titanium layer of conductor 48 is called out as layer 248. The gold intermediate layer is called out as layer 250. The topmost titanium adhesion layer is called out as layer 252. The gold applied by the electroplating to form layer 250 also forms the vias 98.

During the process steps in which conductors 48 are formed, the titanium and gold of layers 248, 250 and 252 is also deposited to from the bus 118 conductor to which conductors 48 are connected. Thus, this conductor is like, conductors 48, disposed over intermediate insulating layer 96.

Figure 46:
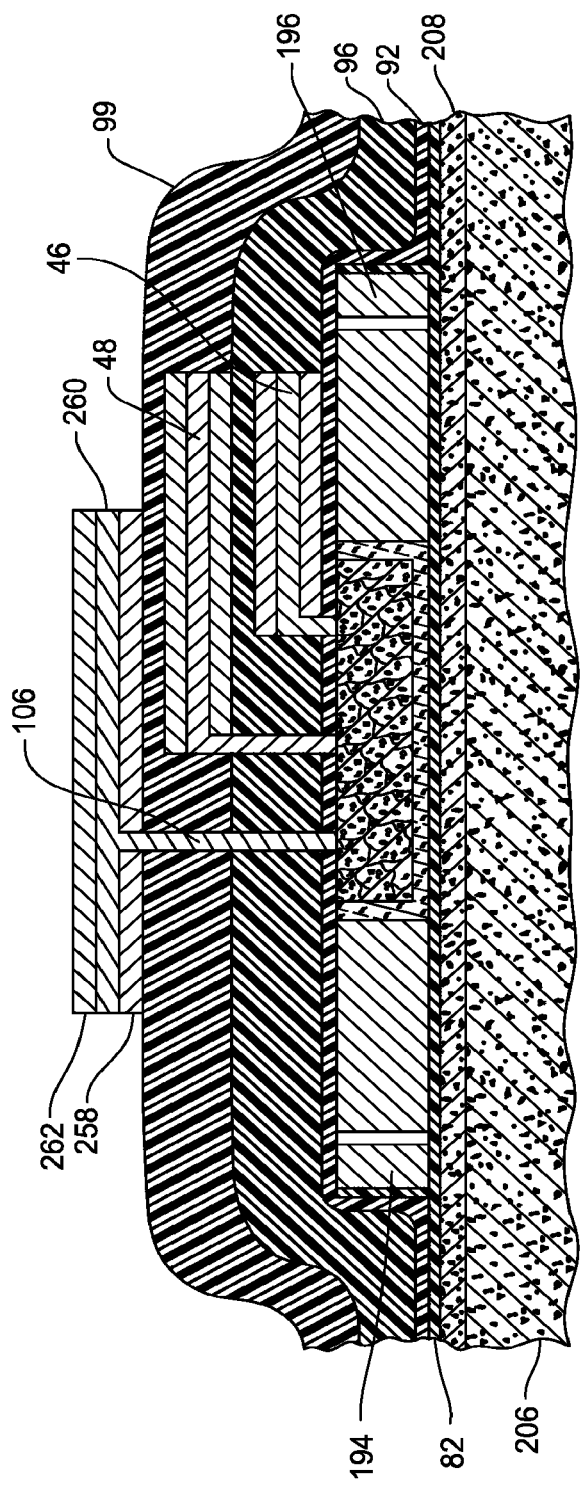

Assembly of electrode array 40 continues with the application of parylene over the exposed surfaces of conductors 48, the bus conductor to which conductors 48 are connected and intermediate insulating layer 96. This parylene, as seen in FIG. 46, forms the intermediate insulating layer 99. Once layer 99 is formed holes (one shown and not identified) are formed in the intermediate insulating layers 92, 96 and 99. These holes extend to bond pads 91 integral with the control modules 44.

Electrodes 42 are then formed on top of intermediate insulating layer 99. The electrodes are formed in process steps analogues to the process steps described with respect to FIGS. 21-23. A titanium adhesion layer is applied to the exposed surface of intermediate insulating layer 99. A gold seed layer is applied over the titanium layer. A mask is applied so as to have openings over where the electrode bond pads are to be located. Gold is added to the exposed sections of the gold seed layer to form the layers 103. A portion of this gold also forms the vias 106. Titanium layers 104 are formed. The mask is removed. The sections of first the gold seed layer and then the underlying titanium adhesion that are not part of the base pads are then removed. Thus, as represented by FIG. 46, the electrode base pad consists of titanium layer 258, gold layer 260 and titanium layer 262.

Figure 47:
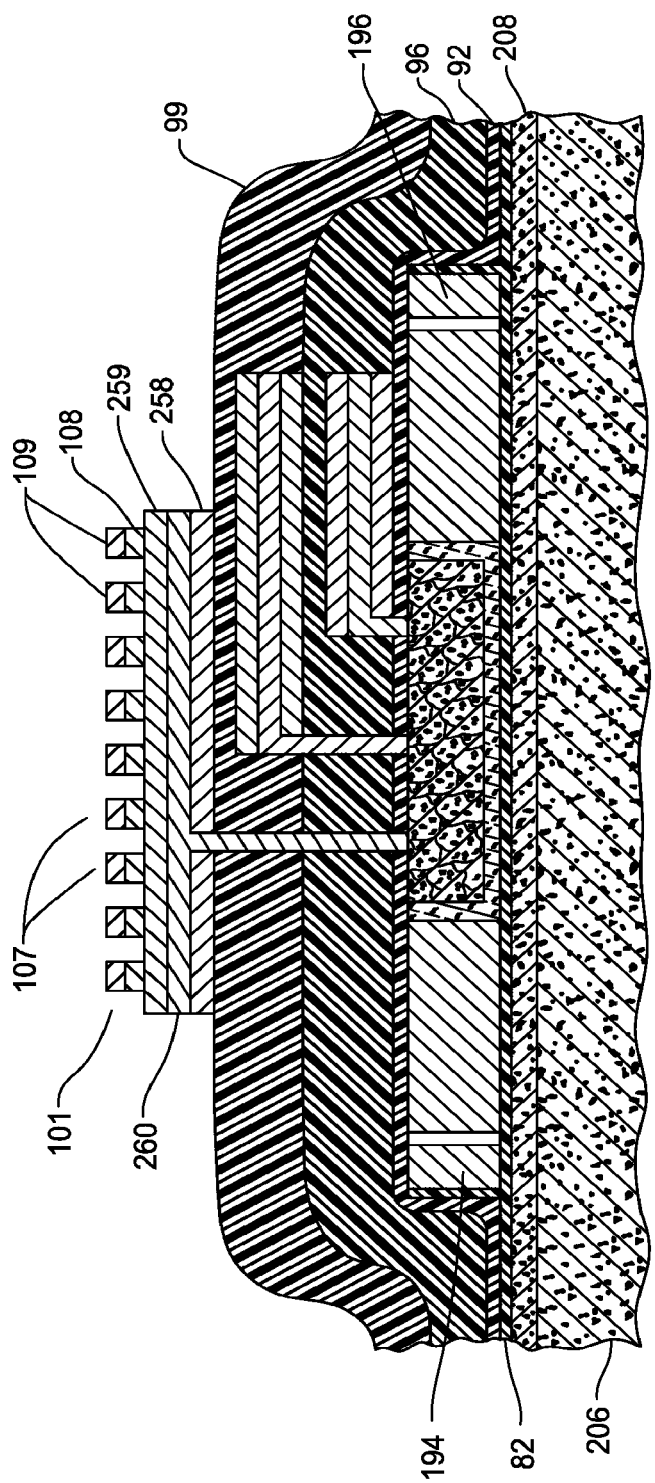

Fabrication of the electrodes 42 continues with the fabrication of the buttons 107. Titanium is initially deposited over the exposed titanium layers 262 of the electrode base pads. Iridium is then deposited over the titanium. In FIG. 47, as in FIG. 2, these layers are called out as titanium layers 108 and iridium layers 109.

Figure 48:
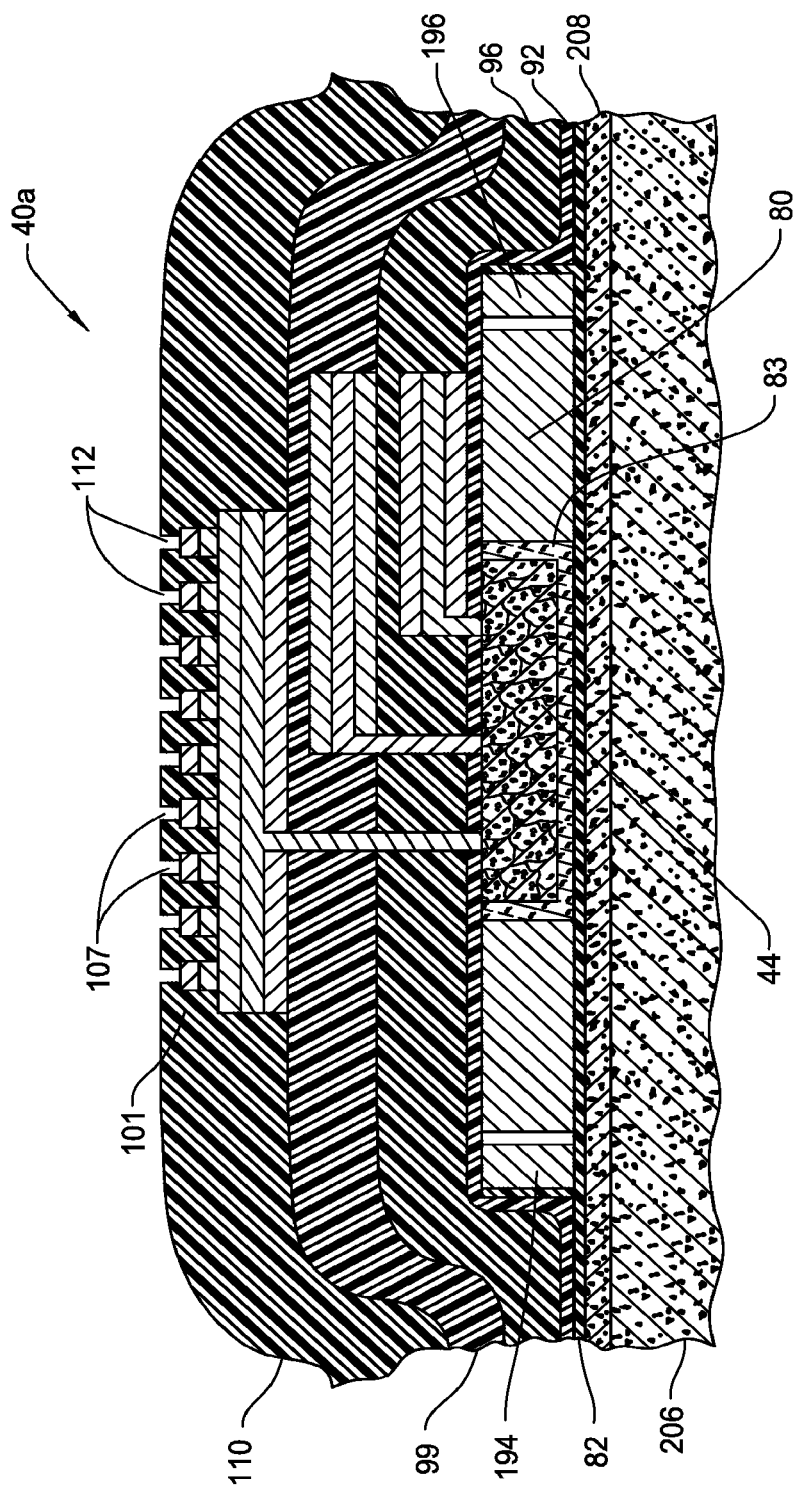

Once the buttons 107 are formed, as represented parylene is applied to the exposed surfaces of the electrodes 42 and the intermediate insulating layer 99 to form the outer insulating layer 110, as represented by FIG. 48. Portions of the insulating layer 110 are removed over electrode buttons 107 to provide the openings 112 through which the buttons are exposed to the tissue.

The essentially completely assembled electrode array 40a is then removed from the coupon 182 and substrate 206. The process steps used to accomplish these separations are identical to those described with respect to FIGS. 34-37. These process steps include the steps of selectively removing the parylene so as to uncover the slits 184 and 186 around and in the carrier. Tabs 204 are removed. A layer 216 of parylene is applied so as to cover the exposed surfaces of the carrier. Sacrificial layer 208 is removed to allow the array 40a to be lifted of the substrate 204.

In this method of assembling the electrode array 40, the control modules 44 are seated in the carrier during an initial step of assembly process. The application of the insulating layers 92, 96, and 99 over the substrate can be considered the formation of a flexible sheet of insulating material over the substrate. The insulating and conductive layers that collectively define the array 40 electrodes, conductors and vias are formed on the carrier. Thus, in this version of the invention the process steps associated with having to bond an electrode and conductor sub assembly to the carrier are eliminated.

IV. First Alternative Electrode Array

Figure 49:
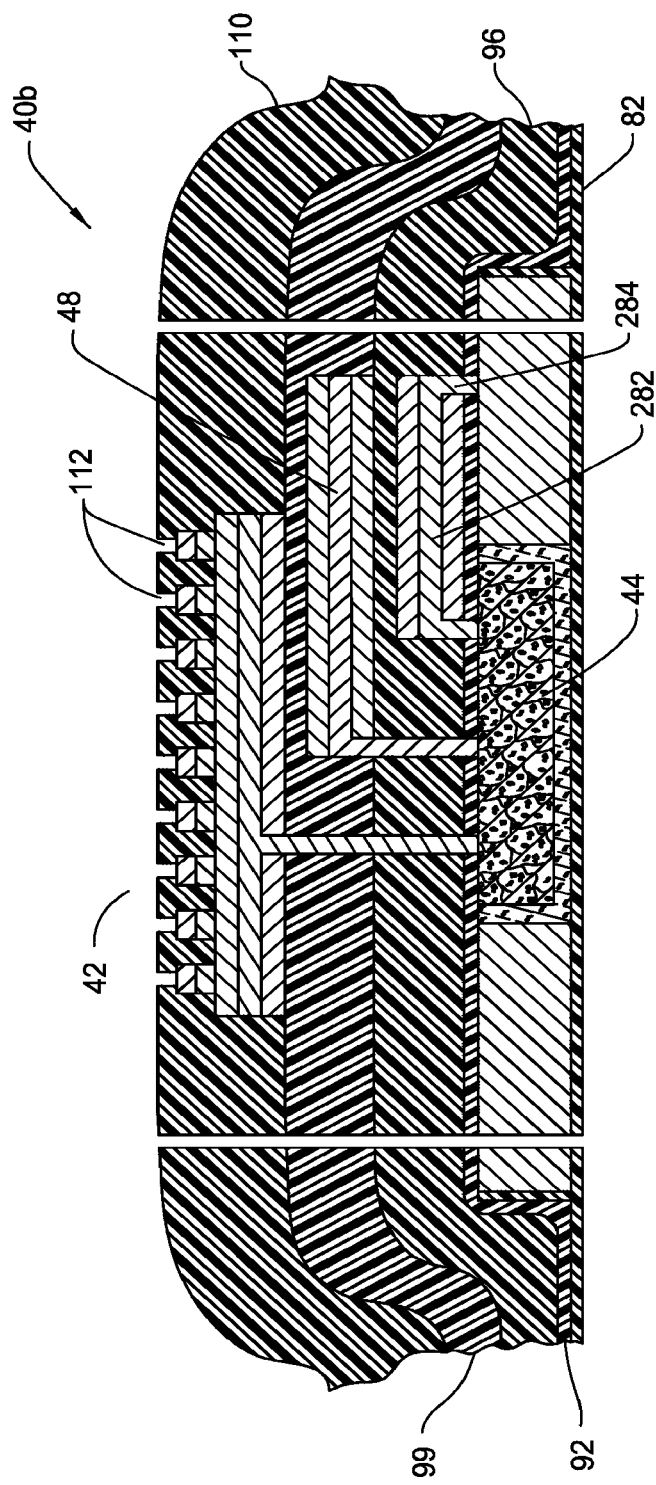
FIG. 49 is a cross sectional view of a single electrode and control module of a first alternative electrode array of this invention.

FIG. 49 illustrates in cross section a portion of an alternative electrode array 40b of this invention. Electrode array 40b of this invention includes the same electrode, control module 44 and carrier 80 of the previously described versions of this invention. Array 40b includes the previously described conductor 48 and insulating layers 82, 92, 96, 99, 110 and 216 (layer 216 not illustrated.)

Instead of the previously described conductors 46, array 40b includes a conductor 282. Conductor 282 extends from a bond pad 91 integral with the control module 44 over a section of intermediate insulating layer 92 to a location over the carrier. In FIG. 49, conductor 282 is shown extending over the carrier tab 194 in which the control module 44 with which the conductor 282 is seated. A via 284, which extends through intermediate insulating layer 92, connects the end of conductor 282 to the carrier 80.

Figure 50:
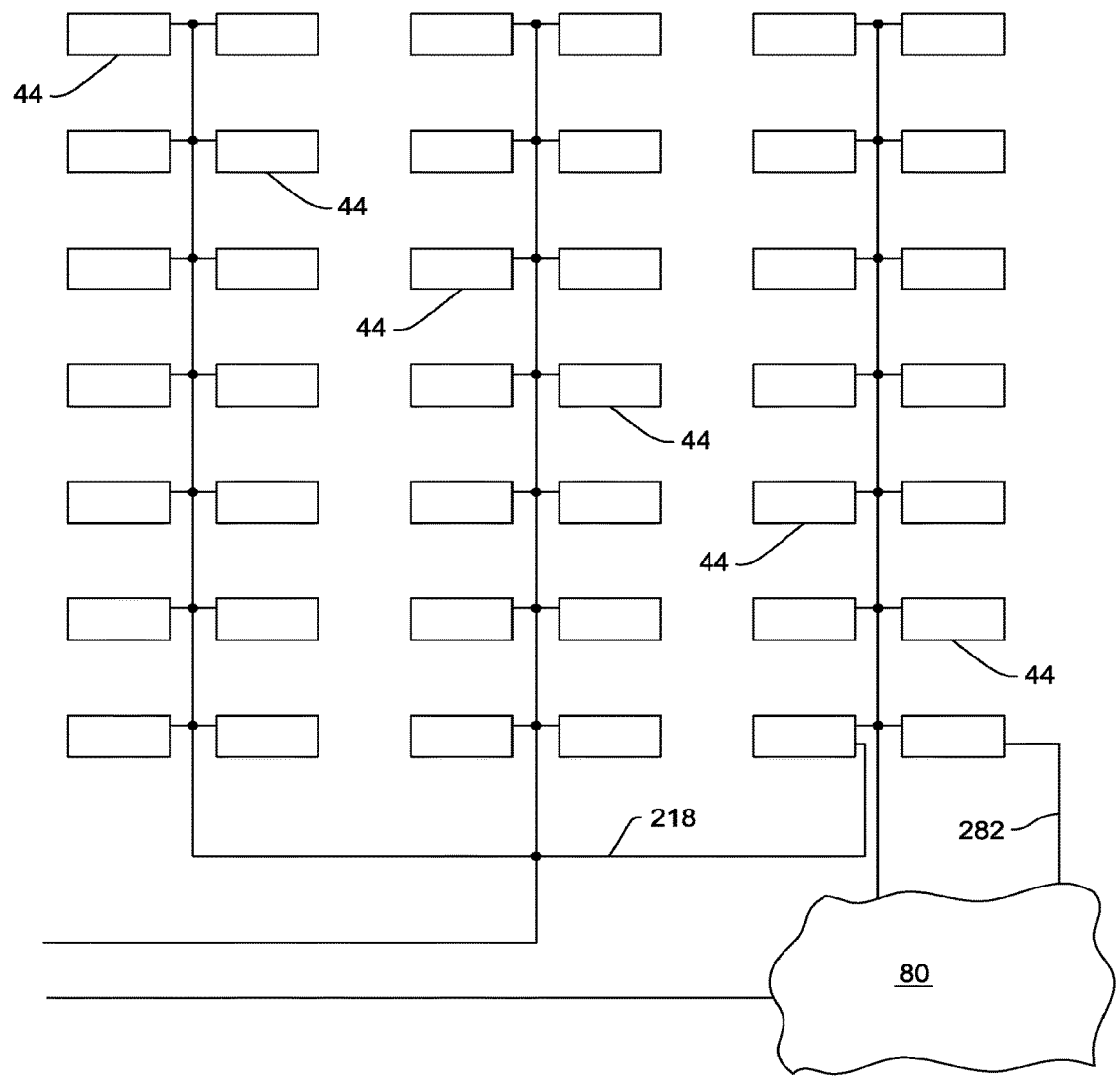
FIG. 50 is a block diagram of how signals are distributed to the control modules of the electrode array of FIG. 49.

In this version of the invention, the carrier 80, which is formed from conductive material, functions as the common ground plane for the plurality of control modules 44. Consequently, as seen in FIG. 50, array 40b is constructed so that a one-wire bus 288 functions as the conduit over which power and control signals are transmitted to the plurality of control modules 44.

V. Second Alternative Electrode Array

Figure 51:
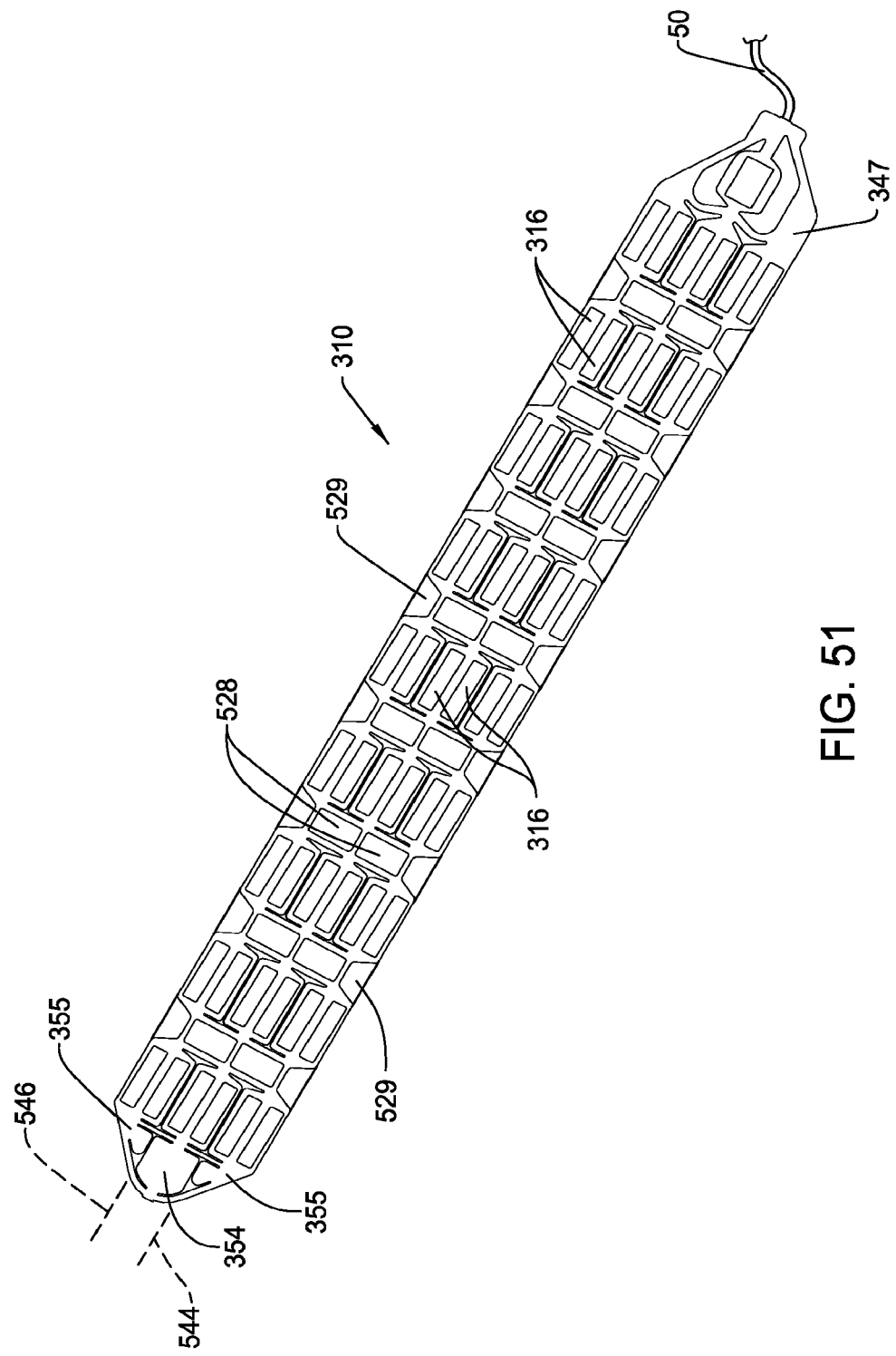
FIG. 51 is a plan view of a second alternative electrode array of this invention.
Figure 52:
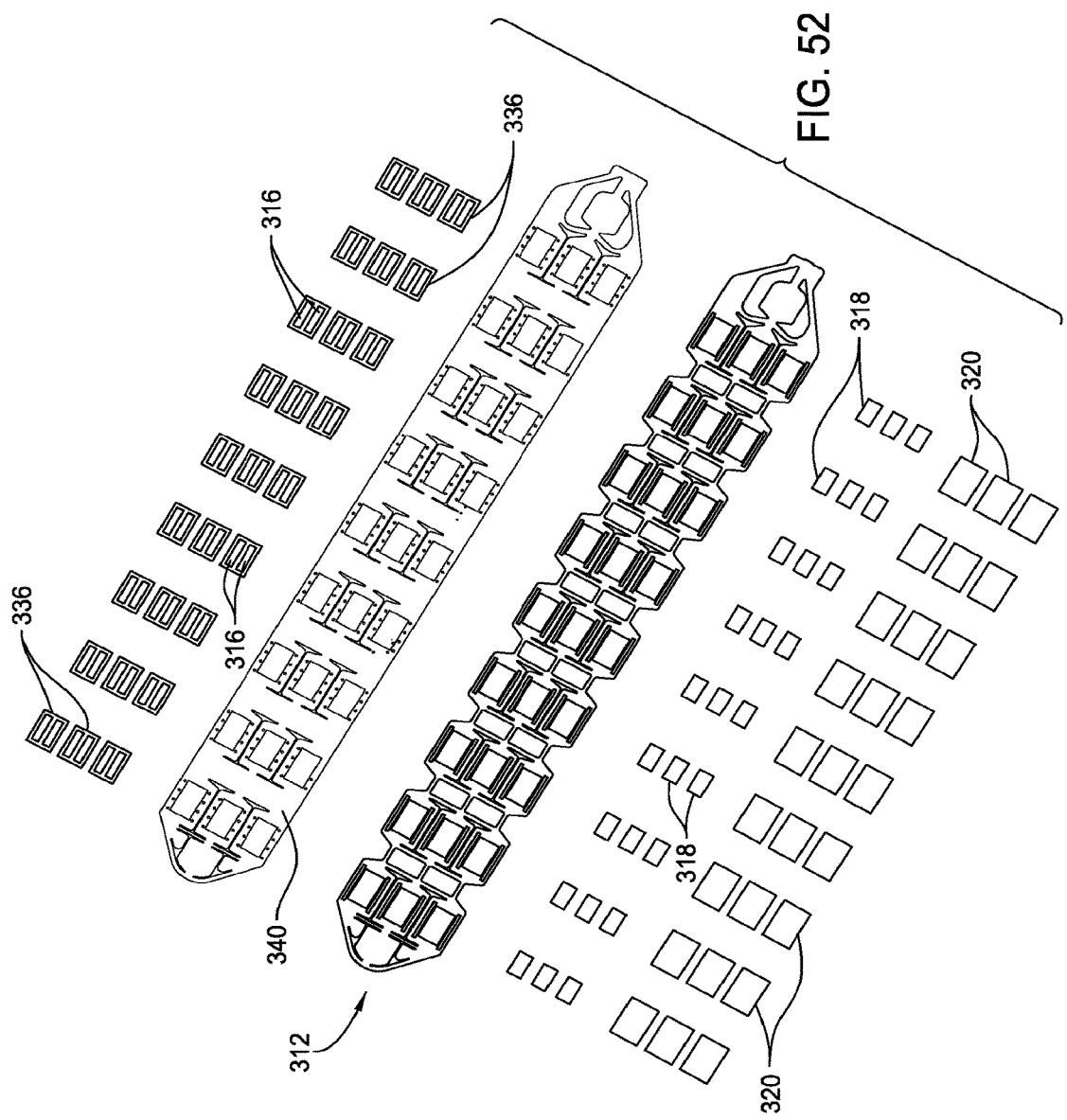
FIG. 52 is an exploded view of the major component layers of the electrode array of FIG. 51.
Figure 53:
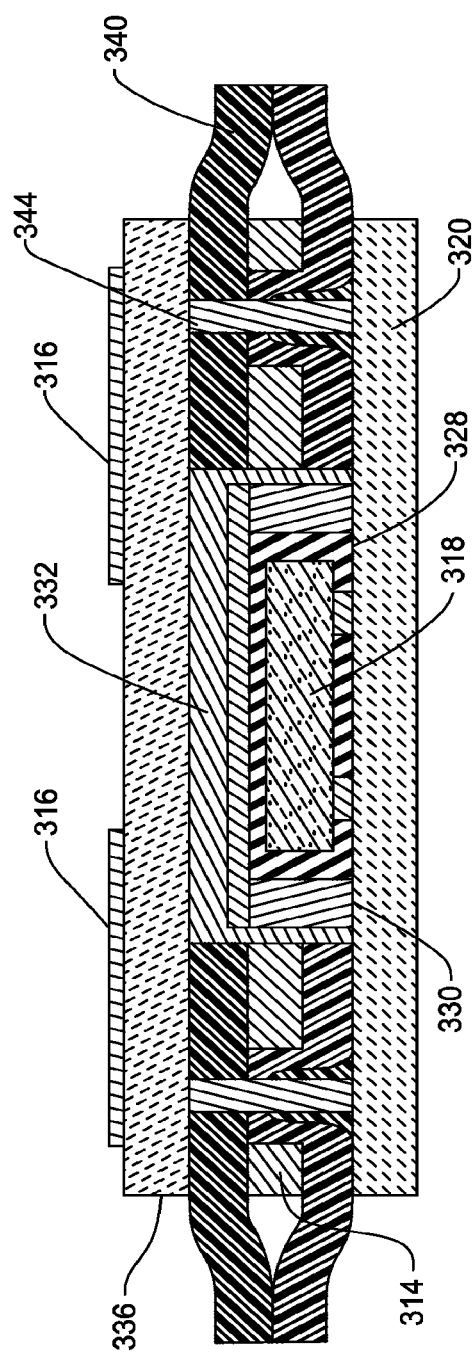
FIG. 53 is a cross sectional view of the components mounted to one of the contiguous pairs of tabs of the electrode array of FIG. 51.
Figure 54:
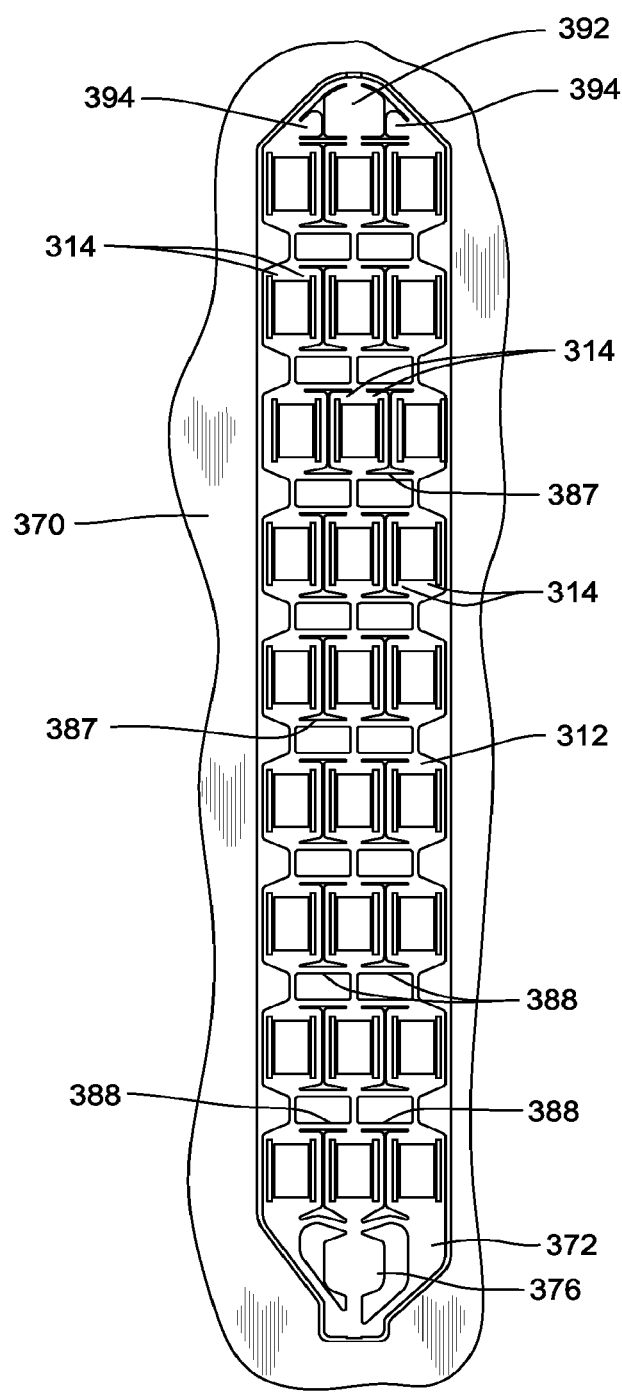
FIG. 54 is a plan view of a single carrier of the electrode array of FIG. 51 while the carrier is still integral with the coupon from which the carrier is formed.
Figure 54A:
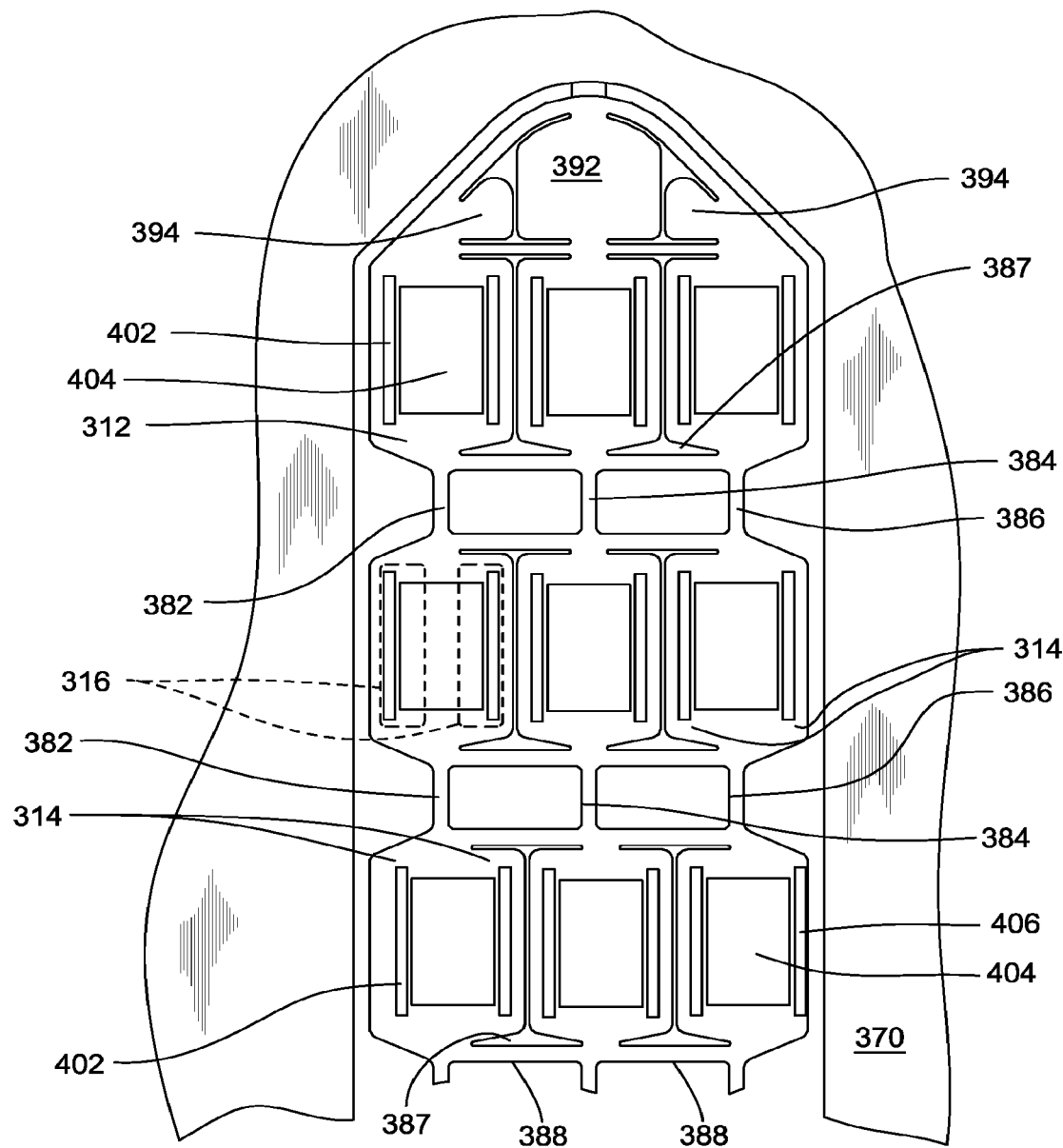
FIG. 54A is an enlarged view of the distal end of the carrier of FIG. 54.

A second alternative electrode array 310 of this invention is now described by initial reference to FIGS. 51-53. Array 310 includes a carrier 312 that is at least flexible, if not superelastic. Carrier 312 is formed to have plural pairs of contiguous tabs 314 (FIG. 54A). A pairs of electrodes 316 are disposed over each contiguous pair of tabs 314. A control module 318 (ASIC) is disposed seated in each pair of carrier tabs 314. Each control module 318 is thus located below a pair of electrodes 316. Each control module 318 includes the components that source current to/sink current from the overlying electrodes 316.

Each pair of carrier tabs 314 and associated control module 318 are disposed over a ceramic substrate 320. Substrate 320 is formed with vias 445 and 447 and conductors 443 (FIG. 58) that provide conductive paths to/from the control module 318. The control module 318 is substantially encased in synthetic resin shell 328. Shell 328 forms a non-porous seal around substantially the whole of the control module 318. A ring 330 extends around the outer perimeter of shell 328. A lid 332 extends over the top of shell 328 and the top face of ring 330.

A ceramic superstrate 336 extends over each pair of contiguous carrier tabs 314 and the associated control module 318. The electrodes 316 that form each pair of array electrodes are formed on the outer exposed surface of substrate 336. Vias 338 (FIG. 60) extend through substrate 336 to provide electrical connections to/from the electrodes 316.

Figure 66:
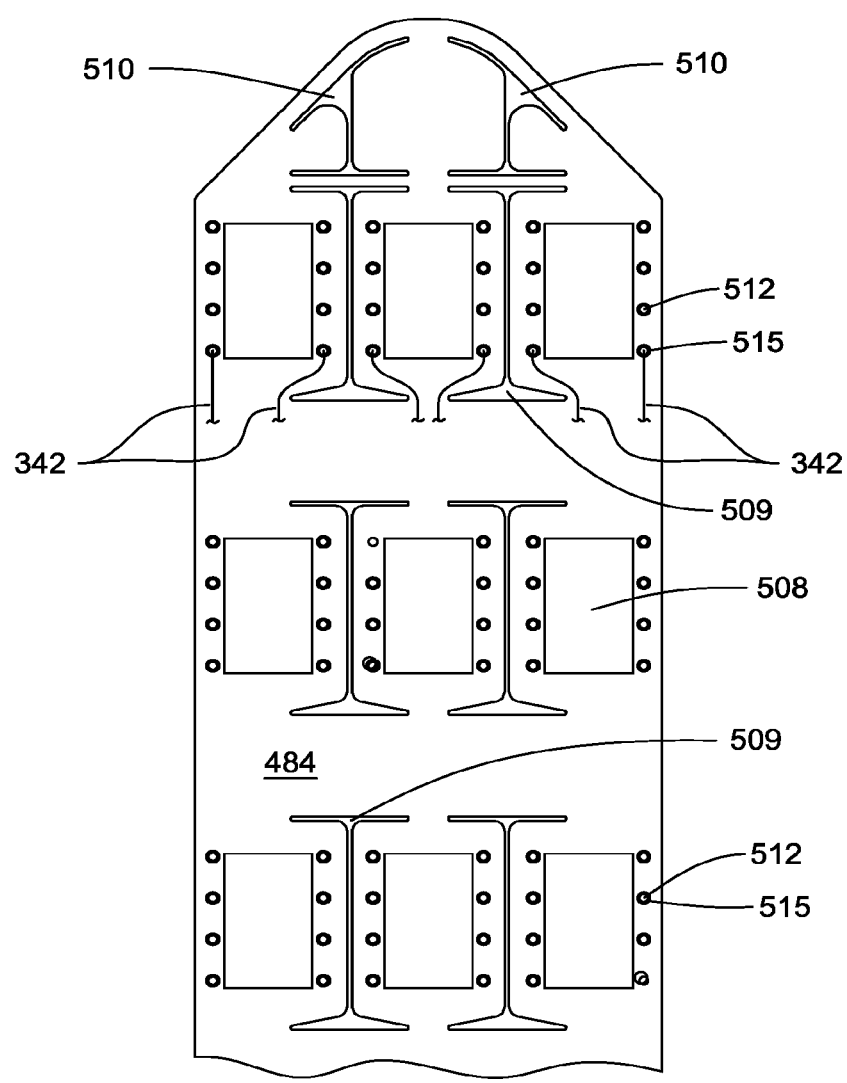
FIG. 66 is a plan view of the distal end of the middle layer, the conductor layer, of electrically insulating material of the carrier-laminate sub-assembly of FIG. 63.

Carrier 312 is disposed within a flexible, electrically insulating, non-porous laminate 340. In one version of the invention, laminate 340 is formed from plural layers of liquid crystal polymer (LCP). Laminate 340 is formed with conductors 342 (FIG. 66). The laminate conductors 342 are formed on one of the surfaces of a laminate-forming layer 484 of LCP. Conductors 342 form sections of the electrical paths to/from the control modules 318.

Posts 344 extend between each substrate 320 and the overlying superstrate 336 through the intermediate laminate 340. The posts 344 serve as conductive paths to/from the electrodes 316 and the control modules 318. At least some of the conductors 342 are electrically connected to posts 344. Posts 344 also function as structural members that hold the substrate 320 and superstrate 336 to the other layers of components that form the electrode array 310 of this invention.

A solder plug 472 disposed on superstrate 336 is bonded to lid 332. Solder plugs 472 thus further hold the superstrates 336 to the rest of the array 310.

Electrode array 310 is further formed to have a base 347 that forms the most proximal end of the array. Cable 50 extends from array base 347. At the most proximal end, electrode array 310 is formed to have a head 354 and two opposed shoulders 355. Head 350 and shoulders 351 are analogous to head 74 and shoulders 76 of array 40.

VI. Method of Assembling the Second Alternative Electrode Array

The fabrication of electrode array begins with: the fabrication of the carrier 312; the fabrication of the control module 318; the fabrication of the substrates 320 and superstrates 336; and the fabrication of the carrier-laminate sub-assembly. Fabrication of these components can essentially occur simultaneously and independently of each other. Once these components are available, the control module 318 is mounted to the substrate 320. Shells 328 are formed over the control modules 318. The control module-substrate sub-assemblies are then fitted to the carrier-laminate sub-assembly. The superstrates 336, with the electrodes 316 already formed thereon, are seated on top of the control modules 318 and the laminate 340. Posts 344 are then formed.

Carrier 312 is formed from the same material from which carrier 80 (FIG. 26) is formed. Carrier 312 has a thickness of approximately 50 microns. The same method used to form carrier, 80, selective etching of material forming a coupon, is used to form carrier 312. FIGS. 54 and 54A illustrate one version of a carrier 312 of this invention formed within a coupon 370. Carrier 312 is formed so that the pairs of tabs 314 are arranged in a 9×3 array wherein there are nine longitudinally spaced apart rows of pairs of tabs 314. Each row tabs 314 contains three pairs of contiguous tabs 314. At the proximal end, carrier 312 is shaped to have a base 372 in which the three most proximal pairs of tabs 314 are formed. Carrier base 372 forms the foundation for array base 347. Proximal to the most proximal row of tabs 314, carrier base 372 is formed to have two openings 374, 378 that define a tab 376. Tab 376 is centered along the longitudinal axis that separates the tabs 314 the form the center pair of tabs 314. Tab 376 is located proximal to the most proximal row of tabs 314. Given that tab 376 is proximal to the most proximal row of tabs 314, tab 376 is the most proximally located tab on carrier 312.

Within each column of tabs 314, a bridge segment connects each pair of tabs with the longitudinally adjacent pair (or pairs) of tabs. In FIGS. 54 and 54A bridge segments 382 (two identified) connect the adjacent pairs of tabs 314 in the left most column. Bridge segments 384 (two identified) connect the adjacent pairs of tabs 314 in the center column of tabs; and bridge segments 386 (two identified) connect the adjacent pairs of tabs 314 in the right most column of tabs. The plural bridge segments forming each set of bridge segments 382, 384 are 386 are longitudinally aligned. Bridge segments 382, 384 and 386 are parallel with each other.

The carrier 312 is further formed to have beams 388 similar to beams 196 of carrier 80. Beams 388 extend between laterally adjacent bridge segments 382, 384 and 386. Each beam 388 that extends between a bridge segment 382 and the adjacent bridge segment 384 is collinear with an adjacent beam 388 extending between the same bridge segment 384 and the adjacent bridge segment 386. Each end of each beam 388 projects away from where the adjacent bridge segment 382, 384 or 386 extends longitudinally away from one of the associated pairs of tabs 314.

There is only single pair of aligned beams 388 associated with the most proximal row of tabs 314. These beams are located immediately forward of the tabs 314. There are two rows of beams 388 associated with each of the remaining rows of tabs 314. One pair of aligned beams 388 is spaced a short distance rearward from proximal ends of the tabs 314. The second pair of aligned beams is spaced a short distance distally forward of the distal ends of the tabs 314.

Given that each row of tabs 314 is spaced apart from the longitudinally adjacent row of tabs, it should be appreciated that each pair of aligned beams 388 is spaced away from the longitudinally adjacent pair of aligned beams 388. This spacing is between approximately 0.5 and 5.0 mm and often between 1.0 and 3.0 mm.

From FIG. 54A it will be observed that tabs 314 that extend outwardly from adjacent bridge segments 382 and 384 and from adjacent bridge segments 384 and 386 are spaced apart from each other. Further, as mentioned above, beams 388 are spaced away from the tabs 314. This feature spacing on the carrier serves to define within each row of tabs two I-shaped slots 387.

The carrier 312 is further formed so as to have a head 392 and shoulders 394. Head 392 and shoulders 394 for the rigid foundation for array head 350 and shoulders 351.

During the formation of carrier 312, the material forming the carrier is removed so as to form in each pair of contiguous tabs 314 three windows 402, 404 and 406. The longitudinal axes of windows 402, 404 and 406 are parallel with each other and parallel with the longitudinal axis of the carrier 312. Each row of windows 404 is centered on the line that could be considered the border between the contiguous pair of tabs 314. This line is also the axis line that extends through the associated set of bridge segments 382, 384 or 386. Window 404 is dimensioned so that when the carrier 312 is disposed over the control module 318, there is a separation of at least 25 microns between the outer surface of ring 330 and the border of the window 404. Windows 402 and 406 are laterally spaced away from the opposed sides of window 404. Each window 402 and 406 is therefore completely contained in one of the tabs 314 that form the contiguous pair of tabs. Windows 402 and 406 are spaced apart the same distance from window 406. Windows 402 and 406 are longer in length, (the dimension parallel to the longitudinal axis of the carrier) and shorter in width (the dimension perpendicular to the longitudinal axis of the carrier) than the associated window 406. In some versions of the invention each window 402 and 406 defines an area of approximately 200 microns by 4000 microns.

In FIG. 54A, for point of reference, the outlines of two electrodes 316 that form a pair of electrodes are shown as dashed lines.

Figure 64:
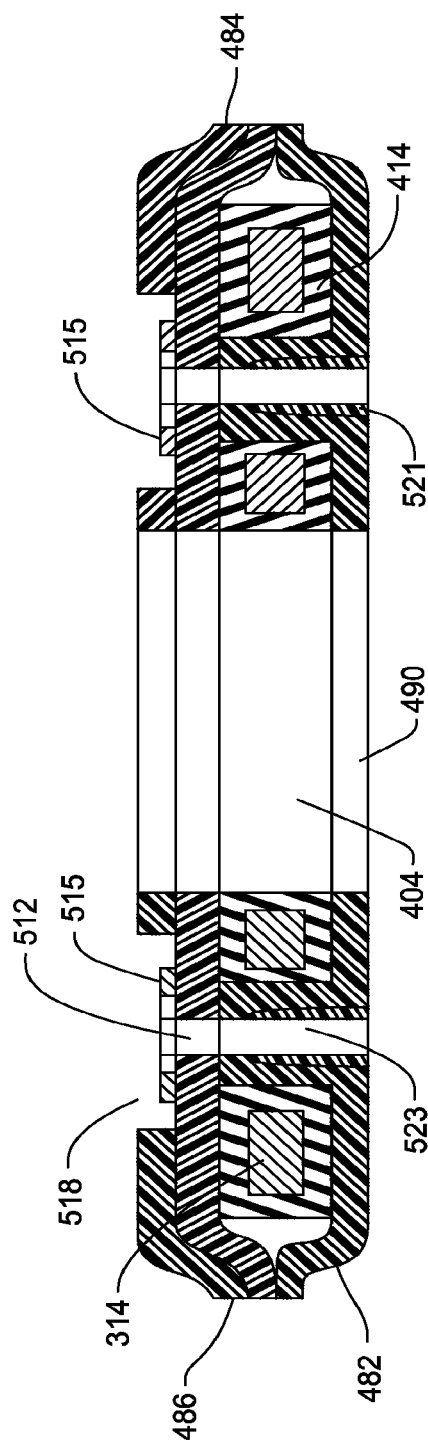
FIG. 64 is a cross-sectional view a section of the carrier-laminate sub-assembly of FIG. 63.

Once portions of coupon 370 are etched to form the carriers 312, an electrically insulating coating is disposed over the coupon. In one version of the invention this coating is a silicon oxide coating that is approximately 500 Angstroms thick. This coating is applied by a plasma deposition process. This coating is applied to the coupon 370 so as to cover all the exposed surfaces of the carriers 312 formed by the coupon. In FIG. 64 this coating is seen as layer 414 over a pair of contiguous tabs 314 of a coupon. The layer 414 is thus seen as extending over the top and bottom major surfaces of the tabs 314, the opposed side faces and the interior faces of the tabs that define windows 402, 404 and 406. For ease of illustration only, this coating is only in FIGS. 64 and 68.

Control module 318 is similar to control module 42. Control module 318 is formed to have plural current sources and plural current sinks. The sources and sinks are of the type that allows the quantities of current sourced by/sunk to the module 316 to be adjusted. Plural sources and sinks are provided so that simultaneously different quantities of current can be sourced from/sunk to the individual electrodes 316 to which each control module 318 is connected. Each control module 318 may also include one or more circuit components that facilitate the measurement of the voltage present at each electrode 316 with which the control module is associated.

Figure 55:
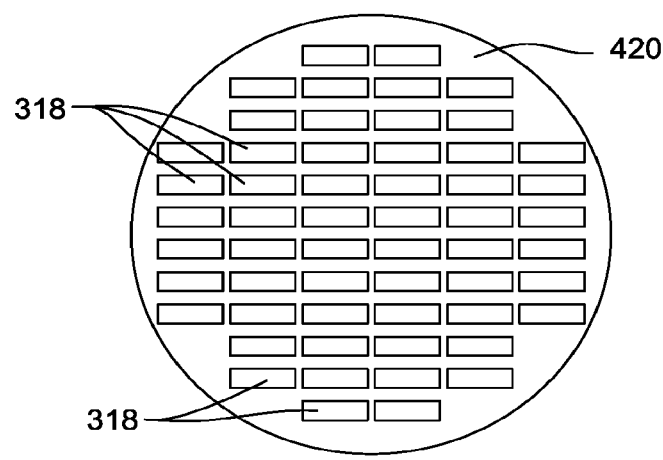
FIG. 55 is a plan view of a wafer on which plural control modules of the electrode array are formed.
Figure 56:
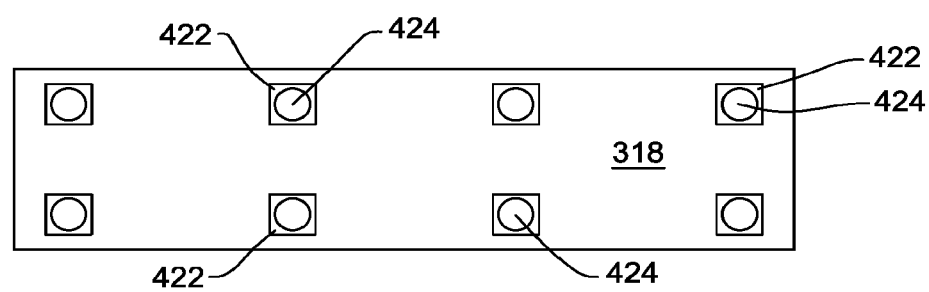
FIG. 56 is a plan view of a single control module.
Figure 57:
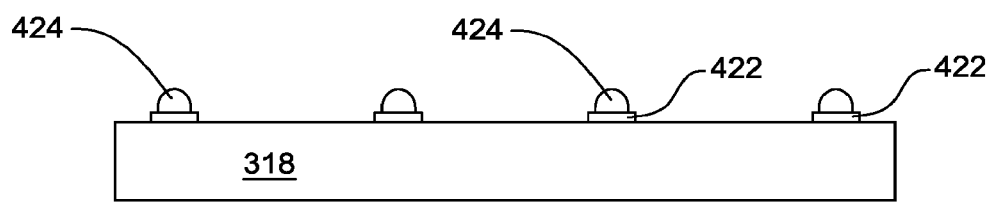
FIG. 57 is a side view of a single control module.

Semiconductor fabrication techniques not part of the current invention are employed to fabricate the control modules 318. As represented by FIG. 55, typically, plural control modules 318 are formed on a single silicon wafer 420. Often, wafer 420 has an initial thickness of approximately 550 microns. During the processes of module formation, each control module 318 is typically formed to have a number of bond pads 422 as seen in FIGS. 56 and 57. In FIG. 57 the bond pads 422 are shown as being elevated relative to the adjacent surface of the module with which the pads are integral. This is for ease of illustration only. Often the bond pads 422 are essentially flush with the surrounding surface of the control module 318. Each bond pad 422 is a location on the surface of the module 318 wherein a specific signal is applied to or outputted from the module. While the control modules 318 are still integral with wafer 420, electrically conductive solder bumps 426 are deposited over each bond pad 422. Solder bumps 426 are formed from gold and are applied to the associated bond pads 422 by a bump bonding process. Each solder bump 426 typically extends approximately 12 microns above the associated bond pad 424.

Once solder bumps 424 are formed, the overall thickness of the wafer 420 is reduced. This step is performed by back grinding and polishing the face of the wafer opposite the face on which the control modules 318 are formed. This back grinding and polishing is performed to remove the silicon so that the overall thickness of the wafer is reduced to approximately 50 microns. Wafer 420 is then diced to remove the individual control modules 318. After conventional testing, the control modules 318 are ready for bonding to the substrates 320.

Both the substrates 320 and superstrates 336 are formed from electrically insulating rigid members that have at least one non-porous layer. In one version of the invention, substrates 320 and superstrates 336 are both formed from a low temperature cofired ceramic. Often, one or both of substrate 320 and superstrate 336 are formed out of multiple layers of ceramic using processes that are not part of this invention. As is apparent from the description above, electrode array 310 includes plural substrates 320 and plural superstrates 336. There is one substrate-superstrate pair for each pair of contiguous tabs 314. Accordingly, it is the practice to simultaneously fabricate the plural substrates 320 together as single ceramic wafer. The plural superstrates 336 are likewise formed together on a common ceramic wafer. (Wafers not illustrated.) Each wafer typically has an initial thickness of 500 microns.

Figure 58:
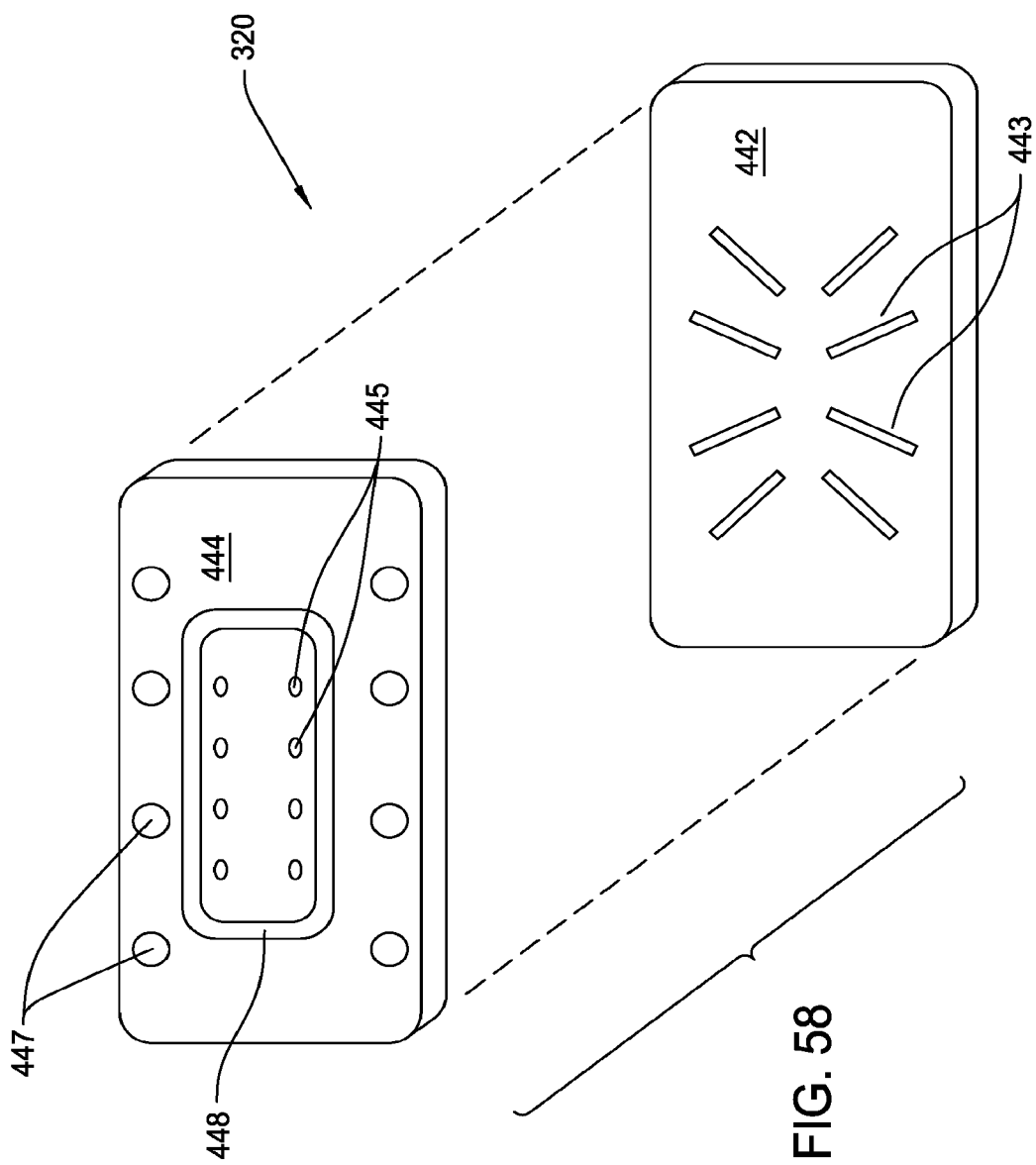
FIG. 58 is an exploded view of the plural layers of a substrate of the electrode array of FIG. 51.

Plural layers of low temperature cofired ceramic may be used to form each wafer. Specifically with regard to the substrate 320, a bottom layer of ceramic material, layer 442 in FIG. 58, is provided with conductive traces 443. The topmost layer of the substrate forming ceramic, layer 444, is provided with electrically conductive vias 445 and 447. Vias 445 are positioned so that when the control module 318 is positioned on the substrate 320, the control module stud bumps 426 are disposed over the exposed faces of the vias 445. Each via 445 extends through the associated ceramic layer 444 to the end of one of the conductive traces 443. Each via 447 extends though ceramic layer 444 to an end of a conductive trace 443 opposite the end to which a complementary via 445 abuts. For ease of illustration, conductors 443 and vias 445 and 447 are seen only in FIGS. 58, 59 and 78.

The top most substrate wafer-forming ceramic layer is further formed to have on its exposed face a metal ring 448. Substrate ring 448 is in the form of a rectangle with rounded corners. Ring 448 is dimensioned so that the control module 318 can be disposed within the ring and, when the control module is positioned there is a spacing of at least 100 microns from the control module and the ring. Further, each substrate 320 is formed so that the exposed faces of vias 445 are within ring 448. Vias 447 are positioned to so as to have exposed faces spaced beyond the outer perimeter of substrate ring 448.

Once the wafer containing the plural substrates 320 is formed, the overall thickness of the wafer is reduced. This process is performed by back grinding the outer face of the wafer, the side opposite the face to which the vias 445 and 447 extend and on which the ring 448 is formed. In some versions of the invention, this back grinding is performed to reduce the thickness of the substrate-carrying wafer to 100 microns.

Figure 59:
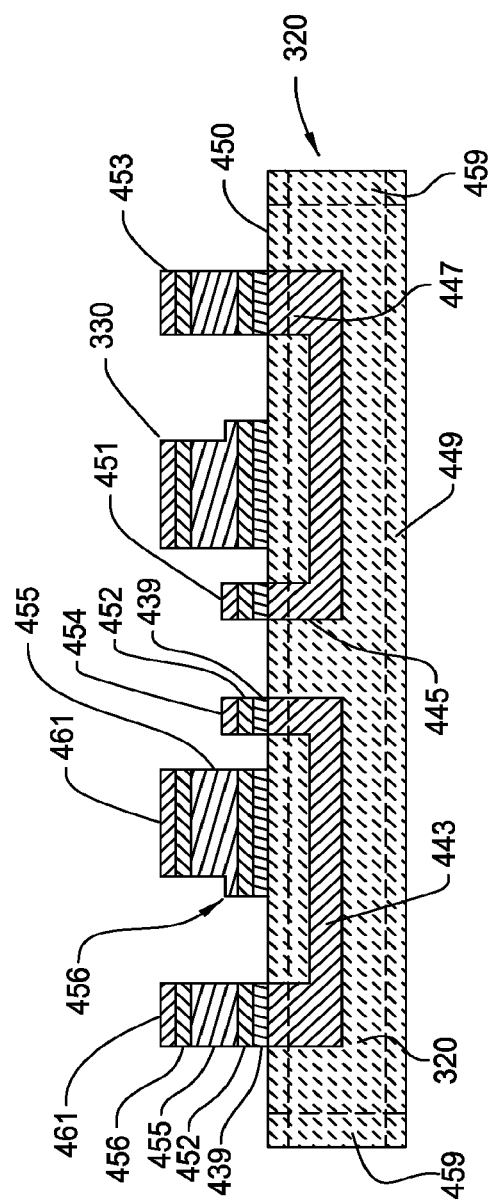
FIG. 59 is a cross sectional view of the substrate of FIG. 58 after solder plugs and a solder ring are deposited on the substrate.

The outer face of the substrate carrying wafer is then polished. Often, this polishing is a two-step process. In the first step, a low grit abrasive paper is applied to the face at a relatively low speed. This results in a fine layer of ceramic particles forming on the outer face of the wafer. Then, a higher grit abrasive paper is applied to the wafer at a higher speed. The heat generated by this polishing step causes the ceramic material to which the abrasive paper is applied to enter a semi-solid. This ceramic material, both the material still part of the wafer and the free particles, fuse together to form a non-porous barrier layer immediately below the outer surface of the wafer. In FIG. 59, this non-porous layer is illustrated as layer 449, the layer below the lower most dashed line that extends horizontally across substrate 320. Given the non-porous nature of this layer 449, this layer forms essentially a liquid and gas tight barrier over the outer surface of the substrate 320. For ease of illustrate this non-porous layer 449 is only illustrated in FIG. 59.

In some methods of manufacture of this invention, the inner surface of substrate carrying wafer is also polished. This surface is polished using the previously described steps to polish the wafer outer surface. Interleaved with the actually polishing steps is the rinsing of the substrate-carrying wafer. This rinsing removes debris including any gold separated from the vias 445, 447 and substrate ring 448. As a consequence of the wafer being exposed to this polishing, a non-porous barrier layer forms immediately below the inner surface of the wafer. In FIG. 59, this surface is illustrated as layer 450, the layer above the top most dashed line that extends across the substrate 320. Layer 450, like layer 449, forms a barrier layer that, if not gas tight is liquid tight. Again, for ease of illustration only, layer 450 is only illustrated in FIG. 59.

Once the polishing of the substrate-carrying wafer is complete, containment ring 330 and solder plugs 451 and 453 are formed on the inner surfaces of the individual substrates 320. Containment ring 330 is disposed over substrate ring 448, (interface not seen in FIG. 59). Each solder plug 451 is disposed one of the vias 445. Each solder plug 453 is disposed over one of the vias 447.

Containment ring 330 and solder plugs 451 and 453 each includes a layer of titanium 439 disposed directly over the gold face of the underlying via 445 or 447. The titanium layers 439 are at least 300 Angstroms thick. Titanium layers 439 are applied by a vapor deposition process. A platinum layer 452 500 Angstroms thick is applied over the titanium layer 439 by a vapor deposition process. A layer of gold 454, approximately 5 to 20 microns thick is applied over the platinum layer 452 by an electroplating process. The depositing of the gold layers 454 completes the formation of solder plugs 451. In FIG. 59, only the gold layer 454 associated with a single one of the solder plugs 451 is identified.

Fabrication of the containment ring 330 and solder plugs 453 continues with the application of an additional gold on gold layers 454. This gold is applied by a second electroplating process. This gold combines with the gold of layers 454 to provide the containment ring and each of the solder plugs 453 a gold layer, layer 455 in FIG. 59, that has a thickness, (a height) of approximately 50 microns. This second layer of gold is not applied to the whole of the gold layer 454 initially deposited on the substrate to form the containment ring 330. This gold is deposited inwardly approximately 25 microns of the outer perimeter of the layer 454. These contiguous gold layers of containment ring 330 define a step 456, seen only in FIGS. 59, and 70, that is located inwardly of the outer perimeter of the containment ring.

Layers of platinum 456 and gold/tin solder 461 are applied to the top surface of the gold layers 455. Platinum layer 457 has the same thickness as platinum layer 454 and is applied by the same process employed to deposit layer 454. The gold/tin solder layers 461 have a thickness of 25 microns and are applied by an electroplating process.

Gold layers 454 provide height to the solder plugs 451. Gold layers 455, combined with the gold of layers 454 provide height to both the containment ring 330 and solder plugs 453. During subsequent thermal compression processes described below, solder layers 461 integral with the solder ring 452 liquefies to bond to shell 344. Solder layers 461 bond with superstrate solder plugs 471 to form posts 344. Platinum layers 457 prevent the gold internal to the layer 455 from leaching into the solder. Platinum layers 452 prevent upward leaching of the titanium of layers 439. The titanium layers 439 themselves are provided because they adhere well to both the gold of the underlying vias 445 and 447 and ring 448 of the substrate 320 and to platinum. For ease of illustration, other than in FIG. 59, containment ring 330 and solder plugs 451 and 453 are shown as single metal members.

Once the solder plugs 451 and 453 and the solder ring 452 are formed on the substrates 320, the substrate-carrying wafer is diced. The dicing separates the wafer into the individual substrates 320. During the dicing process, the saw that performs the dicing heats the sides surfaces of the substrates 320. These surfaces are heated to the level where the ceramic material forming the outer side layers transitions to the semi-solid state. As when the ceramic is polished, this heating allows the outer layer of ceramic material to fuse together so as to form a non-porous barrier layer. In FIG. 59, these layers 459, shown immediately inward of the outer side surfaces of the substrate 320. For ease of illustration, these non-porous layers are only illustrated in FIG. 59.

Figure 60:
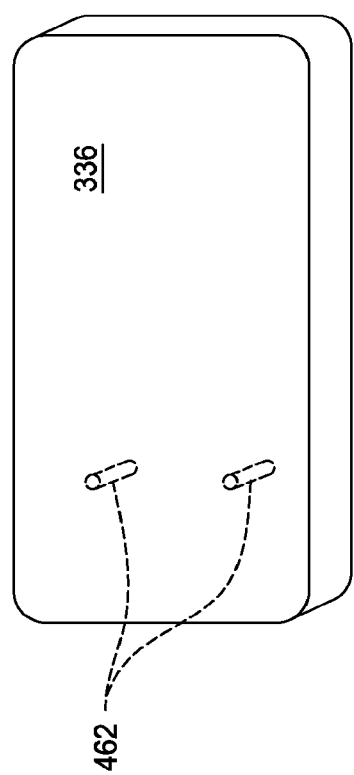
FIG. 60 is a perspective view of a superstrate of the electrode array of FIG. 51.

The ceramic wafer forming the superstrates 336 is fabricated so that, as seen in FIG. 60, each superstrate has two conductive vias 462. Each superstrate 336 is formed so that each via 462 extends top to bottom, through the superstrate. More specifically, each via 462 is located under an outer surface of the superstrate over which a separate one of the electrodes 316 is subsequently formed. For ease of illustration, each via 462 is seen only in FIG. 60.

Figure 62:
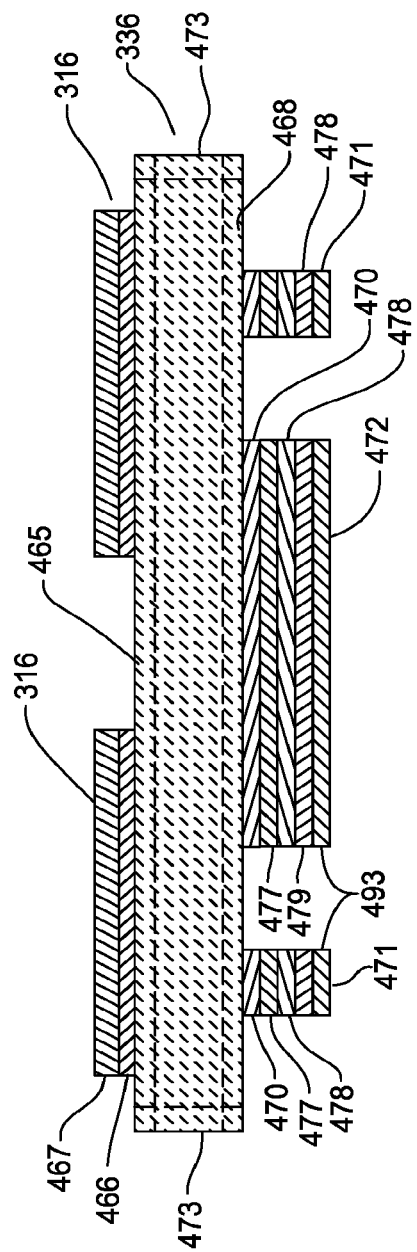
FIG. 62 is a cross sectional view of the substrate of FIG. 60.

Once the superstrate-carrying wafer is formed, the outer surface of the wafer, the surface on which the outer surfaces of the superstrates 336 lie, is polished. This surface is polished using the same polishing steps used to polish the substrate-carrying wafer. This polishing is performed to form non-porous outer layers on the superstrates 336. One such layer, layer 465 is seen in FIG. 62 as being the layer of superstrate-forming ceramic above the top most dashed line that extends across the superstrate 336.

Once the superstrate 336 is polished, the electrodes 316 are formed on the outer surface. Fabrication of the electrodes 316 starts with the depositing of gold layers 466 on the exposed faces of barrier layers 465. Gold layers 466 are applied by electroplating or thick film screen deposition process and have a thickness of at least 250 microns. It should be appreciated that each one of the gold layers 466 overlies and bonds with the exposed face of one of the superstrate vias 462. Gold layers 466 are applied to the superstrate because the gold adheres well to the exposed face of the ceramic barrier layers 465. A layer of iridium, layer 467, is deposited over each of the gold layer 466. The iridium is applied to a thickness of at least 5 microns. The iridium is applied by a sputter process. The iridium forms the low-impedance high charge capacity exposed face of each electrode. Collectively, each gold layer 466-iridium layer 467 laminate forms a single electrode 316. In one version of the invention, each electrode 316 has a surface area of approximately 1.0 mm by 4.0 mm. The two electrode 316 are deposited on the superstrate-carrying wafer are deposited so that the two electrodes 316 that form the pair of electrodes on a single superstrate 336 are spaced apart by at least 250 microns. In the Figures other than FIG. 62, for ease of illustration only, electrodes 316 are shown in cross section as consisting of a single metal layer.

The overall thickness of the substrate-carrying wafer is then reduced. Specifically, using a back grinding process the overall thickness of this wafer is reduced to approximately 100 microns. This process is performed on the inner side of the wafer, the side with the faces of the substrates 336 that will eventually be directed toward carrier 318 and the control modules 318. Then, using the previously discussed polishing process, the inner side of the wafer is polished to form a non-porous layer. This layer is called out in FIG. 62 as layer 468 below the lower of the two dashed lines that extends across the superstrate 336.

Non-porous superstrate layers 465 and 468, like non-porous substrate layers 449 and 450 are liquid tight if not gas tight.

Figure 61:
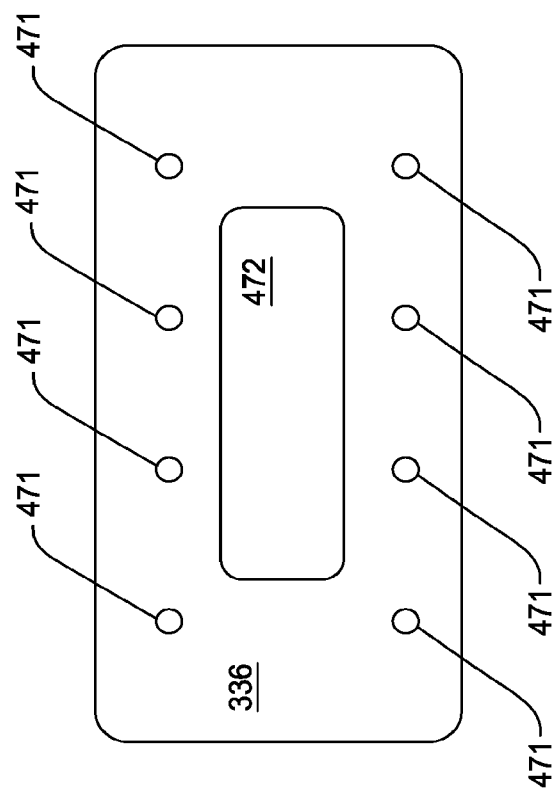
FIG. 61 is a plan view of the inner surface of the substrate of FIG. 60.

Solder plugs 471 and 472 are then formed on the inner surface of the superstrate-carrying wafer. As seen in FIG. 61 there are plural small sized solder plugs 471 and one large sized solder plug 472. Two of the solder plugs 472 are disposed on the exposed faces of the vias 462 that extend through the substrate. (Interface not illustrated.) Three additional solder plugs 471 are formed on the face of substrate layer 468 so as to be in line with each via-covering solder plug 472. Solder plug 472 is in between the two rows of solder plugs 471. Solder plug 472 is positioned so that when the superstrate 336 is disposed over the substrate 320, the plug 472 is disposed over lid 332. Solder plug 472 is formed to have an outer perimeter that extends between 5 to 150 microns outwardly from the outer perimeter of the lid 332.

Solder plugs 471 and 472 are formed by initially applying a layer 470 of titanium on the locations on the substrate layer 468 on which the plugs are to be formed. This includes the exposed faces of the vias 462. The titanium is deposited using vapor deposition process layers so as to have a thickness of at least 300 Angstroms. Platinum layers 477 having a thickness of 500 Angstroms are applied over the titanium layers 470. Platinum layers 477 are applied using a vapor deposition process. Gold layers 478 have a thickness of at least 10 microns are applied over the platinum layers 477 using an electroplating process. Platinum layers 479 are deposited over gold layers 478. Platinum layers 479 have the same thickness as platinum layers 477 and are applied using the same process used to deposit layers 477. Gold/tin solder layers 493 that have a thickness of at least 10 microns are deposited over platinum layers 479 using an electroplating process.

Titanium layers 470 are applied because they adhere well to both ceramic and the subsequently applied metal. Platinum layers 477 and 479 are applied to prevent the gold of layers 478 from leaching during the subsequent solder bonding process. The gold layers 478 themselves provide height to the solder plugs 471 and 472. The gold/tin alloy of solder layers 493 are the layers of the solder plugs 471 and 472 that actually bond with the structural members against which the plugs later abut.

At this stage in the process of fabricating the superstrates 336, the superstrates are ready for separation from the wafer. This process is performed by dicing the wafer. The saw employed to separate the substrates 336 from the wafer, and from each other, heats the surfaces of the substrates to which the saw is applied. This heating causes the material forming to substrate to transition to a semisolid state and fuse together. This fused ceramic material thus forms non-porous layers along the side surfaces of the superstrate 336. In FIG. 62 these layers are called out as layers 473. Layers 473, like layers 465 and 468, prevent at substantially all liquid flow, if not gas flow, into the center of the superstrate 336.

Figure 63:
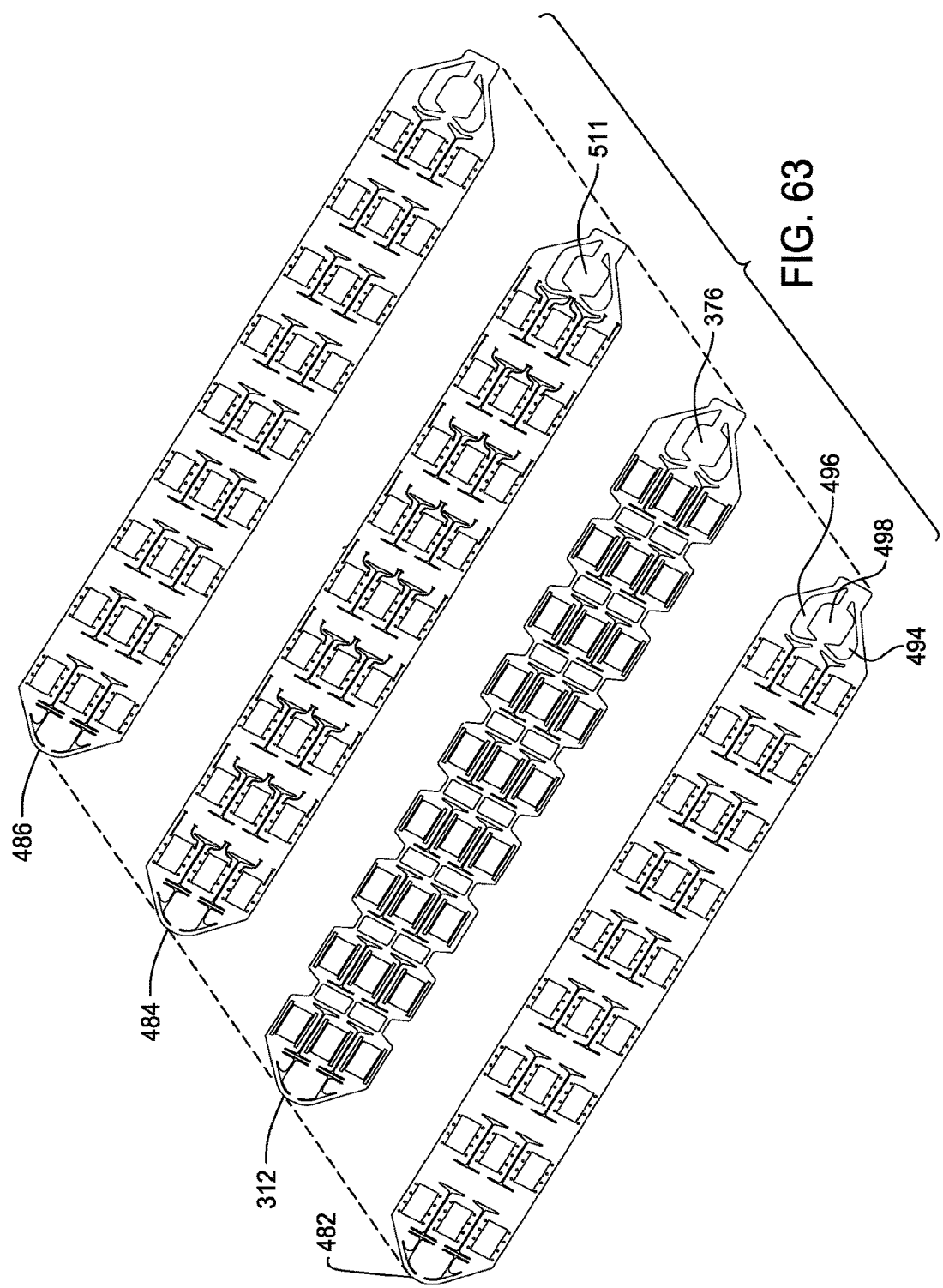
FIG. 63 is an exploded view of the layers forming the carrier-laminate subs-assembly of the electrode array of FIG. 51.

FIG. 63 illustrates how the carrier 312 is embedded in the electrically insulating laminate 340. The laminate 340 consists of three layer of flexible, electrically insulating material, here liquid crystal polymer (LCP). Laminate 340 includes a bottom layer 482, a middle layer 484 and a top layer 486. Each layer 482, 484 and 486 has a thickness of approximately 25 microns. As seen by reference to FIG. 64, collectively, carrier 312 and laminate 340 are assembled so that the carrier is disposed between the bottom and middle laminate layers 482 and 484, respectively.

Figure 65:
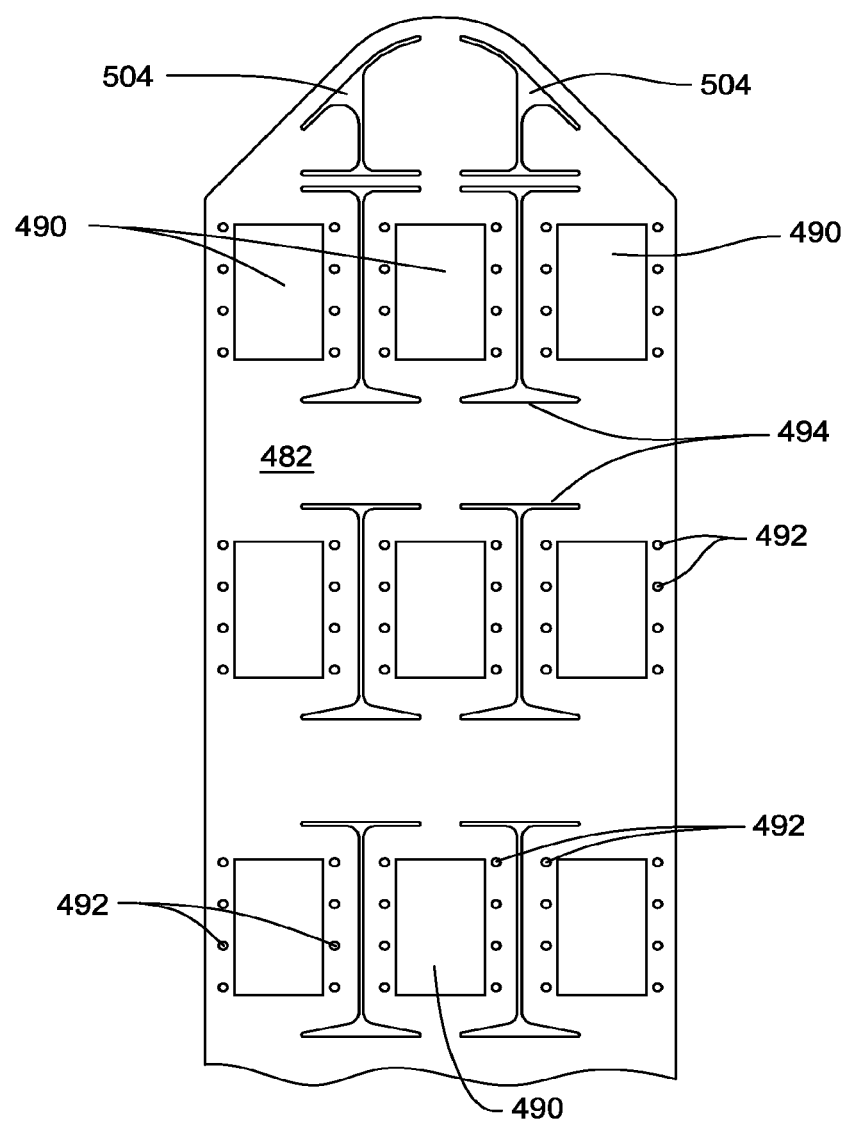
FIG. 65 is a plan view of the distal end of the upper layer of electrically insulating material of the carrier-laminate sub-assembly of FIG. 63.

The features of laminate bottom layer 482 are now described by reference to FIG. 65. Layer 482 has an outer perimeter with a shape similar to that of the carrier 312 disposed over the layer. While carrier 312 and laminate layer 482 have the same generally shape, the laminate layer has a surface area slightly larger than that of the carrier 312. Specifically the relatively dimensions of these components are such that when the carrier 312 is disposed over the laminate layer 480, the laminate layer extends approximately 25 microns beyond the outer perimeter of the carrier. Also, unlike the carrier 316, the sides of the laminate bottom layer 482 do not bend inward at the locations where tabs 314 are not present.

Laminate layer 482 is further formed with plural, longitudinally spaced apart rows of rectangular windows 490. Laminate layer windows 490 correspond in number and arrangement to carrier windows 404. The laminate layer window 490 have shape and a cross sectional area that corresponds to the shape and area of the carrier windows 404. Adjacent the longitudinal sides of each window 490, laminate layer 482 is further formed to have a row of openings 492. Openings 492 are located so that when the adjacent laminate window 490 is in registration with a carrier window 404, one row of openings is centered under the complementary carrier window 402 and the second row of openings is centered under the complementary carrier window 406. Openings 492 are circular in shape. The openings 492 have a diameter that is approximately 10 microns less than the width across the associated carrier window 402 or 406.

The bottom laminate layer 482 is also shaped so as to have plural I-shaped slots 494. Within each row of windows 490 there are two slots 494. Each slot 494 is located between the two windows 490 that form a pair of adjacent windows 490. Each slot 494 is located so that when a row of laminate windows 490 is in registration with a row of carrier windows 404, each slot is in registration with the I-shaped slot 387 between adjacent carrier tabs 314. The widths across the sections of each slot 490 are approximately 25 microns less than widths across the corresponding sections of the carrier slots 387.

Laminate layer 482 is further formed to have forward of the distal end, two asymmetrically shaped windows 495 and 496. Windows 495 and 496 define a tab 498 (FIG. 63) internal to the laminate layer that will overlie carrier tab 376. The distal end of laminate layer 482 is formed to have two slots 504. Slots 504 have shapes that correspond to the void spaces in the carrier 312 between the head 392, shoulders 394 and proximal most beams 388. Slots 504 are approximately 25 microns less in width than the underlying void spaces in the carrier 312.

The middle layer of laminate 340, layer 484 has the same basic shape and features as layer 482. The dimensions of the features of middle layer 484 are identical to those of bottom layer 482. Layer 484, now described by reference to FIG. 66, is formed with windows 508 and slots 509 and 510. Middle layer 484 windows 508 and slots 509 and 510, correspond, respectively to, bottom layer 482, windows 490 and slots 494 and 504. Laminate middle layer 484 is further formed with through openings 512 that correspond in number and position to openings 492 internal to layer 482.

Laminate layer 484 is further formed to have slots 514 essentially identical to slots 494 internal to layer 482. It can be seen from FIG. 63 that laminate layer 484 is further shaped to define a tab 511 analogues to the tab 498 integral with layer 482.

Conductors 342 and complementary capture pads 515 are formed on laminate middle layer 484. The capture pads 515 are disposed around layer openings 512. Capture pads 515 are ring shaped and disposed on the outwardly facing surface of layer 482, the surface directed away from the control module 318. The conductors 342 extend to the capture pads 515. In FIG. 66, for ease of illustration, only a few of the conductors 342 that extend away from just several of the capture pads 515 are illustrated.

Figure 66A:
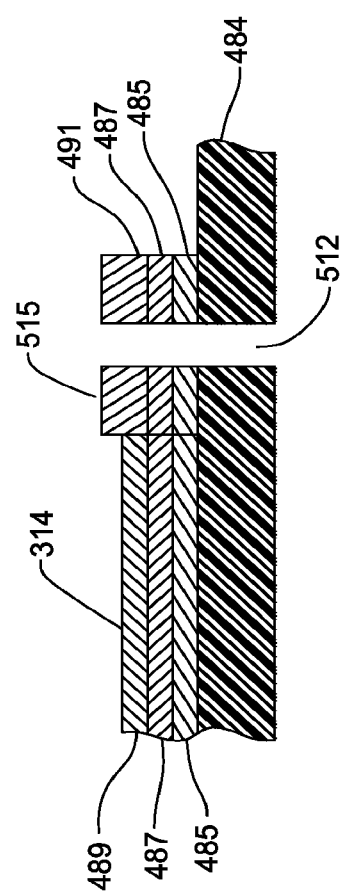
FIG. 66A is a cross sectional view of the layers forming the conductors and capture pads integral with laminate middle layer.

Each conductor 342 and capture pad 515 is in form of a laminate structure as seen in FIG. 66A. Both the conductors 342 and capture pads 515 have bottom layers 485 formed from titanium. Titanium layers 485 have a thickness of at least 300 Angstroms and are applied using a vapor deposition process. Conductors 342 and capture pads 515 have common co-planar gold layers 487. Gold layers 487 have a thickness of at least 2 microns and are applied using an electroplating process. Conductors 314 have a top layer, layer 489 of titanium. Layer 489 has the same thickness as titanium layer 485 and is applied using the same process. Capture pads 515 have a top layer, layer 491 formed from platinum. The platinum of layer 481 has a thickness of at least 1 micron and is applied using a vapor deposition process.

Titanium layers 485 are provided because titanium adheres well to both LCP and gold. The gold of layers 487 are the highly conductive layers of the conductors 314 and capture pads 515. The conductors 314 are provided with the top most titanium layers 489 because the titanium bonds well to the laminate top layer 486 that is subsequently affixed over the conductors. As described below, in a later step of the process of assembling electrode array 310, capture pads are bonded to superstrate solder plugs 471. During this bonding process, the platinum outer layers 491 of the capture pads 515 prevent the underlying gold from leaching.

Laminate top layer 486 is essentially identical in shape to laminate bottom layer 482. The outer perimeter of the top layer 486 has the same dimensions as the bottom and middle layers 482 and 484, respectively. Most of the windows, slots and openings in laminate top layer 486 are identical dimensions to those in the bottom layer 482. Accordingly, these identical features are not called out. One difference between the two layers 482 and 486 is the openings 518 in top layer 486, identified in FIG. 64. Openings 518 correspond to the openings 492 in bottom layer 482. A difference between the two sets of openings is that openings 518 are appreciably larger in diameter than openings 492. Generally, it should be appreciated that openings 518 are larger in diameter than the diameter of the capture pads 515. In some versions of the invention, top layer openings 518 have a diameter 25 microns or greater than the diameter than the middle layer capture pads 515.

Figure 67:
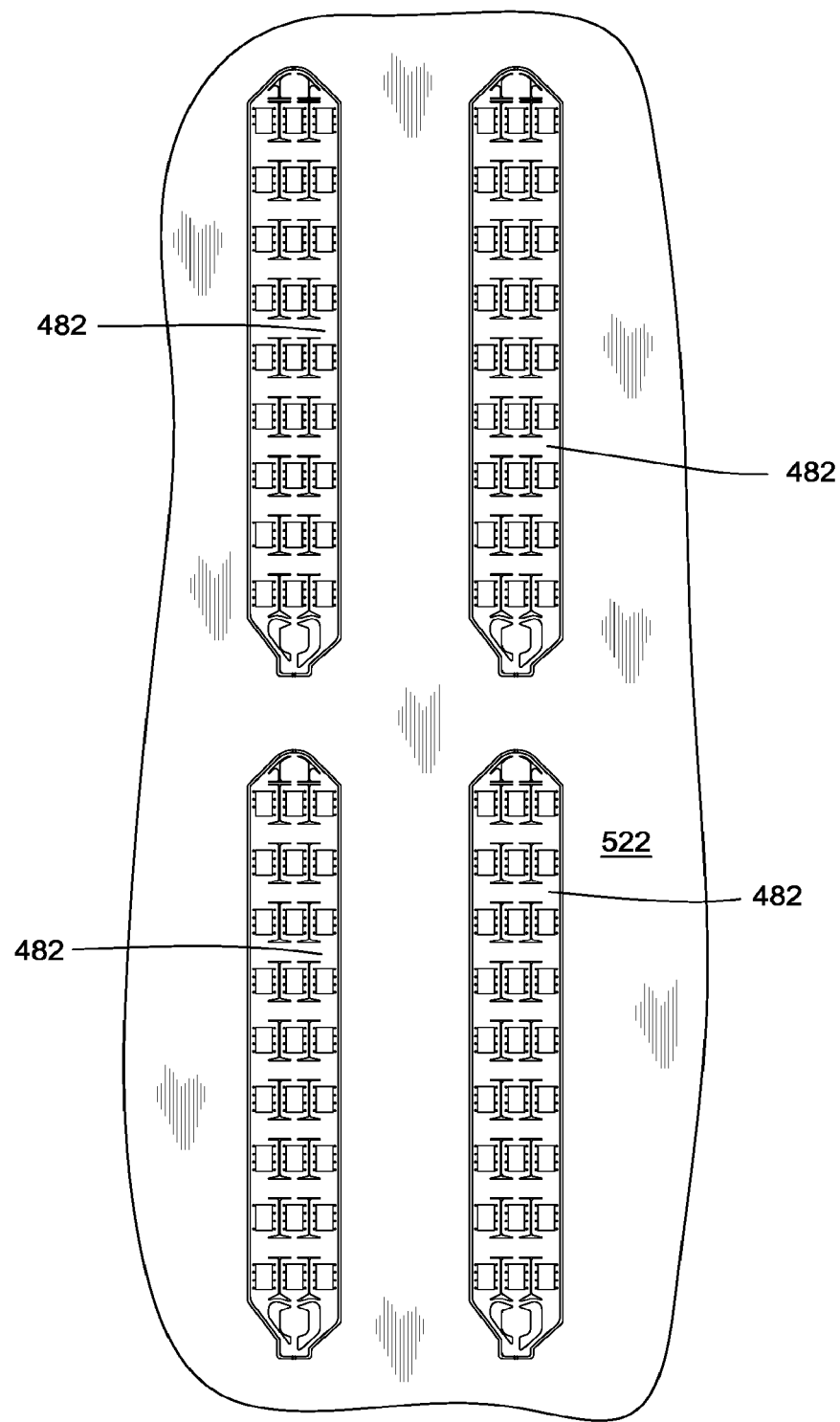
FIG. 67 depicts how plural layers, here plural bottom layers, appear on a sheet of insulating material prior to the separation of the layers from the sheet.

To facilitate the batch manufacture of electrode arrays 390 of this invention, typically plural laminate 340-forming layers are formed on a single sheet of LCP. As represented by FIG. 67, plural bottom layers 482 are formed on a single sheet 522 of LCP. Openings are formed in the sheet 522 to form the features of the individual layers 482 by a laser etching process. While only partially shown in FIG. 67, small tabs (not identified) hold the essential formed laminate layers 482 to the rest of the sheet 522. Sheets of LCP similar to sheet 522 are shaped to form, respectively, the plural middle layers 484 and plural top layers 486.

The carrier-laminate sub-assembly is fabricated by placing the carrier-containing coupon 370 over the LCP sheet on which the laminate bottom layers 482 are formed. The LCP sheet on which the laminate middle layers 484 are formed is placed over the exposed face of the coupon 370. The LCP sheet on which the laminate top layers 486 are formed is placed over the exposed face of the middle layer sheet. Thus, the sheet of upper laminate layers 486 is disposed immediately over conductors 342. As a consequence of this arrangement, it should be understood that the carrier windows 404 are in registration between the laminate layer windows 490 and 508. The large windows integral with top laminate layer 486 are immediately above the middle layer windows 508.

The laminate layers 482, 484 and 486 are then bonded together using a vacuum controller thermal compression process. As a consequence of this process, as seen in FIG. 64, the ends of the laminate bottom and middle layers 482 and 484, respectively that project beyond the outer perimeters of the carrier tabs 314 bond together. Each carrier 312 is thus partially encapsulated within the surrounding laminate layers 482 and 484. The side surfaces of the carrier 312 that defines windows 404 are not so encapsulated. These surfaces of each carrier are electrically shielded by oxide coating 414.

Also as a consequence of this bonding process the laminate top layers 486 are bonded over the laminate middle layers 484. Conductors 342 are sandwiched between laminate layers 484 and 486. In FIG. 64, for ease of illustration, conductors 342 are not shown. Owing to the relative dimensioning of middle layer openings 512 and top layer openings 518, capture pads 515 are exposed.

LCP layers 482, 484 and 486 forming laminate 340 are not formed so as to be continuous between the adjacent longitudinally spaced apart slots 494. Thus, when the laminate 340 is bonded over and under the carrier, sections of LCP extend over the void spaced between longitudinally adjacent carrier beams 388. These unbroken sections of laminate form membranes 528 (FIG. 51) that extend under/over the interior sections of the carrier. These membranes 528 are analogues to membranes 70. Similarly, unbroken sections of laminate extend longitudinally between the longitudinally adjacent tabs that form the two opposed outermost rows of tabs. These sections of laminate function as membranes 529 (FIG. 51) analogues to membranes 72.

Figure 68:
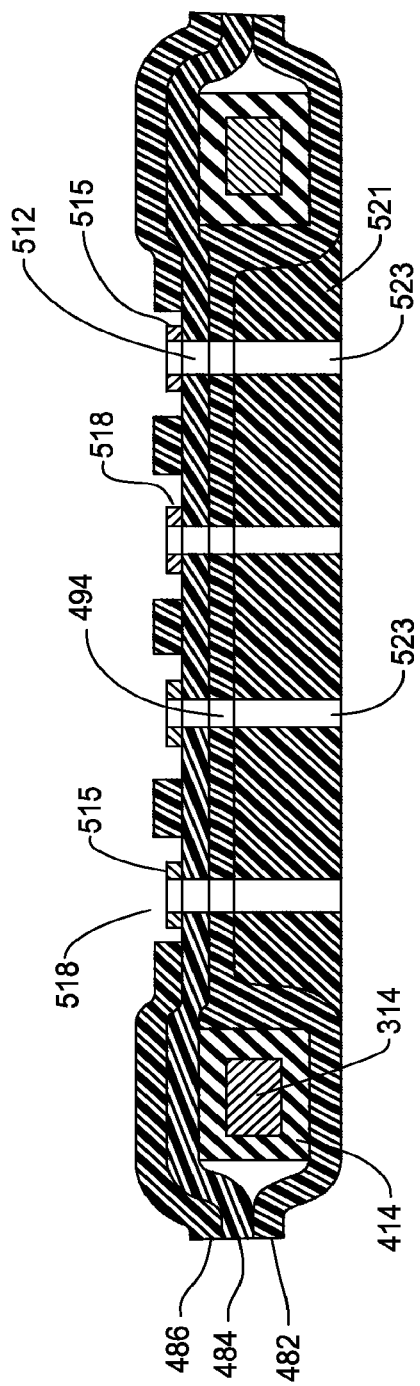
FIG. 68 is a cross section through the carrier-laminate sub-assembly along a longitudinal axis through one of the carrier tabs.
Figure 69:
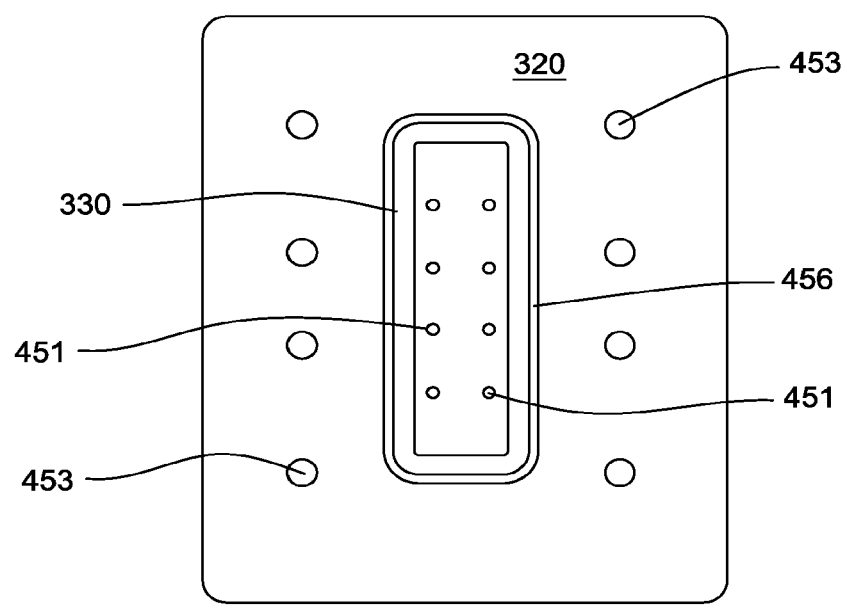
FIG. 69 is a plan view of the containment ring bonded to the substrate.

As a further result of the encapsulation of carrier 312 in laminate 340, laminate layers 482, 484 and 486 extend over and under carrier windows 402 and 406 as seen in FIG. 68. Within each window 402 and 404, the laminate layer 482 bonds to the overlying laminate layer 484. Owing to the registration of the laminate layers 482, 484 and 486 with each other, laminate bottom layer openings 492, middle layer openings 512 and upper layer openings 518 go in registration with each other. Further, as part of the carrier encapsulation, the laminate layers 482, 484 and 486 flex into the space defined by the carrier window 402 or 406. A plastic rib 521 is fitted into each window 402 and 404 adjacent the exposed surface of the laminate bottom layer. The rib 521 pushes the sections of laminate 340 disposed in the associated window 402 or 406 outwardly. Thus the tops of the laminate sections disposed over windows 402 and 406 are essentially flush with the surrounding sections of the laminate. On the substrate-facing surface side of the carrier-laminate sub-assembly, ribs 521 have exposed faces that are essentially flush with the adjacent surfaces of the laminate. Ribs 521 thus ensure that, when a carrier-laminate is disposed between a substrate 320 and a superstrate 336, essentially the whole of one face of the carrier-laminate abuts the substrate 320 while the whole of the opposed face abuts the superstrate 336.

Ribs 521 are formed with through bores 523. Bores 523 are positioned so that when the rib is fitted in a carrier window 402 or 406, the bore is aligned with the coaxial laminate openings 494.

Once the carrier-laminate sub-assemblies are formed, the assemblies are excised from the flexible coupon and the sheets of electrically insulating material.

Figure 70:
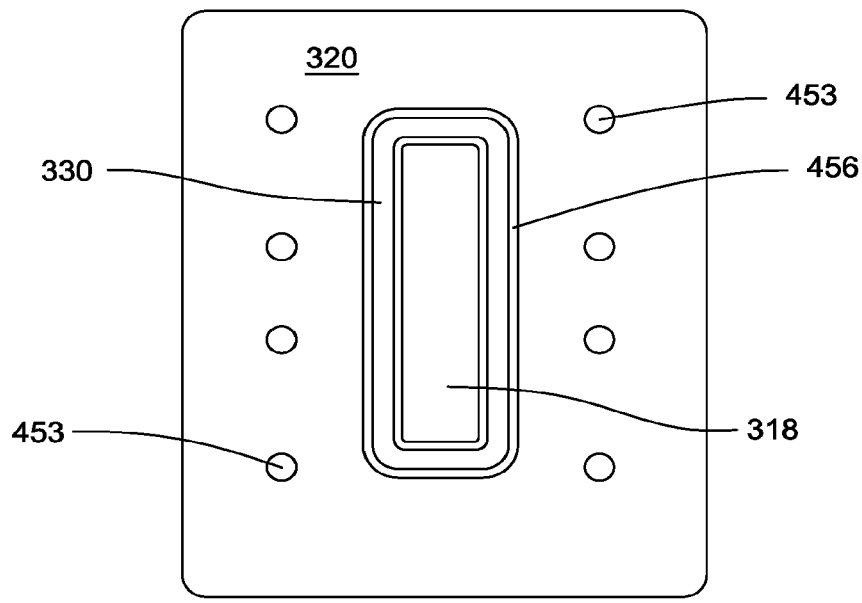
FIG. 70 is a plan view of the control module bonded to the substrate.
Figure 71:
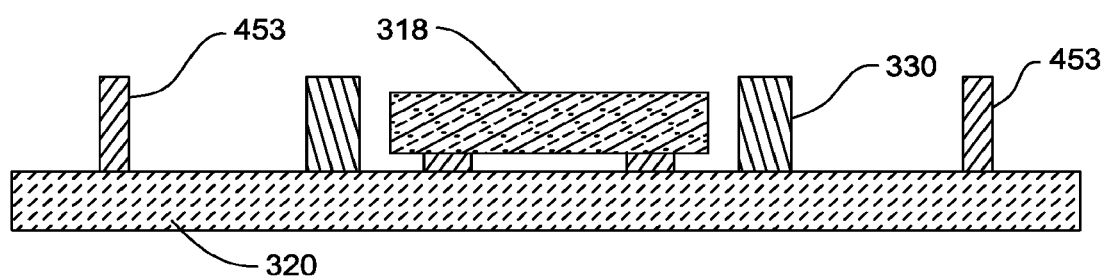
FIG. 71 is a cross sectional view of the control module bonded to the substrate.

The fabrication of the sub-assemblies forming the electrode array 310 into the array, as represented by FIGS. 70 and 71, starts with the bonding of the control module 318 to substrate 320. The control module 318 is disposed inside ring 330 so that the module stud bumps 424 are disposed over the substrate solder plugs 453 formed over vias 447. A thermal compression bonding process bonds the opposed contacting pairs of stub bumps 424 and solder plugs 453 together. This bonding both secures the control module 318 to the substrate 320 and establishes the electrical connections between the substrate bond pads 422 to the substrate vias 445. For ease of illustration, each bonded solder bump 424-solder plug 453 unit is shown as a single section of material.

Figure 72:
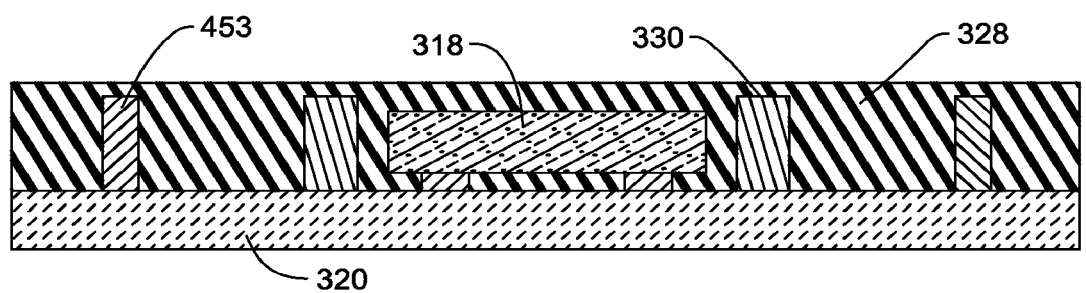
FIG. 72 represents the coating of oxide over the substrate.

Using a plasma deposition process, silicon oxide is then deposited on the inner surface of substrate 320. As seen by reference to FIG. 72, the silicon oxide 532 flows into the space between the control module 318 and ring 330. To the extent there are small space, typically, 15 microns or less, between the inner surface of the substrate 320 and the adjacent under surface of the control module 318, the silicon oxide 532 also flows into this space. In the Figures the separation between the control module 318 and the substrate 320 is exaggerated for the purposes of illustration. In this deposition process, the silicon oxide 532 is deposited so as to extend above ring 330. In some versions of the invention, the silicon oxide extends approximately 50 microns above the exposed face of ring 330. Silicon oxide is a conformal coating that, when deposited is substantially impenetrable to fluid flow therethrough.

Figure 73:
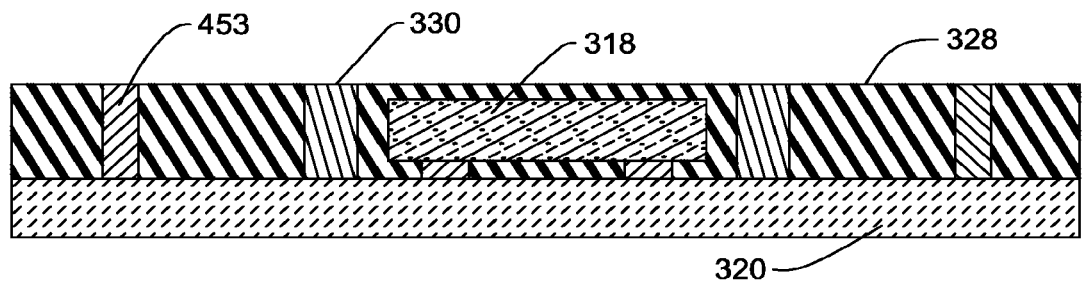
FIG. 73 depicts the substrate after the upper layer of oxide has been removed.

As illustrated by FIG. 73, the upper portion of the silicon dioxide layer 532 is then removed. This step may be performed by back grinding. More particularly, the silicon dioxide layer 532 is removed to the level at which the layer 532 is planar with the top of ring 330. This step is performed to ensure that, within the ring 330, the silicon dioxide layer 532 does not project above the ring 330 and is planner.

Figure 74:
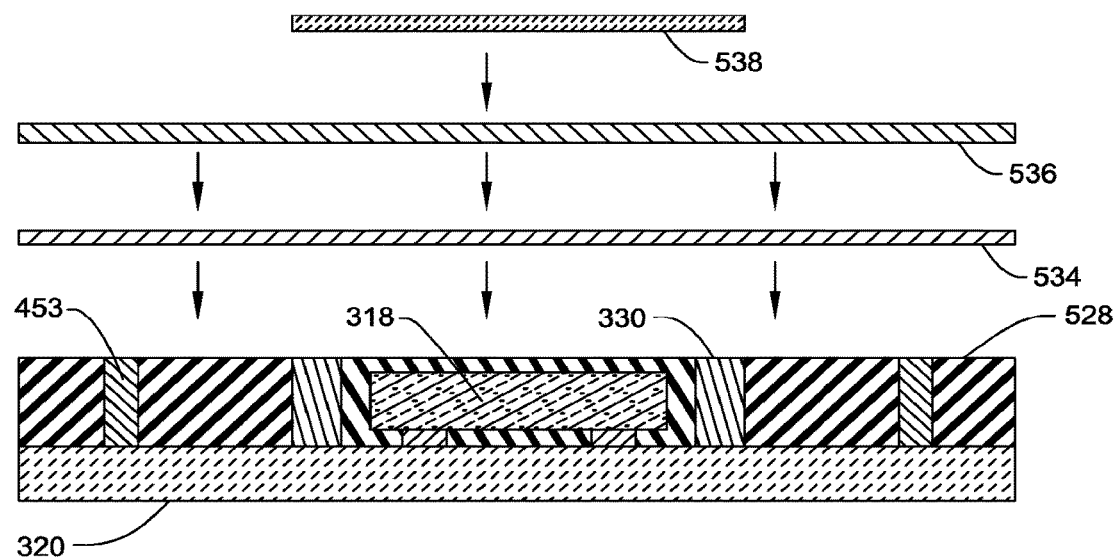
FIG. 74 represents the steps performed to form the lid over the control module and surrounding ring.

Lid 332 is then secured over ring 330. As represented by FIG. 74, an initial step in the mounting of lid 330 is the depositing of a layer of titanium 534 over the exposed face of the silicon oxide layer 532. Titanium layer 534 has a thickness of at least 0.3 microns and is deposited using a vapor deposition process. The titanium forming layer 534 bonds to the exposed face of ring 330 and the exposed face of the co-planar silicon dioxide layer 532. A layer of gold 536 approximately at least 0.3 microns thick is then applied over titanium layer 534 using a vapor deposition process.

Figure 77:
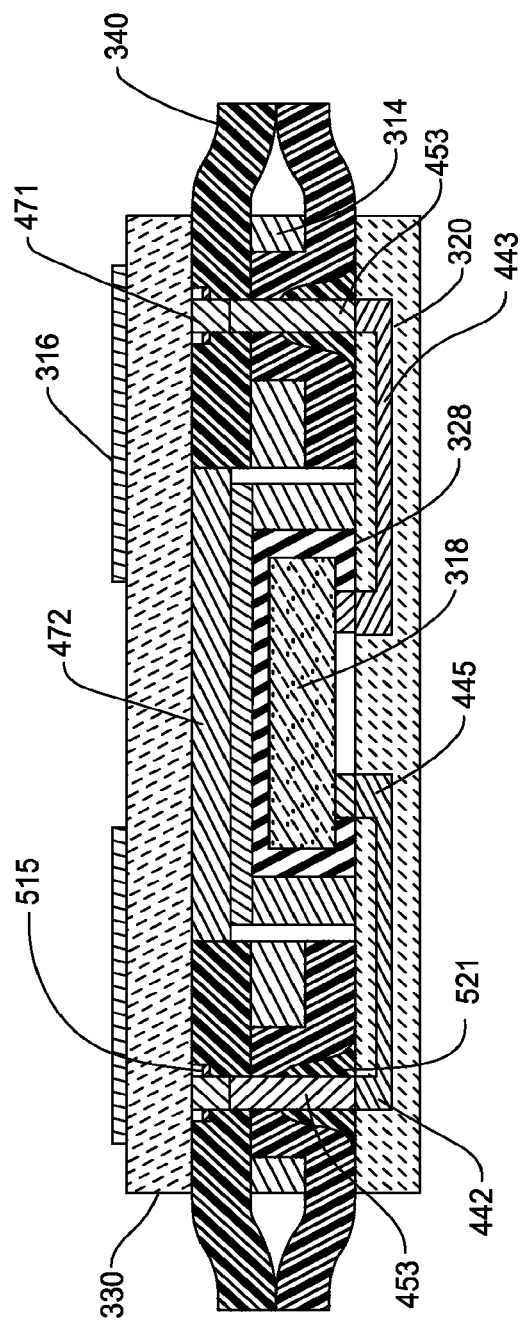
FIG. 77 is a detailed depiction of the opposed substrate and superstrate solder plugs prior to the plugs being bonded together to form a connecting post.
Figure 78:
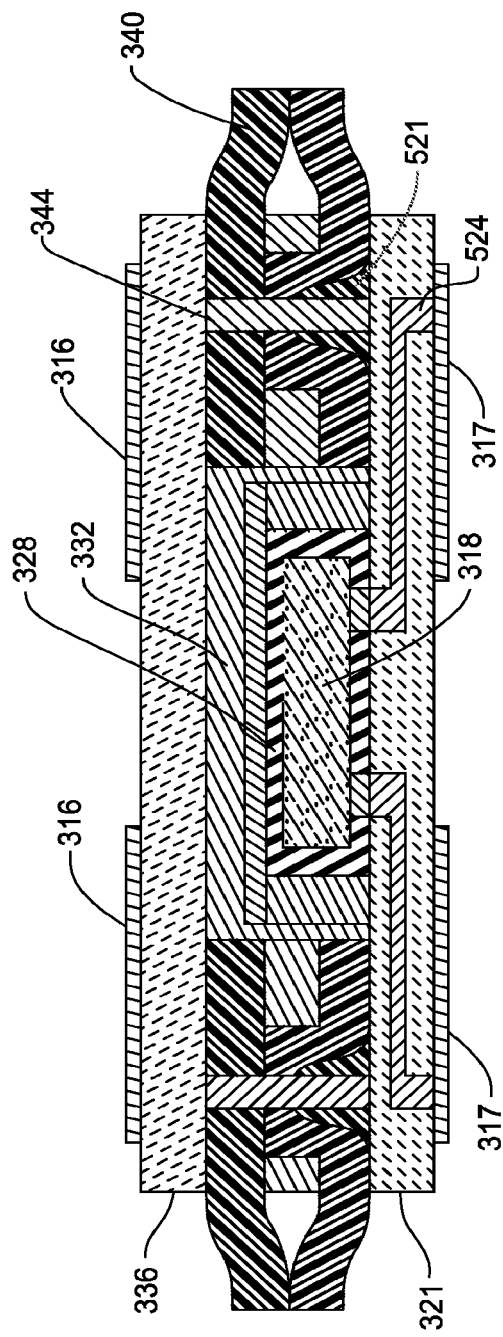
FIG. 78 is a cross sectional view of a variation of the second alternative version of the invention.

Titanium and gold layers 534 and 536, respectively are then removed other than where the lid 332 is to be bonded to the sub-assembly. This process is performed by first applying a layer of photoresist 538 over the exposed section of the gold layer 490 where the lid is to be affixed. This area is the area defined by and within ring 330. Using a chemical etching process, the titanium layer 534 and gold layer 536 are removed. At this time, while the photoresist layer 538 remains in place, using a reactive ion etching process, the silicon dioxide layer 532 not cover by the photoresist layer is removed. The remaining silicon oxide is the silicon oxide disposed within ring 330 below titanium and gold layers 534 and 536, respectively. This silicon oxide is now the shell 328 that surrounds the control module 318 as seen in FIGS. 53, 77 and 78.

As a consequence of the removal of the silicon oxide, the surface of the substrate 320 previously coated with this material is now exposed. Also re-exposed are solder plugs 453.

Figure 75:
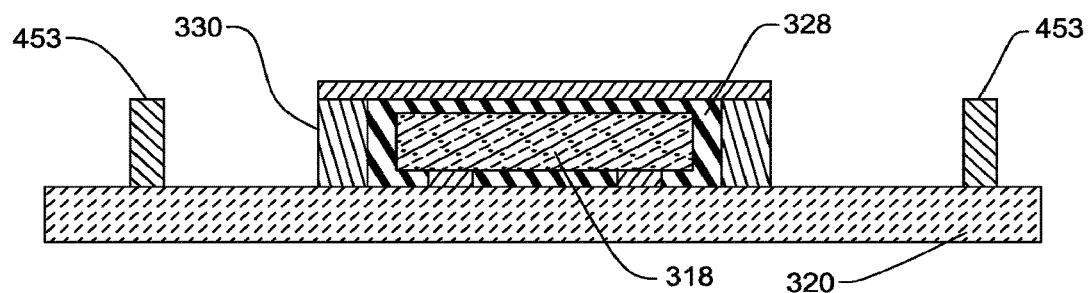
FIG. 75 illustrates how the substrate appears after the lid is in place.

The actual lid 332 is a preformed wafer of metal able to bond with the gold of layer 490. In one version of the invention, lid 332 is formed from gold. Lid 332 has a length and width that correspond to the outer perimeter of ring 330. The lid has a thickness of approximately 50 microns. A thermal compression bonding process is used to affix the lid 332 to the underlying gold layer 536 and, by extension, ring 330. For ease of illustration, in FIGS. 75 and 76 titanium and gold layers 534 and 536, respectively, are not illustrated.

Final assembly of electrode array 310 continues with the fitting of the substrate-module assemblies in a jig, step not illustrated. The jig is structured to hold the substrates 320 so they are in a pattern that corresponds to the pattern of carrier windows 404. Each substrate 320 is positioned so that the control module 318 bonded to the substrate is at a location that corresponds to the location of one of the carrier windows 404.

The carrier-laminate sub-assembly is then disposed over the substrate-control module sub-assemblies. As a result of this process, control modules 318 extend through the windows 490 internal to laminate bottom layer 482. The control modules 318 extend at least partially through the carrier windows 404. The portions of shells 328 disposed over the control modules 318 and lids 330 are seated in the space defined by middle laminate layer windows 508. These portions of the shells 328 and lids 330 may also extend a short distance into windows 508 internal to laminate top layer 486. Owing to the dimensioning of the components, at this time, the outer side surface if each ring 330 is spaced approximately 15 microns or less from the adjacent window-defining surfaces of both the carrier 318 and laminate 340.

As a further result of the seating of the carrier-laminate sub-assembly over the substrate-control module sub-assemblies, the substrate solder plugs 453 extend through rib bores 523, laminate bottom layer openings 494 and partially through the middle layer openings 512.

Figure 76:
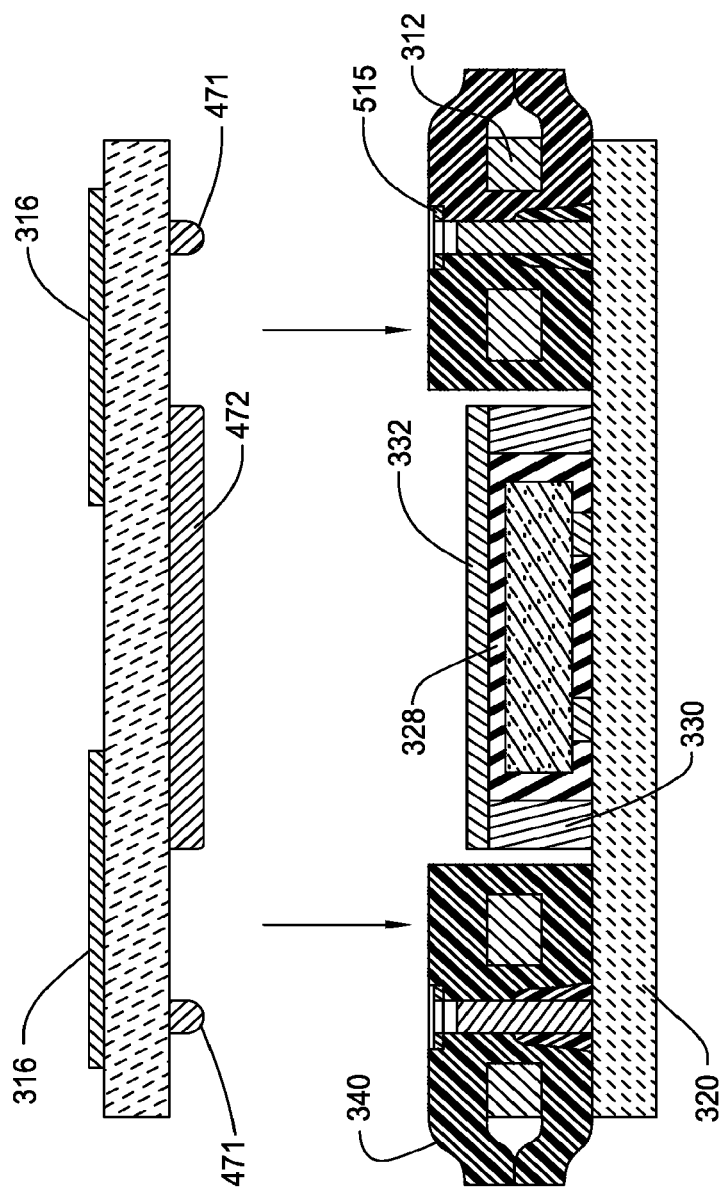
FIG. 76 illustrates the positioning of the carrier-laminate sub-assembly over the substrate and the positioning of the superstrate over the carrier-lid sub-assembly.

Superstrates 336 are then disposed over the top surface of the laminate 340, as represented by FIG. 76. As a consequence of this seating of the superstrates 336, each solder plug 471 extends through laminate top layer openings 518 and partially through the underlying middle layer opening 512. Each superstrate solder plug 471 is therefore in registration with and contacts an underlying substrate solder plug 453, as seen by FIG. 77. As a further result of the positioning of the superstrates 336, each solder plug 472 seats in one of the windows 490 integral with laminate top layer 486. Each superstrate solder plug 472 contacts the exposed surface of the underlying lid 332.

At this time, the opposed substrates 320 and superstrates 336 are pressed towards each other and heated, (subjected to thermal compression bonding.) This heat causes solder plugs 453, 471 and 472 to liquefy. The solder plugs of each substrate solder plug 453-superstrate solder plug pair 471 bond together. Each of these bonded pairs of solder plugs forms one of the posts 344 that extend from substrate 320, through laminate 340 to the superstrate 336. Thus, the posts 344 function as fastening components that holds each substrate 320 and complementary superstrate 336 to the carrier-laminate sub-assembly. During this bonding process, a fraction of the solder integral with each superstrate solder plug 471 flows over and bonds to the associated capture pad 515. Each post 344 therefore also functions as a conductive member over which signals are transferred to/from, the substrate vias 447, the superstrate vias 462 and/or the laminate capture pads.

As mentioned above, as a consequence of the addition of heat in this step, superstrate plugs 472 also liquefy. Each solder plug 472 therefore bonds with the underlying lid 332. Further, a portion of solder forming each plug 472 flows along the outer surface of the adjacent shell containment ring 330. Some of this solder reaches the surface of the step 456 that projects beyond the outer perimeter of containment ring 330. The solder forming solder plug 472 therefore, in addition to bonding with the lid 332, bonds with both ring 330 and the exposed face of gold layer 454 that forms the step 456 around ring 330. Upon rehardening, solder plug 472 forms an additional fastening member that holds each substrate 320 and complementary superstrate 332 together.

Cable 50 is attached to bond pads located at the proximal end of the laminate middle layer 484. The method of attaching cable 50 is not part of this invention.

The formation of the posts 344 and the bonding of solder plugs 472 to substrate 320 can be considered the completion of the process of assembling electrode array 310 of this invention. The array 310 may then be tested, testing not being part of the present invention.

Once the array 310 is ready for use, the array may be folded for insertion in a delivery cannula. The array is bent along two longitudinal axes. A first one of these axes, axis 544 in FIG. 51 is centered on the line between the carrier tabs 314 that project laterally from bridge sections 382 from the adjacent tabs 315 that project from bridge sections 384. A second one of these axes, axis 546 in FIG. 51, is centered on the line between the carrier tabs 314 that project laterally from bridge sections 384 and the adjacent tabs that extend from bridge sections 386. Arbitrarily, the array 310 is bent first so bridge sections 382 and the tabs 314 integral therewith are disposed under the bridge sections 384 and the tabs 314 integral therewith. Then, the array is bent so bridge sections 386 and the tabs 314 associated therewith are disposed under bridge sections 382 and the tabs 314 associated therewith. This bending, it should be appreciated occurs around the carrier beams 388. If carrier 314 is formed from elastic material, this bending of the beams 388 stores potential energy in the beams.

The bending results in the width of the electrode array 310 being reduced so it can fit in the delivery cannula, (not illustrated and not part of this invention.) Often the delivery cannula has a lumen with a diameter smaller than the width across the unfolded array.

Once the delivery cannula is positioned over the tissue at which the array 310 is to be deployed, the array and cannula are separated from each other. Again, the exact method is not part of this invention. For point of reference it should be understood that in one array delivery, the delivery cannula may be opened up. In another method of array delivery, the cannula is retracted away from the array. In either method, once the array is freed from the constraining cannula, the potential energy stored by the folded carrier beams 388 releases. The beams 388 unfold so as to unbend the whole of the array. Thus the array 310 transitions from the folded state to the unfolded state. When the array 310 so unfolds, the plural rows of electrodes 316 become directed towards the tissue against which the current is to be flowed.

Current can then be selectively sourced from one set of electrodes 316 and sunk to a second set of electrodes. This current flow is targeted to flow through the tissue through which such current flow will have a combination of highly beneficial therapeutic effects and tolerable side effects. As discussed above each control module 318 contains components for sourcing and/or sinking different amounts of current to each electrode 316 to which the control module is connected.

Electrode array 310 is constructed so that the individual electrodes 316 are formed on ridged members, the superstrates 336. Since these backings on which the electrodes 316 are formed are rigid, during delivery of the array the electrodes themselves are themselves resistant to bending. For the same reason, the electrodes 316, when pressed against uneven tissue, are not prone bending. This bending, if allowed to occur, can result in deformation of the components forming the electrodes. If this deformation is significant, it can result in fracturing of the component layers of the electrode. Such fracturing of the electrode components, can result in electrode malfunction or failure. Again though, array 310 is constructed so that the sub-assemblies forming the electrodes 316 resist bending. This serves to minimize the possibility that such bending could be the cause of electrode and, by extension, array malfunction.

Similarly, substrates 320 function as rigid backings for the control modules 318. The rigidity of an individual substrate 320 makes it unlikely that bending induced stresses can induce unequal and unbalanced stresses on the solder joints that extend from the control module bond pads 422 to the substrate vias 445. The minimization of these stresses on these solder joints results in a like reduction in that such stresses can result in the failure of the joints. Such failures, if allowed to occur, would at least adversely affect the operation of the associated electrodes 316.

Moreover, embedded in each substrate 320 are the vias 445 and 447 and traces 443 that provide the electrical connections that lead to the associated control module 318. Given the rigid nature of the substrates, these conductive members likewise do not flex. This means that these conductive members are essentially not subjected flexure induced stresses that could result in failure causing fractures.

Each substrate 320 and superstrate 336 has at least one major surface that is non-porous. The minor surfaces, the side surfaces, of each substrate 320 and superstrate 336 are likewise essentially non-porous. Disposed between the substrate 320 and the superstrate 336 is the laminate 340. Given that the laminate is formed from layers of LCP, this component is likewise non-porous. This means that the each substrate-laminate-superstrate stack of components constitute an outer case or shell around the encased control module 318 has a essentially a liquid tight, if not gas tight barrier. Within substrate-laminate-superstrate stack the control module 318 is then encased on one major face and around the perimeter by ring 330 and lid 332. These components are likewise non-porous. Within the ring 330 and lid 332, substantially all of the control module 318 is encased in a non-porous shell.

In sum, three non-porous sub-assemblies substantially encase each control module 318. Collectively, these assemblies substantially eliminate the likelihood that patient's fluids can contact the control module. Likewise the laminate 340 is constructed so as to prevent the conductors 344 from being exposed to the patient. Preventing these components of the array from exposure to the patient's fluids results in a like reduction in the possibility that such exposure could damage these components.

It is still a further feature of this invention that the substrate-superstrate pairs of this invention are spaced apart from each other. Thus while the substrate-superstrate pairs both prevent component bending and block component exposure to bodily fluids, they do not prevent bending of the array 310 around the carrier beams 388. This allows electrode array 310 to, as described above, be folded into a delivery cannula with a diameter smaller than width of the array.

Electrode array 310 is thus an assembly that has a large number of electrodes 316 that are disposed over a relatively small surface area. In some versions of this invention, the array 310 can have 20 more electrodes 316 that are disposed in an area of 3 cm$^2$. The current sourced from/sunk to each electrode can be individually set. This means array 310 can be used to provide current flow through underlying tissue that is precisely targeted. The array 310 can be folded into a width narrower than the deployed width of the array. This makes it possible to fold the array into a delivery cannula designed to facilitate the percutaneous delivery and deployment of the array. Further, the components forming the array define plural non-porous barrier layers around at least the array control modules. This feature of the array substantially eliminates the possibility that body fluid can come into contact with the arrays and the attendant damage caused by such contact.

VII. Alternative Embodiments

It should be appreciated that the foregoing is directed to specific constructions and specific methods of assembly of the electrode arrays of this invention.

The features of electrode arrays 40, 40a, 40b and 310 may be selectively combined. For example, in an alternative version of the invention, the carrier assembly may consist of the Nitinol (metal) frame encased in parylene. In this version of the invention, the control modules may be mounted to the rigid backings and the electrodes may similarly be formed on rigid backings.

Also there is no requirement that in all versions of the invention that each electrode array include plural control modules. In some versions of the invention, it may only be necessary to provide the electrode array with a single carrier-embedded control module. Electrode array 310 is described as having a pair of electrodes connected to each control module 318. In alternative versions of this embodiment of the invention, each control module may include the components that source current to and/or sink current from, one or three or more electrodes. It should therefore be appreciated that there is no requirement that in each version of the invention, the control module that sources current to or which current is sunk from an electrode be mounted to the carrier so as to subtend the area occupied by the electrode. Thus it is contemplated that in some versions of the invention, the control modules may be mounted in locations in the carrier that are spaced away from the locations over which the electrodes are formed.

Also, it may be necessary to provide an electrode array of this invention with one or more control circuits that, owing to their design, cannot be assembled into carrier-implantable control modules. In these versions of the invention one or more of these additional control modules may be mounted to either the active or passive side of the electrode array.

Similarly, the functions of the embedded control modules are not limited to modules that source/sink current to the electrodes. Some control modules may contain components useful for processing signals received by the electrodes. Thus when a particular electrode does not function as a current source or sink, these components internal to the control module process the potential measured by the electrode so these potential measurements can be further processed by other components. Whether or not a specific control module contains components to source current and/or sink current and/or process a potential measured by an electrode or electrodes is a function of the specific electrode array. Still other alternative control modules may not include any of these processing components. These control modules may include devices for storing the charge that is used to flow current between the electrodes. Other control modules may include components for providing connections between the electrode array 40 and components off the array.

Likewise, the shapes of the components may be different from what has been described. Thus, while in the described versions of the invention, the electrodes are located on tabs that are separate from the surrounding sections of the carrier, this is not required in all versions of the invention. There is no requirement that in all versions of the invention, the electrodes be arranged in the row by column array. Thus, for some applications of the invention, the electrodes may be arranged in a single column on the carrier.

Similarly, there is no requirement that in all versions of the invention, the control modules be seated in windows that extend completely through the carrier. In some versions of the invention, the carrier may be formed with recesses that do not extend all the way through the carrier. In these versions of the invention, the material forming the passivation frame is applied to the surfaces of the carrier that form the bases of the recesses. Thus, in these versions of the invention, the material forming the passivation frame forms a shell that insulating frame between the die forming control module 44 and the surrounding carrier.

Likewise, there is no requirement that in all versions of the invention, the electrode array be formed from the disclosed components. For example, there is no requirement that in all versions of the invention the carrier be formed from material that is superelastic or even material that is deformable. In some versions of the invention, the carrier can be formed from material that is simply flexible. This is usefully when constructing an electrode array that is to be placed against irregularly shaped tissue. In these and other versions of the invention, the carrier therefore may not be formed from metal or other electrically conductive material. Thus, the carrier may formed from a plastic such as silicone or a polyamide. In versions of the invention wherein the carrier is not formed from electrically conductive material, the need to provide an electrical insulating shell and/or frame between the control module and the carrier may be eliminated.

Similarly, for example, ribs 521 may not be needed to "fill in" troughs in the carrier-laminate assembly that may form as a consequence of adjacent layers LCP bonding together where the carrier is not present. Alternatively, the ribs 521 may be formed by depositing silicon oxide or other filler material in the troughs. Then once the ribs are formed, portions of electrically insulating laminate forming material and the ribs themselves are removed to define the through bores in which the posts are subsequently formed.

The number of conductors extending to the electrodes 42 and 316 and to the embedded control modules 44 and 318 should likewise be recognized as illustrative, not limiting. In some versions of the invention, to ensure charging balancing across a single electrode 42 plural vias or other conductors may extend from the control module to that electrode. Likewise, in some versions of the invention only a single conductor or three or more conductors may extend to the embedded control module. For example, in some versions of the invention, one conductor may serve as a common power bus. This bus serves as the conductor over which power, and only power, is distributed to each of the control modules 44. One or more additional conductors function as the bus over which control signals are broadcast to the control modules and data are received back from the control modules.

In the illustrated version of the invention, conductors 46 and 48 that extend to the embedded control module are shown as stacked one below the other. This is likewise understood to be for purposes of illustration and not limiting. In some versions of the invention, if the conductors are positioned on different heights they may not overlap each other. In some versions of the inventions plural conductors that are located at the same height, (that are disposed over the same insulating layer) may extend to one or more common control members.

Likewise, in some versions of the invention, some of the conductors may extend directly to the electrodes. Also, it may be desirable to provide vias that connect the conductors located at different heights, (that are disposed over different insulating layers,) with vias. These vias are formed by employing variations of the above described fabrication techniques. Thus, after an insulating layer is formed over a conductor, a hole is formed in the layer so as to terminate over the conductor. The next level conductor is formed over the outer insulating layer. As part of this process of forming this conductor, some of the metal forming the conductor flows into this hole to form a conductor-to-conductor via.

The process steps performed to fabricate an electrode array of this invention likewise may differ from what has been described. Thus, the process steps of the different versions of the invention may be selectively combined. Also, preformed sheets of insulating material and or conductors that are partially or fully shaped to their final forms may be used to form, respectively, one or more of the insulating layers or conductors of the invention.

Similarly, the die forming the control module 44 may not simply be seated in the associated shell. In some versions of the invention, a layer of parylene may be applied to the inner surfaces of the walls of the shell prior to the placement of the die. Once the parylene layer is established, the die is placed in the shell. Given the elastic nature of this parylene layer, the parylene layer functions as shock absorber that reduces the mechanical shock and vibrations to which the control module is exposed. Alternatively, or in addition to the parylene, an adhesive may be applied to the die so as to secure the control module 44 in the shell.

Likewise, an adhesive may be applied to the outer surface of the shells 84. When the shells are seated in the windows 81 of the carrier, this adhesive forms a bond between the shell 84 and the adjacent frame 81 of window-defining surface of the carrier 81.

Similarly, there is no requirement that all the features of electrode array 310 of this invention be used together. Some versions of the invention may include the described superstrates that function as rigid backings for the associated electrodes. These versions of the invention may not include the underlying substrates. Likewise, some electrode arrays may include the described substrates upon which the control modules are mounted and not the superstrates for providing rigid backings for the electrodes.

Alternatively, in some versions of the array rigid backings may perform two functions. As seen in FIG. 78, in these versions of the invention, the electrodes 317 may be formed on one surface of the ceramic member, here substrate 321, while the control modules 318 and their complementary non-porous shell (or shells) are disposed on the opposed surface. In these versions of the invention these electrode-rigid backing-control module assemblies may be mounted to the carrier so that the encased control modules are seated in windows formed in the carrier. In one version of this embodiment, the rigid backings are only provided on one side of the carrier. In these versions of the structures similar to posts 344 both hold the backings to the carrier and provide the conductive paths between the carrier conductors and the control modules. The posts may extend to small ceramic islands on the opposed side of the carrier. One advantage of this versions of the invention the connections between a control module and the electrode (or electrodes) to which it is connected can be by vias 542 that extend through the common rigid backing, substrate 321 in FIG. 78. Another advantage of this version of the invention is that eliminates the need to provide both sides of the carrier with rigid components that have the surface area of the rigid backings.

In an alternative version of this embodiment of the invention, the version seen in FIG. 78, the electrode array may still have a second set of rigid backings, here superstrates 336. These rigid backings are located on the surface of the carrier opposite the surface on which the backings carrying both the electrodes 317 and control modules 318 are mounted. The rigid backings of this second set of backings support their own electrodes 316. Thus, in this version of the invention is constructed so that electrodes disposed on spaced apart rigid backings are located on both sides of the carrier.

Also, there may not be any requirement to provide an electrode arrays with a superelastic carrier. These carrier, for example may not be needed for arrays that are not intended for percutaneous insertion. In these versions of the invention, the control modules may simply be embedded in a flexible, electrically insulating carrier. Again, in order to protect the control modules from the environment, the modules may be encased in one or more non-porous caps.

Further, should the insulating carrier be formed from a laminate, such as LCP, there is no requirement in all versions of the invention the laminate have three layers. In alternative assembles, the laminate may consist of two or four or more layers.

Additional variations in the components forming the electrode array of this invention are also possible. For example, the rigid backings to which the electrodes 316 and control modules 318 are mounted need not always be made of ceramic. These backings can be formed of other material such as plastics into which conductors can be embedded. Similarly, silicon oxide need not always be the make-up material that forms the non-porous conformal shell disposed over the control modules 318. In other versions of the invention, other coatings, such as epoxies and polymers may function as the shell-forming coating. Likewise, the shell may not always include a conformal coating. In some versions of the invention, the shell may include a preformed non-porous cap that is simply fitted in place on the rigid backing around the control module 318. Thus, in some versions of the invention ring 330 and lid 332, without the filler silicon oxide, may form the non-porous cap portion of the shell bounded to the rigid backing to which the control module is attached. In these versions of the invention, the rigid backing, the ring, and lid would collectively form the non-porous shell around the control module 318.

Therefore, it is the goal of the appended claims to cover all such modifications and variations that come within the true spirit and scope of this invention.

The invention claimed is:

1. An implantable electrode array comprising:
   a carrier that is flexible;
   at least one control module coupled to the carrier;
   a shell encasing the control module;
   at least one electrode coupled to the carrier and being electrically connected to the control module; and
   wherein the control module is layered between the carrier and the electrode.

2. The implantable electrode array of claim 1, further comprising a rigid backing to which the control module is mounted.

3. The implantable electrode array of claim 2, wherein the rigid backing is non-porous.

4. The implantable electrode array of claim 2, wherein the shell comprises a non-porous conformal coating applied over the control module and the rigid backing.

5. The implantable electrode array of claim 2, wherein the control module and the rigid backing are mounted to the carrier.

6. The implantable electrode array of claim 2, further comprising a conductive member electrically connecting the control module and the electrode, wherein the conductive member is integrated with the rigid backing.

7. The implantable electrode array of claim 2, further a conductive member electrically connecting the control module and the electrode, wherein the conductive member extends through the rigid backing.

8. The implantable electrode array of claim 1, further comprising a ring surrounding the shell and the control module.

9. The implantable electrode array of claim 8, further comprising a lid secured to the ring to extend over the shell and the control module.

10. The implantable electrode array of claim 1, wherein the shell comprises conformal coating applied over the control module.

11. The implantable electrode array of claim 1, wherein the shell comprises electrically insulating and non-porous material.

12. The implantable electrode array of claim 1, wherein the shell comprises synthetic resin.

13. The implantable electrode array of claim 1, wherein the carrier is layered between the control module and the electrode.

14. The implantable electrode array of claim 1, further comprising a conductive member electrically connecting the control module and the electrode, wherein the conductive member extends through the carrier.

15. The implantable electrode array of claim 1, wherein the control module comprises an application specific integrated circuit.

16. The implantable electrode array of claim 1, further comprising a plurality of control modules with each control module being encased by a shell, and a plurality electrodes and wherein the encased control modules are spaced from one another on the carrier.

17. The implantable electrode array of claim 16, wherein each control module is layered in an overlapping relationship relative to a pair of electrodes.

18. An implantable electrode array comprising:
a carrier that is flexible;
at least one control module coupled to the carrier;
a shell encasing the control module;
at least one electrode coupled to the carrier and being electrically connected to the control module; and
wherein the carrier is layered between the control module and the electrode.

19. An implantable electrode array comprising:
a carrier that is flexible;
at least one control module coupled to the carrier;
a shell encasing the control module;
a ring surrounding the shell and the control module; and
at least one electrode coupled to the carrier and being electrically connected to the control module.

20. The implantable electrode array of claim 19, further comprising a lid secured to the ring to extend over the shell and the control module.

21. An implantable electrode array comprising:
a carrier that is flexible;
a plurality of control modules coupled to the carrier and each control module being encased by a shell;
a plurality of electrodes coupled to the carrier and being electrically connected to the plurality of control modules; and
wherein the plurality of encased control modules are spaced from one another on the carrier.

22. The implantable electrode array of claim 21, wherein each of the plurality of control modules is layered in an overlapping relationship relative to a pair of electrodes.

* * * * *